United States Patent [19]
Thomashow et al.

[11] Patent Number: 5,955,298
[45] Date of Patent: *Sep. 21, 1999

[54] SEQUENCES FOR PRODUCTION OF 2,4-DIACETYLPHLOROGLUCINOL AND METHODS

[75] Inventors: Linda S. Thomashow; Mahalaxmi Bangera; David M. Weller; R. James Cook, all of Pullman, Wash.

[73] Assignees: The United States of America as represented by the Secretary of Agriculture, Washington, D.C.; Washington State University Research Foundation, Pullman, Wash.

[*] Notice: This patent issued on a continued prosecution application filed under 37 CFR 1.53(d), and is subject to the twenty year patent term provisions of 35 U.S.C. 154(a)(2).

[21] Appl. No.: 08/494,907

[22] Filed: Jun. 26, 1995

[51] Int. Cl.$^6$ ............ C12D 21/02; C07H 21/04; C12N 1/21; C12N 9/14

[52] U.S. Cl. ............ 435/69.1; 435/183; 435/195; 435/252.3; 435/320.1; 536/23.2; 536/23.7; 536/24.32; 530/350

[58] Field of Search ............ 435/69.1, 252.3, 435/320.1, 183, 195; 530/350; 536/22.1, 23.7, 23.2, 24.32

[56] References Cited

U.S. PATENT DOCUMENTS

| | | | |
|---|---|---|---|
| 5,518,901 | 5/1996 | Murtagh | 435/91.2 |
| 5,744,306 | 4/1998 | Murtagh, Jr. et al. | 435/6 |

OTHER PUBLICATIONS

Bangera et al. Genetic analysis of the 2,4-diacetylphlorglucinol Curr. Plant Sci. Biotechicol Agroc. (1994) vol. 21, pp. 383–386.

M. G. Bangera et al., "Characterization of a Locus Required for Synthesis of 2,4-Diacetylphloroglucinol by *Pseudomonas aureofaciens* Q2–87," *Abstracts of Papers: Sixth International Congress of Plant Pathology*, p. 68 (1993).

M. G. Bangera et al., "Characterization of a Locus Required for Synthesis of 2,4-Diacetylphloroglucinol by *Psuedomonas aureofaciens* Q2–87," *Abstracts of Papers: 4th International Symposium on Pseudomonas: Biotechnology and Molecular Biology*, p. 178 (1993).

M. G. Bangera et al., "Genetic Analysis of a Locus Required for Synthesis of 2,4-Diacetylphloroglucinol by *Pseudomonas aureofaciens* Q2–87," *Phytopathology* 83:1385 (1993).

D. N. Dowling and F. O'Gara, "Metabolites of Pseudomonas Involved in the Biocontrol of Plant Disease," *Tibtech* 12:133–141 (1994).

A. M. Fenton et al., "Exploitation of Gene(s) Involved in 2,4-Diacetylphoroglucinol Biosynthesis to Confer a New Biocontrol Capability to a Pseudomonas Strain," *Applied and Environmental Microbiology* 58:3873–3878 (1992).

A. M. Fenton et al., "Cloning and Heterologous Expression of Genes Involved in 2,4-Diacetylphloroglucinol Biosynthesis in Pseudomonas Strains," *In Abstracts of the Fourth International Symposium on Pseudomonas: Biotechnology and Molecular Biology*, Ed. R.E.W. Hancock, Vancouver, B.C., Canada, p. 49 (1993).

(List continued on next page.)

*Primary Examiner*—Kawai Lau
*Attorney, Agent, or Firm*—M. Howard Silverstein; John D. Fado; Margaret A. Connor

[57] ABSTRACT

DNA sequences which function specifically in the synthesis of 2,4-diacetylphloroglucinol (Phl) are described. The sequences include phl genes which encode phl gene proteins and coding and regulatory sequences for production of Phl as well as sequences containing phl genes, which sequences have the capability of conferring or enhancing Phl biosynthetic capability in bacterial strains. The transformed strains are useful as biocontrol agents against fungal pathogens.

51 Claims, 8 Drawing Sheets

Phl

OTHER PUBLICATIONS

H. Hara et al., "Effect of Transfer and Expression of Antibiotic Biosynthesis Genes on Biological Control Ativity of Fluorescent Pseudomonads," In *Improving Plant Productivity with Rhizobacteria*, Eds. Ryder, Stephens and Bowen, CSIRO Division of Soils, Adelaide, South Australia, pp. 247–249 (1994).

L. A. Harrison et al., "Purification of an Antibiotic Effective Against *Gaeumannomyces graminis* var. Tritici Produced by a Biocontrol Agent, *Pseudomonas aureofaciens*," *Soil Biol. Biochem.* 25:215–221 (1993).

C. Keel et al., "Suppression of Root Diseases by *Pseudomonas fluorescens* CHAO: Importance of the Bacterial Secondary Metabolite 2,4–Diacetylphoroglucinol," *Molecular Plant–Microbe Interactions* 5:4–13 (1992).

C. Keel et al., "Pseudomonads as Antagonists of Plant Pthogens in the Rhizosphere: Role of the Antibiotic 2,4–Diacetylphoroglucinol in the Suppression of Black Root Rot of Tobacco," *Symbiosis* 9:327–341 (1990).

M. Maurhofer et al., "Influence of Enhanced Antibiotic Production in *Pseudomonas fluorescens* Strain CHAO on its Disease Suppressive Capacity," *Phytopathology* 82:190–195 (1992).

D. O'Sullivan and F. O'Gara, "Traits of Fluorescent *Pseudomonas* spp. Involved in Suppression of Plant Root Pathogens," *Microbiol. Rev.* 56:662–676 (1992).

P. Shanahan et al., "Liquid Chromatographic Assay of Microbially Derived Phloroglucinol Antibiotics for Establishing the Biosynthetic Route to Production, and the Factors Affecting Their Regulation," *Analytica Chim. Acta* 272:271–277 (1993).

P. Shanahan et al., "Isolation of 2,4–Diacetylphloroglucinol from a Fluorescent Pseudomonad and Investigation of Physiological Parameters Influencing its Production," *Applied and Environmental Microbiology* 58:353–358 (1992).

M. A. Vincent et al., "Genetic Analysis of the Antifungal Activity of a Soilborne *Pseudomonas aureofaciens* Strain," *Applied and Environmental Microbiology* 57:2928–2934 (1991).

D. Weller and L. S. Thomashow, "Microbial Metabolites with Biological Activity Against Plant Pathogens," In *Pest Management: Biologically Based Technologies*, Eds. R. D. Lumsden and J. L. Vaughn, pp. 173–180 (1993).

D. Weller and L. S. Thomashow, "Use of Rhizobacteria for Biocontrol," *Current Opinion in Biotechnology* 4:306–311 (1993).

| Protein | Sequence | | | | | | | | | HTH Score |
|---|---|---|---|---|---|---|---|---|---|---|
| 434 rep | Q | A | E | L | A | Q | K | V | G T Q Q S I E N | 1875 |
| 434 cro | Q | T | E | L | A | T | K | A | G V K M Q S I H A | 1274 |
| Lamb rep | Q | E | S | V | A | D | K | M | G M G Q S G V G A L F N | 1553 |
| Lamb cro | Q | T | K | T | A | K | D | L | G V Y Q S A H K A I H | 1626 |
| CRP | R | Q | E | I | G | E | I | V | G C S R E T V G R I L K | 1916 |
| Lac rep | L | Y | D | V | A | R | L | A | G V S Y Q T V S R V N | 2052 |
| Ec 1721 | T | R | K | L | A | E | R | L | G V Q Q P A L Y W H F K | 2090 |
| Ec tetc | T | R | K | L | A | E | R | L | G V E Q P T L Y W H V K | 1997 |
| Tet rep | T | R | K | L | A | Q | K | L | G V E Q P T I Y W H V K | 1994 |
| PhlF | I | E | A | V | A | R | R | A | G A S K P T I Y R W W G | 1886 |
| Myco lep | I | D | E | A | E | R | L | A | G V S R A L M Y H Y P | 1487 |
| Ec bet | I | A | Q | I | A | R | R | A | G V S T G I S H Y R | 2015 |
| Consensus | Q | E | E | L | A | E | R | L | G V S Q P T I C R F L K | |

FIG. 8

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
       (A) LENGTH: 3680 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Pseudomonas fluorescens (ix) FEATURE:
       (A) NAME/KEY: misc_feature
       (B) LOCATION: complement (2889..3680)
       (D) OTHER INFORMATION: /note= "phlA, transcribed from
           right to left"

(ix) FEATURE:
       (A) NAME/KEY: misc_feature
       (B) LOCATION: complement (1210..1917)
       (D) OTHER INFORMATION: /note= "phlB, transcribed from
           right to left"

(ix) FEATURE:
       (A) NAME/KEY: misc_feature (B) LOCATION: complement (1689..2855)
                (D) OTHER INFORMATION: /note= "phlC, transcribed from
                    right to left"

(ix) FEATURE:
                (A) NAME/KEY: misc_feature
                (B) LOCATION: complement (2..1048)
                (D) OTHER INFORMATION: /note= "phlD, transcribed from
                    right to left"

(ix) FEATURE:
                (A) NAME/KEY: misc_feature
                (B) LOCATION: 2118..3371
                (D) OTHER INFORMATION: /note= "phlR, transcribed from left
                    to right"

(ix) FEATURE:
                (A) NAME/KEY: misc_feature
                (B) LOCATION: 1..3680
                (D) OTHER INFORMATION: /note= "SEQ ID NO:1 contains genes
                    necessary for Phl synthesis."

(xi) SEQUENCE DESCRIPTION: SEQ ID NO:1:

```
AGGCCACCCA CTTGCCCACG GCCATTTCAG CTGTGAAGCC AGGGCCGAAG GCTGCCAGCA      60
TGCCGGTCGC TCCATTGGCC GGCCCGCTGT CGAACTGGCG CTTGAGGACG TCGAAGACCA     120
CCACGCTGGC AATATTGCCG GCCTCGCTCA AGCTGTCGCG AGACTGCGCG ACCCTGCCAG     180
GTTCCAGATC GAGCTGCAGC ACCAGCTCAT CAAGAATTTT TCGTCCACCG GTGTGGAAGA     240
TGAAAAAGTC ATTTTGAGCG CAATGTTGGT TGAAGGTCTC GAAGTTCAAT TCCTCCATCA     300
TCGGGGCCAC GTCTTTAATG GAGTTCATGA CGGCTTTGTC CAGGGTGAAG TGAAAGCCGC     360
TGTCCTTGAC GTCATATTTA ATGTAGTGCT CGCTGTCAGG CAGGAAATAA GAGCCGGTTT     420
TGGCGATCTT GAATCCCGGC GCCTTATCGT CGGCGCGCAT TACGCAGGCC GAGACGGCAT     480
CGCCGAACAG CGCTGCGGAT ATGAACGCGT GCAACTTGGT GTCCTGTGGT TGATAGCAGA     540
GTGACGAGAA CTCCAGCGAG ACAATAAGGG CGTGGTTGTC TGGAGACAGG CTGCCAAAGT     600
CGTTGGCTCG ATTAATCGCC GCGGCGCCTG CCACGCATCC CAATTGAGCG ATCGGCAATT     660
GTACGGTCGA CGTTCGCAGT CCCAAGTCAT TGATCAGGTG GGCTGTCAGC GATGGCATCA     720
TGAACCCGGT GCAAGAGGTA ACGGCGACCA TCCGGATGTC GTCCGTGGTC AAGCCCGCGT     780
TTTCAATGGC CTGGCGCGCG GCGATTGAAG ACATGCGGCG AGCCTCTCGC TCATACACGA     840
TGCTGCGGTG GGTAAAGCCG GTATGCACCG CAAGTTCATC GATGGGCAAG ACCAGATACC     900
GTTCATTGAC TTGGGTGTTT TGAATCATCC GTTTAGCCAA TGCCATGCGC GGATGATCGT     960
CATGCAACTG TTCCAAGTGA TCGATCATCT GTTGTTGGGT AATTTTGTAA TGCGGGAAAA    1020
GCAAGCTGGG TTTGCAAAGA GTAGACATGA CAAGTCCTCG GCTGAAAGCC AATAAAGAGT    1080
AGAAAACCAC GTTTAAGGCA ATGGCAAAGC AGGACTCTGA AAAGCAGAAT CAAACAACGG    1140
GCCGGTTGGC CGGAAATAGC GACTGTTGTT ATGGATGGCG CGGTATGCAG CAAGTAACTT    1200
GTTTGGTTAT TTCGCCAATA CGAATTTATA AGCGTATTGC CACGCCAGGT TGCTTTCCCG    1260
AACGTGCTTG CGAATAACCA TTCGCACTGG TGCTCCAGTC ACGACTTGCC GGGGATCGAC    1320
GACATCGACG ATTTCCGAGG CGATCACCAA GCCATCGTCC AGGCGCACCA TTGCCATGAA    1380
GCGCGGGACG GTTTCGCCAT ATCCCATGGC CGCGAGAATG GGGTTTTCAG CATGGGCGCT    1440
GACCTGGATC GTGCCGGTGC GTGCGCAGCG ATACGGTTCC ACGTTCAATG AGTTGCATGC    1500
GCCGCAGACG GTGCGCCGTG GAAGAAGAT TTCTTCGCAA TCCTGGCAGC GGCTGCCTTC    1560
GAGACGATAT TTTCCGCCAT GTTCGCGCCA TTCGCGCAAC ATGCTGGCGG TGGTCATGCG    1620
GTGTATTTGT TCTGGGTAAA GGGACATGGT CGGCTCCTTA ATCGTTGGAA AGCACAATGA    1680
```

```
CGCTGTTATG CGCGGCGTAA CCGCCCAAGT TCCTGCGAGA CGCCAATGCG AGCGTCCTTG    1740

ACTTGGTTGT TGGACTCGCC GCGAAGTTGT CGGAACAGCT CGGTAATGTG CAGGATGCCG    1800

TCGCAACCAG AGGCGTGGCC GCGGCCAATA TTGCCGCCAT CGGTGTTTAA TGGCAGTTGC    1860

CCGTCGAGGG CTATGCCGCC TTCCAATACA AAGTCGCCTG CCTGGCCTGG ACCACATACG    1920

CCCATGGATT CCATCTGAAT CAATCCGGCA CCCAGCAAGT CGTAGACTTG GCCACATCG     1980

ATATCCTTGG CGGTGATGCC GGCTTTTTTG TAGGCGATTT CGGCGCAAGC AATGGAGTTG    2040

GCGGAAACCG CCATGCCGAC GTCTTTTGGC AGGCCTGGAT ATTTCAGGGT CGGGTTGTGA    2100

TAGCGCGTCC CGAAATAATG GGATACGCCG GTATAGGCAC AACCACGGAC GAATACCGGT    2160

TGGGTCGTGT AGCGGTGCGC CAGGTGTTCG GCGACCAGGA TGGCGCAACC GCTGGCTTCA    2220

CCCCAGGCCA GCATCGAGCC ACATGCTTCG CTGTTCTTGA GGGTTTCAAG GGATGGCACC    2280

GGCACGCCAT AGCGGGTTGC CGTGGGCGTG TTGTGCGCAT AGATGCGCAT TTGCCGACCA    2340

AACGTTGCCA GGACATCCGC TTCGCGTCCT GCATAGCCAA ATTTTTCAAA ATATTCGGCG    2400

GTTGCGAGGG CAAAGGCGTC GGTGTGCGAA ATGCCCAGGA AATAATCGTA CTCACATTCG    2460

GTACTGGAGC CGATGTATTC GGCATAGTTG AAGTGGTCGG TCATTTTTTC AAAGCCACCA    2520

CACAGGACGA TGTCGTACTC ACCCGAGGCG ACCATCTGAT GGGCCATCTG AAAGGAAACC    2580

GAGCTGCTGG TGCAGTTGGC AGTGCTCATG AACGTCGGGG CAGGGCTGAT GCCCAGGGCA    2640

TCGGAAATAG TCGGGCCCAG GCCGCCGTAT TCGGAAATAC CTTCACCGTG ATATCCATAA    2700

GCGACTGCCT GAAGTTCACG GGGATGCATC TTGATGGCGT TGAGCGCCTG ATAGGCGGAC    2760

TCGACGATCA TCTCCTTGAA GGTTTGACGG ACTCTGGAGC TGCCGGGTTT GGAAGTATAG    2820

GCAGCCGAAA CGATAGCAAC GCGTCGTGCG CTCATTGGAA GTGCTCCTTG CTGGATGGTT    2880

GGGAATCAGA GGTAGGCTGT CAGGGCGTAG TCAGGCCGCA AGTATTTGAA CTCGTACTTG    2940

ATCGACGTCC CGTAATCCAC GTAATACTTG TCTTCCAGCA GCGTGCGCAG CGCAACGTTG    3000

GTCTTTTGGT AGGCTTCGAT GGCATCGGTC ACTGTCAACG CAATCGCATC GCTGCCCGCA    3060

CCAAACCCGT ACGACACCAA GAGGATTTTT TCACCCGGAC GCGCTCGGTC CAGTACGCTC    3120

ACCAAGCCCA GCAACGGACT CGCGGGCCCC GCATCACCGA CACTCTGGGC ATAAATGCCA    3180

GGTTCGATCT GCGCTTTGGT GAAGCCCAGG CCTTTGCCAA GAGAGAAGGG GGTCGAAACC    3240

AGGTTTTGCT GGAATACGAC ATAGTCGAAA TCGCTGGCCT GTACATTCAT CTTGGCCATC    3300

AATCCCGACG CAGCACGATG GGTCTGGTCT TCAAGGCCAA TGCTGTTCTT GTCGGAGCCC    3360

AGCCCCATTC CTGAGCGAAT GTAGCGGTCT CCCTGGGGGC GGATGTTGTC AGCCACATCG    3420

GCGGCGCAAG AAAAGCTGGC ATCGAAATGC GCGATCACAT TTTCAGTACC CAACAACAGT    3480

GCGGCGGCTC CCGCTCCGGC GTAGGACTCG GTCAAGTCGC CGGGGCGGT GTTGCGGTTG     3540

ATCGTATCGG CGCCTATTGC CAGTGCATTG CCGGCCATGC CCGAGGCTAC CAGGGCATAG    3600

GCGATCTGCA GGGCGCTGGT GCCTGATTTG CCGGCAAACT GTACGTCCGC GCAGAAGGCG    3660

TCATAACCGC AGCCGAGCAT                                                3680
```

(2) INFORMATION FOR SEQ ID NO:2:

(i) SEQUENCE CHARACTERISTICS:
        (A) LENGTH: 5076 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Pseudomonas fluorescens (ix) FEATURE:
    (A) NAME/KEY: misc_feature
    (B) LOCATION: complement (4285..5076)
    (D) OTHER INFORMATION: /note= "phlA, transcribed from right to left"

(ix) FEATURE:
    (A) NAME/KEY: misc_feature
    (B) LOCATION: complement (2606..3313)
    (D) OTHER INFORMATION: /note= "phlB, transcribed from right to left"

(ix) FEATURE:
    (A) NAME/KEY: misc_feature
    (B) LOCATION: complement (3085..4251)
    (D) OTHER INFORMATION: /note= "phlC, transcribed from right to left"

(ix) FEATURE:
    (A) NAME/KEY: misc_feature
    (B) LOCATION: complement (1398..2444)
    (D) OTHER INFORMATION: /note= "phlD, transcribed from right to left"

(ix) FEATURE:
    (A) NAME/KEY: misc_feature
    (B) LOCATION: 3514..4767
    (D) OTHER INFORMATION: /note= "phlR, transcribed from left to right"

(ix) FEATURE:
    (A) NAME/KEY: misc_feature
    (B) LOCATION: complement (2..1270)
    (D) OTHER INFORMATION: /note= "phlE, transcribed from right to left"

(ix) FEATURE:
    (A) NAME/KEY: misc_feature
    (B) LOCATION: 1..5076
    (D) OTHER INFORMATION: /note= "SEQ ID NO:2 contains genes involved in synthesis, activity, and/or export of Phl."

(xi) SEQUENCE DESCRIPTION: SEQ ID NO:2:

```
ACTTATCCTC CAGCGTCAAG CGAGCGGGCA GGGGGCCGTA GTCCGCACGG TCATTGAAAA      60

CAGAGCTGGC TTCCTTGAGC CGCAGGGACA GAAACCCGCC CATCAAACTA CCAGCCAGTG     120

CCAGAAACAG AATGGCGGTA AGCCCCCAGT TCACGGCGAT GTACCCGGCG ACCACGGGCG     180

CAACGCCACC GCCCAGGATT TCTCCGCAAC CCACCACCAG GCCCGTAGCG GTGGCCAGTA     240

AACTGGGTGG CACTGATTCG CTGGTCAGTG GGCCGACGGT GATGCAGATC AGGCTGAAAT     300

TGATGAAAGA TAAAAGAAC AGCTGGAGGA ACAGTAGCCA CGGTAACGGC GGGGAAATGA      360

TGAGCAAGCC GACCAGTAGT GTGCTGATCA GGAAGCAGAT GGAAACGACA GGCTTGCGGC     420

CCAGTTGGTC AGACAAACCG GGAATGACGA GCTGGCCGAA AAAACCACCC AGGCCGATCG     480

CGGAGATGAT CATGGCCATG GAGAAATTGC TCAGGTGCAA GACGTCTGTC AGGTAGCTGG     540

GGAGCAGGGC GCACAGGACG AATTGGCACG TCAGTATGCA TAGCATCAAG GCAATGTTGA     600

GGCGCACGTT GCCGCTGGAC AGGGCTGTTC GCCATTGGCT GCCGGAGGGT TCTACGAGCG     660

GCCTTGGATG GGGCGCCTGG CTCGGTTGGT AGGTTCGATA CAGATACCAG GCCACCAGCA     720

GGCCCGGCAA CGAGATGATG GCGAACACGG CGCGCCACGA TCCGAACATT TCAAACAATA     780

CGCCCGCCAG CAGCGGCCCC AGGCACAGGC CGATGATGGG AAACAGTGCC TGCTGGATGC     840

CCAGGTTGAG CCCGCGTCGG CACGGCTGCG AAACTTCATC GGTGACAATG ATGCTGACCG     900
```

```
GGGTGAAGGC GCCTTCGCAG ATCCCCATCA AGGCGCGCAG GAGCACCAGG CCCATAAGGC    960

TTGAGATCAA CGCAGATGCG CCGGCCAGGA GCGATACCAA GGTAATCGAA AGCACCAGCA   1020

GTTGCTTGGT GCCCAATCGC CTGATAGCAA CGCCCATGAA GAGGGCCGAG CCTCCCCAGG   1080

CAAATGCCAG GATCGCCGAT AACAGGCCCA GGTCCTGATA GTCCAGGGCC AGGTCATGCA   1140

TGATCACCGG GAACAACGGC ATGATAATGA ATCGATCAAG TCCTACCAGC CCGAAGCTCA   1200

GCGACAAAAG AACGACCATG CGTCTTTCGT AGCCACCCCA AGGTCGAGTG CAAGATACG    1260

TACTCTCCAT GTTCTTCCCC TTCTTTCCTT AGCCCTTTCG ACGTTTTCTC GAAACGGGTG   1320

AACGCTTGTG TTCGATACTC CTGTAGCCAG GGGCGGATCC GCCCCCGGCT TGGTGCGTGC   1380

AATGTGTTGG TCTGTCAGGC CACCCACTTG CCCACGGCCA TTTCAGCTGT GAAGCCAGGG   1440

CCGAAGGCTG CCAGCATGCC GGTCGCTCCA TTGGCCGGCC CGCTGTCGAA CTGGCGCTTG   1500

AGGACGTCGA AGACCACCAC GCTGGCAATA TTGCCGGCCT CGCTCAAGCT GTCGCGAGAC   1560

TGCGCGACCC TGCCAGGTTC CAGATCGAGC TGCAGCACCA GCTCATCAAG AATTTTTCGT   1620

CCACCGGTGT GGAAGATGAA AAAGTCATTT TGAGCGCAAT GTTGGTTGAA GGTCTCGAAG   1680

TTCAATTCCT CCATCATCGG GGCCACGTCT TTAATGGAGT TCATGACGGC TTTGTCCAGG   1740

GTGAAGTGAA AGCCGCTGTC CTTGACGTCA TATTTAATGT AGTGCTCGCT GTCAGGCAGG   1800

AAATAAGAGC CGGTTTTGGC GATCTTGAAT CCCGGCGCCT TATCGTCGGC GCGCATTACG   1860

CAGGCCGAGA CGGCATCGCC GAACAGCGCT GCGGATATGA ACGCGTGCAA CTTGGTGTCC   1920

TGTGGTTGAT AGCAGAGTGA CGAGAACTCC AGCGAGACAA TAAGGGCGTG GTTGTCTGGA   1980

GACAGGCTGC CAAAGTCGTT GGCTCGATTA ATCGCCGCGG CGCCTGCCAC GCATCCCAAT   2040

TGAGCGATCG GCAATTGTAC GGTCGACGTT CGCAGTCCCA AGTCATTGAT CAGGTGGGCT   2100

GTCAGCGATG GCATCATGAA CCCGGTGCAA GAGGTAACGG CGACCATCCG GATGTCGTCC   2160

GTGGTCAAGC CCGCGTTTTC AATGGCCTGG CGCGCGGCGA TTGAAGACAT GCGGCGAGCC   2220

TCTCGCTCAT ACACGATGCT GCGGTGGGTA AAGCCGGTAT GCACCGCAAG TTCATCGATG   2280

GGCAAGACCA GATACCGTTC ATTGACTTGG GTGTTTTGAA TCATCCGTTT AGCCAATGCC   2340

ATGCGCGGAT GATCGTCATG CAACTGTTCC AAGTGATCGA TCATCTGTTG TTGGGTAATT   2400

TTGTAATGCG GGAAAAGCAA GCTGGGTTTG CAAAGAGTAG ACATGACAAG TCCTCGGCTG   2460

AAAGCCAATA AAGAGTAGAA AACCACGTTT AAGGCAATGG CAAAGCAGGA CTCTGAAAAG   2520

CAGAATCAAA CAACGGGCCG GTTGGCCGGA AATAGCGACT GTTGTTATGG ATGGCGCGGT   2580

ATGCAGCAAG TAACTTGTTT GGTTATTTCG CCAATACGAA TTTATAAGCG TATTGCCACG   2640

CCAGGTTGCT TTCCCGAACG TGCTTGCGAA TAACCATTCG CACTGGTGCT CCAGTCACGA   2700

CTTGCCGGGG ATCGACGACA TCGACGATTT CCGAGGCGAT CACCAAGCCA TCGTCCAGGC   2760

GCACCATTGC CATGAAGCGC GGGACGGTTT CGCCATATCC CATGGCCGCG AGAATGGGGT   2820

TTTCAGCATG GGCGCTGACC TGGATCGTGC CGGTGCGTGC GCAGCGATAC GGTTCCACGT   2880

TCAATGAGTT GCATGCGCCG CAGACGGTGC GCCGTGGGAA GAAGATTTCT TCGCAATCCT   2940

GGCAGCGGCT GCCTTCGAGA CGATATTTTC CGCCATGTTC GCGCCATTCG CGCAACATGC   3000

TGGCGGTGGT CATGCGGTGT ATTTGTTCTG GGTAAAGGGA CATGGTCGGC TCCTTAATCG   3060

TTGGAAAGCA CAATGACGCT GTTATGCGCG GCGTAACCGC CCAAGTTCCT GCGAGACGCC   3120

AATGCGAGCG TCCTTGACTT GGTTGTTGGA CTCGCCGCGA AGTTGTCGGA ACAGCTCGGT   3180

AATGTGCAGG ATGCCGTCGC AACCAGAGGC GTGGCCGCGG CCAATATTGC CGCCATCGGT   3240

GTTTAATGGC AGTTGCCCGT CGAGGGCTAT GCCGCCTTCC AATACAAAGT CGCCTGCCTG   3300
```

```
GCCTGGACCA CATACGCCCA TGGATTCCAT CTGAATCAAT CCGGCACCCA GCAAGTCGTA    3360

GACTTGGGCC ACATCGATAT CCTTGGCGGT GATGCCGGCT TTTTTGTAGG CGATTTCGGC    3420

GCAAGCAATG GAGTTGGCGG AAACCGCCAT GCCGACGTCT TTTGGCAGGC CTGGATATTT    3480

CAGGGTCGGG TTGTGATAGC GCGTCCCGAA ATAATGGGAT ACGCCGGTAT AGGCACAACC    3540

ACGGACGAAT ACCGGTTGGG TCGTGTAGCG GTGCGCCAGG TGTTCGGCGA CCAGGATGGC    3600

GCAACCGCTG GCTTCACCCC AGGCCAGCAT CGAGCCACAT GCTTCGCTGT TCTTGAGGGT    3660

TTCAAGGGAT GGCACCGGCA CGCCATAGCG GGTTGCCGTG GGCGTGTTGT GCGCATAGAT    3720

GCGCATTTGC CGACCAAACG TTGCCAGGAC ATCCGCTTCG CGTCCTGCAT AGCCAAATTT    3780

TTCAAAATAT TCGGCGGTTG CGAGGGCAAA GGCGTCGGTG TGCGAAATGC CCAGGAAATA    3840

ATCGTACTCA CATTCGGTAC TGGAGCCGAT GTATTCGGCA TAGTTGAAGT GGTCGGTCAT    3900

TTTTTCAAAG CCACCACACA GGACGATGTC GTACTCACCC GAGGCGACCA TCTGATGGGC    3960

CATCTGAAAG GAAACCGAGC TGCTGGTGCA GTTGGCAGTG CTCATGAACG TCGGGGCAGG    4020

GCTGATGCCC AGGGCATCGG AAATAGTCGG GCCCAGGCCG CCGTATTCGG AAATACCTTC    4080

ACCGTGATAT CCATAAGCGA CTGCCTGAAG TTCACGGGGA TGCATCTTGA TGGCGTTGAG    4140

CGCCTGATAG GCGGACTCGA CGATCATCTC CTTGAAGGTT TGACGGACTC TGGAGCTGCC    4200

GGGTTTGGAA GTATAGGCAG CCGAAACGAT AGCAACGCGT CGTGCGCTCA TTGGAAGTGC    4260

TCCTTGCTGG ATGGTTGGGA ATCAGAGGTA GGCTGTCAGG GCGTAGTCAG GCCGCAAGTA    4320

TTTGAACTCG TACTTGATCG ACGTCCCGTA ATCCACGTAA TACTTGTCTT CCAGCAGCGT    4380

GCGCAGCGCA ACGTTGGTCT TTTGGTAGGC TTCGATGGCA TCGGTCACTG TCAACGCAAT    4440

CGCATCGCTG CCCGCACCAA ACCCGTACGA CACCAAGAGG ATTTTTTCAC CCGGACGCGC    4500

TCGGTCCAGT ACGCTCACCA AGCCCAGCAA CGGACTCGCG GGCCCCGCAT CACCGACACT    4560

CTGGGCATAA ATGCCAGGTT CGATCTGCGC TTTGGTGAAG CCCAGGCCTT TGCCAAGAGA    4620

GAAGGGGTC GAAACCAGGT TTTGCTGGAA TACGACATAG TCGAAATCGC TGGCCTGTAC    4680

ATTCATCTTG GCCATCAATC CCGACGCAGC ACGATGGGTC TGGTCTTCAA GGCCAATGCT    4740

GTTCTTGTCG GAGCCCAGCC CCATTCCTGA GCGAATGTAG CGGTCTCCCT GGGGGCGGAT    4800

GTTGTCAGCC ACATCGGCGG CGCAAGAAAA GCTGGCATCG AAATGCGCGA TCACATTTTC    4860

AGTACCCAAC AACAGTGCGG CGGCTCCCGC TCCGGCGTAG GACTCGGTCA AGTCGCCGGG    4920

GGCGGTGTTG CGGTTGATCG TATCGGCGCC TATTGCCAGT GCATTGCCGG CCATGCCCGA    4980

GGCTACCAGG GCATAGGCGA TCTGCAGGGC GCTGGTGCCT GATTTGCCGG CAAACTGTAC    5040

GTCCGCGCAG AAGGCGTCAT AACCGCAGCC GAGCAT                              5076
```

(2) INFORMATION FOR SEQ ID NO:3:

(i) SEQUENCE CHARACTERISTICS:
        (A) LENGTH: 6387 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pseudomonas fluorescens (ix) FEATURE:

(A) NAME/KEY: misc_feature
       (B) LOCATION: complement (4285..5076)
       (D) OTHER INFORMATION: /note= "phlA, transcribed from
             right to left"

(ix) FEATURE:
       (A) NAME/KEY: misc_feature
       (B) LOCATION: complement (2606..3313)
       (D) OTHER INFORMATION: /note= "phlB, transcribed from
             right to left"

(ix) FEATURE:
       (A) NAME/KEY: misc_feature
       (B) LOCATION: complement (3085..4251)
       (D) OTHER INFORMATION: /note= "phlC, transcribed from
             right to left"

(ix) FEATURE:
       (A) NAME/KEY: misc_feature
       (B) LOCATION: complement (1398..2444)
       (D) OTHER INFORMATION: /note= "phlD, transcribed from
             right to left"

(ix) FEATURE:
       (A) NAME/KEY: misc_feature
       (B) LOCATION: 3514..4767
       (D) OTHER INFORMATION: /note= "phlR, transcribed from left
             to right"

(ix) FEATURE:
       (A) NAME/KEY: misc_feature
       (B) LOCATION: complement (2..1270)
       (D) OTHER INFORMATION: /note= "phlE, transcribed from
             right to left"

(ix) FEATURE:
       (A) NAME/KEY: misc_feature
       (B) LOCATION: 5781..6386
       (D) OTHER INFORMATION: /note= "phlF, transcribed from left
             to right"

(ix) FEATURE:
       (A) NAME/KEY: misc_feature
       (B) LOCATION: 1..6387
       (D) OTHER INFORMATION: /note= "SEQ ID NO:3 contains genes
             involved in synthesis and modulation of synthesis
             of Phl."

(xi) SEQUENCE DESCRIPTION: SEQ ID NO:3:

ACTTATCCTC CAGCGTCAAG CGAGCGGGCA GGGGGCCGTA GTCCGCACGG TCATTGAAAA      60

CAGAGCTGGC TTCCTTGAGC CGCAGGGACA GAAACCCGCC CATCAAACTA CCAGCCAGTG     120

CCAGAAACAG AATGGCGGTA AGCCCCCAGT TCACGGCGAT GTACCCGGCG ACCACGGGCG     180

CAACGCCACC GCCCAGGATT TCTCCGCAAC CCACCACCAG GCCCGTAGCG GTGGCCAGTA     240

AACTGGGTGG CACTGATTCG CTGGTCAGTG GGCCGACGGT GATGCAGATC AGGCTGAAAT     300

TGATGAAAGA TAAAAAGAAC AGCTGGAGGA ACAGTAGCCA CGGTAACGGC GGGGAAATGA     360

TGAGCAAGCC GACCAGTAGT GTGCTGATCA GGAAGCAGAT GGAAACGACA GGCTTGCGGC     420

CCAGTTGGTC AGACAAACCG GGAATGACGA GCTGGCCGAA AAAACCACCC AGGCCGATCG     480

CGGAGATGAT CATGGCCATG GAGAAATTGC TCAGGTGCAA GACGTCTGTC AGGTAGCTGG     540

GGAGCAGGGC GCACAGGACG AATTGGCACG TCAGTATGCA TAGCATCAAG GCAATGTTGA     600

GGCGCACGTT GCCGCTGGAC AGGGCTGTTC GCCATTGGCT GCCGGAGGGT TCTACGAGCG     660

GCCTTGGATG GGGCGCCTGG CTCGGTTGGT AGGTTCGATA CAGATACCAG GCCACCAGCA     720

GGCCCGGCAA CGAGATGATG GCGAACACGG CGCGCCACGA TCCGAACATT TCAAACAATA     780

CGCCCGCCAG CAGCGGCCCC AGGCACAGGC CGATGATGGG AAACAGTGCC TGCTGGATGC     840

CCAGGTTGAG CCCGCGTCGG CACGGCTGCG AAACTTCATC GGTGACAATG ATGCTGACCG     900

```
GGGTGAAGGC GCCTTCGCAG ATCCCCATCA AGGCGCGCAG GAGCACCAGG CCCATAAGGC    960

TTGAGATCAA CGCAGATGCG CCGGCCAGGA GCGATACCAA GGTAATCGAA AGCACCAGCA   1020

GTTGCTTGGT GCCCAATCGC CTGATAGCAA CGCCCATGAA GAGGGCCGAG CCTCCCCAGG   1080

CAAATGCCAG GATCGCCGAT AACAGGCCCA GGTCCTGATA GTCCAGGGCC AGGTCATGCA   1140

TGATCACCGG GAACAACGGC ATGATAATGA ATCGATCAAG TCCTACCAGC CCGAAGCTCA   1200

GCGACAAAAG AACGACCATG CGTCTTTCGT AGCCACCCCA AGGTCGAGTG GCAAGATACG   1260

TACTCTCCAT GTTCTTCCCC TTCTTTCCTT AGCCCTTTCG ACGTTTTCTC GAAACGGGTG   1320

AACGCTTGTG TTCGATACTC CTGTAGCCAG GGGCGGATCC GCCCCCGGCT TGGTGCGTGC   1380

AATGTGTTGG TCTGTCAGGC CACCCACTTG CCCACGGCCA TTTCAGCTGT GAAGCCAGGG   1440

CCGAAGGCTG CCAGCATGCC GGTCGCTCCA TTGGCCGGCC CGCTGTCGAA CTGGCGCTTG   1500

AGGACGTCGA AGACCACCAC GCTGGCAATA TTGCCGGCCT CGCTCAAGCT GTCGCGAGAC   1560

TGCGCGACCC TGCCAGGTTC CAGATCGAGC TGCAGCACCA GCTCATCAAG AATTTTTCGT   1620

CCACCGGTGT GGAAGATGAA AAAGTCATTT TGAGCGCAAT GTTGGTTGAA GGTCTCGAAG   1680

TTCAATTCCT CCATCATCGG GGCCACGTCT TTAATGGAGT TCATGACGGC TTTGTCCAGG   1740

GTGAAGTGAA AGCCGCTGTC CTTGACGTCA TATTTAATGT AGTGCTCGCT GTCAGGCAGG   1800

AAATAAGAGC CGGTTTTGGC GATCTTGAAT CCCGGCGCCT TATCGTCGGC GCGCATTACG   1860

CAGGCCGAGA CGGCATCGCC GAACAGCGCT GCGGATATGA ACGCGTGCAA CTTGGTGTCC   1920

TGTGGTTGAT AGCAGAGTGA CGAGAACTCC AGCGAGACAA TAAGGGCGTG GTTGTCTGGA   1980

GACAGGCTGC CAAAGTCGTT GGCTCGATTA ATCGCCGCGG CGCCTGCCAC GCATCCCAAT   2040

TGAGCGATCG GCAATTGTAC GGTCGACGTT CGCAGTCCCA AGTCATTGAT CAGGTGGGCT   2100

GTCAGCGATG GCATCATGAA CCCGGTGCAA GAGGTAACGG CGACCATCCG GATGTCGTCC   2160

GTGGTCAAGC CCGCGTTTTC AATGGCCTGG CGCGCGGCA TTGAAGACAT GCGGCGAGCC   2220

TCTCGCTCAT ACACGATGCT GCGGTGGGTA AAGCCGGTAT GCACCGCAAG TTCATCGATG   2280

GGCAAGACCA GATACCGTTC ATTGACTTGG GTGTTTTGAA TCATCCGTTT AGCCAATGCC   2340

ATGCGCGGAT GATCGTCATG CAACTGTTCC AAGTGATCGA TCATCTGTTG TTGGGTAATT   2400

TTGTAATGCG GGAAAAGCAA GCTGGGTTTG CAAAGAGTAG ACATGACAAG TCCTCGGCTG   2460

AAAGCCAATA AGAGTAGAA AACCACGTTT AAGGCAATGG CAAAGCAGGA CTCTGAAAAG   2520

CAGAATCAAA CAACGGGCCG GTTGGCCGGA ATAGCGACT GTTGTTATGG ATGGCGCGGT   2580

ATGCAGCAAG TAACTTGTTT GGTTATTTCG CCAATACGAA TTTATAAGCG TATTGCCACG   2640

CCAGGTTGCT TTCCCGAACG TGCTTGCGAA TAACCATTCG CACTGGTGCT CCAGTCACGA   2700

CTTGCCGGGG ATCGACGACA TCGACGATTT CCGAGGCGAT CACCAAGCCA TCGTCCAGGC   2760

GCACCATTGC CATGAAGCGC GGGACGGTTT CGCCATATCC CATGGCCGCG AGAATGGGGT   2820

TTTCAGCATG GGCGCTGACC TGGATCGTGC CGGTGCGTGC GCAGCGATAC GGTTCCACGT   2880

TCAATGAGTT GCATGCGCCG CAGACGGTGC GCCGTGGGAA GAAGATTTCT TCGCAATCCT   2940

GGCAGCGGCT GCCTTCGAGA CGATATTTTC CGCCATGTTC GCGCCATTCG CGCAACATGC   3000

TGGCGGTGGT CATGCGGTGT ATTTGTTCTG GGTAAAGGGA CATGGTCGGC TCCTTAATCG   3060

TTGGAAAGCA CAATGACGCT GTTATGCGCG GCGTAACCGC CCAAGTTCCT GCGAGACGCC   3120

AATGCGAGCG TCCTTGACTT GGTTGTTGGA CTCGCCGCGA AGTTGTCGGA ACAGCTCGGT   3180

AATGTGCAGG ATGCCGTCGC AACCAGAGGC GTGGCCGCGG CCAATATTGC CGCCATCGGT   3240

GTTTAATGGC AGTTGCCCGT CGAGGGCTAT GCCGCCTTCC AATACAAAGT CGCCTGCCTG   3300
```

```
GCCTGGACCA CATACGCCCA TGGATTCCAT CTGAATCAAT CCGGCACCCA GCAAGTCGTA    3360

GACTTGGGCC ACATCGATAT CCTTGGCGGT GATGCCGGCT TTTTTGTAGG CGATTTCGGC    3420

GCAAGCAATG GAGTTGGCGG AAACCGCCAT GCCGACGTCT TTTGGCAGGC CTGGATATTT    3480

CAGGGTCGGG TTGTGATAGC GCGTCCCGAA ATAATGGGAT ACGCCGGTAT AGGCACAACC    3540

ACGGACGAAT ACCGGTTGGG TCGTGTAGCG GTGCGCCAGG TGTTCGGCGA CCAGGATGGC    3600

GCAACCGCTG GCTTCACCCC AGGCCAGCAT CGAGCCACAT GCTTCGCTGT TCTTGAGGGT    3660

TTCAAGGGAT GGCACCGGCA CGCCATAGCG GGTTGCCGTG GGCGTGTTGT GCGCATAGAT    3720

GCGCATTTGC CGACCAAACG TTGCCAGGAC ATCCGCTTCG CGTCCTGCAT AGCCAAATTT    3780

TTCAAAATAT TCGGCGGTTG CGAGGGCAAA GGCGTCGGTG TGCGAAATGC CCAGGAAATA    3840

ATCGTACTCA CATTCGGTAC TGGAGCCGAT GTATTCGGCA TAGTTGAAGT GGTCGGTCAT    3900

TTTTTCAAAG CCACCACACA GGACGATGTC GTACTCACCC GAGGCGACCA TCTGATGGGC    3960

CATCTGAAAG GAAACCGAGC TGCTGGTGCA GTTGGCAGTG CTCATGAACG TCGGGCAGG    4020

GCTGATGCCC AGGGCATCGG AAATAGTCGG GCCCAGGCCG CCGTATTCGG AAATACCTTC    4080

ACCGTGATAT CCATAAGCGA CTGCCTGAAG TTCACGGGGA TGCATCTTGA TGGCGTTGAG    4140

CGCCTGATAG GCGGACTCGA CGATCATCTC CTTGAAGGTT TGACGGACTC TGGAGCTGCC    4200

GGGTTTGGAA GTATAGGCAG CCGAAACGAT AGCAACGCGT CGTGCGCTCA TTGGAAGTGC    4260

TCCTTGCTGG ATGGTTGGGA ATCAGAGGTA GGCTGTCAGG GCGTAGTCAG GCCGCAAGTA    4320

TTTGAACTCG TACTTGATCG ACGTCCCGTA ATCCACGTAA TACTTGTCTT CCAGCAGCGT    4380

GCGCAGCGCA ACGTTGGTCT TTTGGTAGGC TTCGATGGCA TCGGTCACTG TCAACGCAAT    4440

CGCATCGCTG CCCGCACCAA ACCCGTACGA CACCAAGAGG ATTTTTTCAC CCGGACGCGC    4500

TCGGTCCAGT ACGCTCACCA AGCCCAGCAA CGGACTCGCG GGCCCCGCAT CACCGACACT    4560

CTGGGCATAA ATGCCAGGTT CGATCTGCGC TTTGGTGAAG CCCAGGCCTT TGCCAAGAGA    4620

GAAGGGGTC GAAACCAGGT TTTGCTGGAA TACGACATAG TCGAAATCGC TGGCCTGTAC    4680

ATTCATCTTG GCCATCAATC CCGACGCAGC ACGATGGGTC TGGTCTTCAA GGCCAATGCT    4740

GTTCTTGTCG GAGCCCAGCC CCATTCCTGA GCGAATGTAG CGGTCTCCCT GGGGGCGGAT    4800

GTTGTCAGCC ACATCGGCGG CGCAAGAAAA GCTGGCATCG AAATGCGCGA TCACATTTTC    4860

AGTACCCAAC AACAGTGCGG CGGCTCCCGC TCCGGCGTAG GACTCGGTCA AGTCGCCGGG    4920

GGCGGTGTTG CGGTTGATCG TATCGGCGCC TATTGCCAGT GCATTGCCGG CCATGCCCGA    4980

GGCTACCAGG GCATAGGCGA TCTGCAGGGC GCTGGTGCCT GATTTGCCGG CAAACTGTAC    5040

GTCCGCGCAG AAGGCGTCAT AACCGCAGCC GAGCATTTCC AGAATGACCG CGGCCGAGGC    5100

GCGGGAGTCA TATGGGTTGG TGCACGTACC CAGGTACAGC GCTTCCAGGT CGCAAGAAGG    5160

GGCTTTGTCC AGCGCACGTT GAGCGGCCAG GACACTCAAG GTAATGACGT CCTCATCGGG    5220

TTGGAGTACA GCCCTTTCAA CGACGCCCAG TTGGTTGGTG ACCAGACTCA AGTCTGTGTT    5280

TTTCCAGACG TGGATCACGT CTTCCACTTT AAGGCGGCAC ACCGGGATGC CCGCGCCATA    5340

GCTCACAATT CCTACTTTAT TCACGTGTAC TTCCTCCAGA TTCCTTTCTT CACCTGCCAG    5400

CGGATAGCCG TGACCGATGC ATGAAATATT TAGAAACTAT CTAACGGTGC CCGCAAAGTG    5460

TCGTTGGCAG TCCTATGCCC GGAAATCGGG CTCCTCAAGG GGGAAAACTA CAGTTCCTTT    5520

GAGGGAGAAC GGGTTTATTA TCCTTCTATT ATTATGTATG ATACGAAACG TGCCGTATCG    5580

TTAAGGTCTT GTTAAAAATT GATGACTATT TATCGGGTTT CTTCCTATCT AGTGGCAAGT    5640

TCCGCTATTG AGGTGTGCAG TTAAGCAGAA ACTTAGATCA TAAAAACATA CCAAAACGAA    5700
```

```
ACGATCCGTT TCATTGCTTT TCGAGAGAAT CCTATACCTT GCGTCTCTTT TGTCAAGCGC      5760

CATATTGGAG ATTTTGAATT ATGGCCCGTA AACCGTCTCG GAGCTCCATT GGCTCATTGA      5820

GGAGCCCACA TACGCACAAA GCGATCATCA TCTCCGCTAT AGAAACACTC AAGGAGTGCG      5880

GTTATTCAGG GTTGAGTATC GAGGCTGTGG CTCGCCGTGC CGGCGCGAGC AAGCCGACCA      5940

TCTATCGATG GTGGGGTAAC AAGGCGGCTT TGATCGCCGA AGTCTACGAG AGCGAAAGCG      6000

AGCAGATTCG CAAGGAGCCT GATAAAGGAT CCTTCAAGGA GAACCTCAAT TTCCTGCTGC      6060

TCAATCTGTG GAAGGTCTGG AGAGAAACGA TTTGCGGGGA GGCGTTTCGG TGTGTCATCG      6120

CTGAAGCCCA GCTCGACCCC AGTACGCTGC CCAAGCTGAA GGATGAATTC ATGGAGCGTC      6180

GTCGGGAATT GCCGCGAAAG CTGGTGGAAA ACGCCATCCA GCAAGGTGAG TTGCCCAAGG      6240

ACACGTCCCG TGAGTTGTTG TTGGACATGA TCTTCGGATT TTGCTGGTAC AGGCTGTTGA      6300

CTGAGCAACT GGAAGTGGAG GGTGACATCA ATGAATTCAC GACGCTTCTG TTGAACGGCG      6360

TGTTGCGTAC GACTTCGGCG GCGGAGT                                          6387
```

(2) INFORMATION FOR SEQ ID NO:4:

(i) SEQUENCE CHARACTERISTICS:
        (A) LENGTH: 6170 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pseudomonas fluorescens (ix) FEATURE:
        (A) NAME/KEY: misc_feature
        (B) LOCATION: complement (4285..5076)
        (D) OTHER INFORMATION: /note= "phlA, transcribed from
            right to left"

(ix) FEATURE:
        (A) NAME/KEY: misc_feature
        (B) LOCATION: complement (2606..3313)
        (D) OTHER INFORMATION: /note= "phlB, transcribed from
            right to left"

(ix) FEATURE:
        (A) NAME/KEY: misc_feature
        (B) LOCATION: complement (3085..4251)
        (D) OTHER INFORMATION: /note= "phlC, transcribed from
            right to left"

(ix) FEATURE:
        (A) NAME/KEY: misc_feature
        (B) LOCATION: complement (1398..2444)
        (D) OTHER INFORMATION: /note= "phlD, transcribed from
            right to left"

(ix) FEATURE:
        (A) NAME/KEY: misc_feature
        (B) LOCATION: 3514..4767
        (D) OTHER INFORMATION: /note= "phlR, transcribed from
            left to right"

(ix) FEATURE:
        (A) NAME/KEY: misc_feature
        (B) LOCATION: complement (2..1270)
        (D) OTHER INFORMATION: /note= "phlE, transcribed from
            right to left"

(ix) FEATURE:
        (A) NAME/KEY: misc_feature (B) LOCATION: 5781..6170
(D) OTHER INFORMATION: /note= "phlF, truncated, transcribed from left to right"

(ix) FEATURE:
(A) NAME/KEY: misc_feature
(B) LOCATION: 1..6170
(D) OTHER INFORMATION: /note= "SEQ ID NO:4 contains genes involved in synthesis, and modulation of synthesis of Phl."

(xi) SEQUENCE DESCRIPTION: SEQ ID NO:4:

```
ACTTATCCTC CAGCGTCAAG CGAGCGGGCA GGGGGCCGTA GTCCGCACGG TCATTGAAAA      60

CAGAGCTGGC TTCCTTGAGC CGCAGGGACA GAAACCCGCC CATCAAACTA CCAGCCAGTG     120

CCAGAAACAG AATGGCGGTA AGCCCCCAGT TCACGGCGAT GTACCCGGCG ACCACGGGCG     180

CAACGCCACC GCCCAGGATT TCTCCGCAAC CCACCACCAG GCCCGTAGCG GTGGCCAGTA     240

AACTGGGTGG CACTGATTCG CTGGTCAGTG GGCCGACGGT GATGCAGATC AGGCTGAAAT     300

TGATGAAAGA TAAAAAGAAC AGCTGGAGGA ACAGTAGCCA CGGTAACGGC GGGGAAATGA     360

TGAGCAAGCC GACCAGTAGT GTGCTGATCA GGAAGCAGAT GGAAACGACA GGCTTGCGGC     420

CCAGTTGGTC AGACAAACCG GAATGACGA GCTGGCCGAA AAAACCACCC AGGCCGATCG      480

CGGAGATGAT CATGGCCATG GAGAAATTGC TCAGGTGCAA GACGTCTGTC AGGTAGCTGG     540

GGAGCAGGGC GCACAGGACG AATTGGCACG TCAGTATGCA TAGCATCAAG GCAATGTTGA     600

GGCGCACGTT GCCGCTGGAC AGGGCTGTTC GCCATTGGCT GCCGGAGGGT TCTACGAGCG     660

GCCTTGGATG GGGCGCCTGG CTCGGTTGGT AGGTTCGATA CAGATACCAG GCCACCAGCA     720

GGCCCGGCAA CGAGATGATG GCGAACACGG CGCGCCACGA TCCGAACATT TCAAACAATA     780

CGCCCGCCAG CAGCGGCCCC AGGCACAGGC CGATGATGGG AAACAGTGCC TGCTGGATGC     840

CCAGGTTGAG CCCGCGTCGG CACGGCTGCG AAACTTCATC GGTGACAATG ATGCTGACCG     900

GGGTGAAGGC GCCTTCGCAG ATCCCCATCA AGGCGCGCAG GAGCACCAGG CCCATAAGGC     960

TTGAGATCAA CGCAGATGCG CCGGCCAGGA GCGATACCAA GGTAATCGAA AGCACCAGCA    1020

GTTGCTTGGT GCCCAATCGC CTGATAGCAA CGCCCATGAA GAGGGCCGAG CCTCCCCAGG    1080

CAAATGCCAG GATCGCCGAT AACAGGCCCA GGTCCTGATA GTCCAGGGCC AGGTCATGCA    1140

TGATCACCGG GAACAACGGC ATGATAATGA ATCGATCAAG TCCTACCAGC CCGAAGCTCA    1200

GCGACAAAAG AACGACCATG CGTCTTTCGT AGCCACCCCA AGGTCGAGTG CAAGATACG     1260

TACTCTCCAT GTTCTTCCCC TTCTTTCCTT AGCCCTTTCG ACGTTTTCTC GAAACGGGTG    1320

AACGCTTGTG TTCGATACTC CTGTAGCCAG GGGCGGATCC GCCCCCGGCT TGGTGCGTGC    1380

AATGTGTTGG TCTGTCAGGC CACCCACTTG CCCACGGCCA TTTCAGCTGT GAAGCCAGGG    1440

CCGAAGGCTG CCAGCATGCC GGTCGCTCCA TTGGCCGGCC CGCTGTCGAA CTGGCGCTTG    1500

AGGACGTCGA AGACCACCAC GCTGGCAATA TTGCCGGCCT CGCTCAAGCT GTCGCGAGAC    1560

TGCGCGACCC TGCCAGGTTC CAGATCGAGC TGCAGCACCA GCTCATCAAG AATTTTTCGT    1620

CCACCGGTGT GGAAGATGAA AAAGTCATTT TGAGCGCAAT GTTGGTTGAA GGTCTCGAAG    1680

TTCAATTCCT CCATCATCGG GGCCACGTCT TTAATGGAGT TCATGACGGC TTTGTCCAGG    1740

GTGAAGTGAA AGCCGCTGTC CTTGACGTCA TATTTAATGT AGTGCTCGCT GTCAGGCAGG    1800

AAATAAGAGC CGGTTTTGGC GATCTTGAAT CCCGGCGCCT TATCGTCGGC GCGCATTACG    1860

CAGGCCGAGA CGGCATCGCC GAACAGCGCT GCGGATATGA ACGCGTGCAA CTTGGTGTCC    1920

TGTGGTTGAT AGCAGAGTGA CGAGAACTCC AGCGAGACAA TAAGGGCGTG GTTGTCTGGA    1980

GACAGGCTGC CAAAGTCGTT GGCTCGATTA ATCGCCGCGG CGCCTGCCAC GCATCCCAAT    2040
```

```
TGAGCGATCG GCAATTGTAC GGTCGACGTT CGCAGTCCCA AGTCATTGAT CAGGTGGGCT    2100

GTCAGCGATG GCATCATGAA CCCGGTGCAA GAGGTAACGG CGACCATCCG GATGTCGTCC    2160

GTGGTCAAGC CCGCGTTTTC AATGGCCTGG CGCGCGGCGA TTGAAGACAT GCGGCGAGCC    2220

TCTCGCTCAT ACACGATGCT GCGGTGGGTA AAGCCGGTAT GCACCGCAAG TTCATCGATG    2280

GGCAAGACCA GATACCGTTC ATTGACTTGG GTGTTTTGAA TCATCCGTTT AGCCAATGCC    2340

ATGCGCGGAT GATCGTCATG CAACTGTTCC AAGTGATCGA TCATCTGTTG TTGGGTAATT    2400

TTGTAATGCG GGAAAAGCAA GCTGGGTTTG CAAAGAGTAG ACATGACAAG TCCTCGGCTG    2460

AAAGCCAATA AAGAGTAGAA AACCACGTTT AAGGCAATGG CAAAGCAGGA CTCTGAAAAG    2520

CAGAATCAAA CAACGGGCCG GTTGGCCGGA AATAGCGACT GTTGTTATGG ATGGCGCGGT    2580

ATGCAGCAAG TAACTTGTTT GGTTATTTCG CCAATACGAA TTTATAAGCG TATTGCCACG    2640

CCAGGTTGCT TTCCCGAACG TGCTTGCGAA TAACCATTCG CACTGGTGCT CCAGTCACGA    2700

CTTGCCGGGG ATCGACGACA TCGACGATTT CCGAGGCGAT CACCAAGCCA TCGTCCAGGC    2760

GCACCATTGC CATGAAGCGC GGGACGGTTT CGCCATATCC CATGGCCGCG AGAATGGGGT    2820

TTTCAGCATG GGCGCTGACC TGGATCGTGC CGGTGCGTGC GCAGCGATAC GGTTCCACGT    2880

TCAATGAGTT GCATGCGCCG CAGACGGTGC GCCGTGGGAA GAAGATTTCT TCGCAATCCT    2940

GGCAGCGGCT GCCTTCGAGA CGATATTTTC CGCCATGTTC GCGCCATTCG CGCAACATGC    3000

TGGCGGTGGT CATGCGGTGT ATTTGTTCTG GGTAAAGGGA CATGGTCGGC TCCTTAATCG    3060

TTGGAAAGCA CAATGACGCT GTTATGCGCG GCGTAACCGC CCAAGTTCCT GCGAGACGCC    3120

AATGCGAGCG TCCTTGACTT GGTTGTTGGA CTCGCCGCGA AGTTGTCGGA ACAGCTCGGT    3180

AATGTGCAGG ATGCCGTCGC AACCAGAGGC GTGGCCGCGG CCAATATTGC CGCCATCGGT    3240

GTTTAATGGC AGTTGCCCGT CGAGGGCTAT GCCGCCTTCC AATACAAAGT CGCCTGCCTG    3300

GCCTGGACCA CATACGCCCA TGGATTCCAT CTGAATCAAT CCGGCACCCA GCAAGTCGTA    3360

GACTTGGGCC ACATCGATAT CCTTGGCGGT GATGCCGGCT TTTTTGTAGG CGATTTCGGC    3420

GCAAGCAATG GAGTTGGCGG AAACCGCCAT GCCGACGTCT TTTGGCAGGC CTGGATATTT    3480

CAGGGTCGGG TTGTGATAGC GCGTCCCGAA ATAATGGGAT ACGCCGGTAT AGGCACAACC    3540

ACGGACGAAT ACCGGTTGGG TCGTGTAGCG GTGCGCCAGG TGTTCGGCGA CCAGGATGGC    3600

GCAACCGCTG GCTTCACCCC AGGCCAGCAT CGAGCCACAT GCTTCGCTGT TCTTGAGGGT    3660

TTCAAGGGAT GGCACCGGCA CGCCATAGCG GGTTGCCGTG GGCGTGTTGT GCGCATAGAT    3720

GCGCATTTGC CGACCAAACG TTGCCAGGAC ATCCGCTTCG CGTCCTGCAT AGCCAAATTT    3780

TTCAAAATAT TCGGCGGTTG CGAGGGCAAA GGCGTCGGTG TGCGAAATGC CCAGGAAATA    3840

ATCGTACTCA CATTCGGTAC TGGAGCCGAT GTATTCGGCA TAGTTGAAGT GGTCGGTCAT    3900

TTTTTCAAAG CCACCACACA GGACGATGTC GTACTCACCC GAGGCGACCA TCTGATGGGC    3960

CATCTGAAAG GAAACCGAGC TGCTGGTGCA GTTGGCAGTG CTCATGAACG TCGGGGCAGG    4020

GCTGATGCCC AGGGCATCGG AAATAGTCGG GCCCAGGCCG CCGTATTCGG AAATACCTTC    4080

ACCGTGATAT CCATAAGCGA CTGCCTGAAG TTCACGGGGA TGCATCTTGA TGGCGTTGAG    4140

CGCCTGATAG GCGGACTCGA CGATCATCTC CTTGAAGGTT TGACGGACTC TGGAGCTGCC    4200

GGGTTTGGAA GTATAGGCAG CCGAAACGAT AGCAACGCGT CGTGCGCTCA TTGGAAGTGC    4260

TCCTTGCTGG ATGGTTGGGA ATCAGAGGTA GGCTGTCAGG GCGTAGTCAG GCCGCAAGTA    4320

TTTGAACTCG TACTTGATCG ACGTCCCGTA ATCCACGTAA TACTTGTCTT CCAGCAGCGT    4380

GCGCAGCGCA ACGTTGGTCT TTTGGTAGGC TTCGATGGCA TCGGTCACTG TCAACGCAAT    4440
```

```
CGCATCGCTG CCCGCACCAA ACCCGTACGA CACCAAGAGG ATTTTTTCAC CCGGACGCGC    4500

TCGGTCCAGT ACGCTCACCA AGCCCAGCAA CGGACTCGCG GGCCCCGCAT CACCGACACT    4560

CTGGGCATAA ATGCCAGGTT CGATCTGCGC TTTGGTGAAG CCCAGGCCTT TGCCAAGAGA    4620

GAAGGGGTC GAAACCAGGT TTTGCTGGAA TACGACATAG TCGAAATCGC TGGCCTGTAC     4680

ATTCATCTTG GCCATCAATC CCGACGCAGC ACGATGGGTC TGGTCTTCAA GGCCAATGCT    4740

GTTCTTGTCG GAGCCCAGCC CCATTCCTGA GCGAATGTAG CGGTCTCCCT GGGGGCGGAT    4800

GTTGTCAGCC ACATCGGCGG CGCAAGAAAA GCTGGCATCG AAATGCGCGA TCACATTTTC    4860

AGTACCCAAC AACAGTGCGG CGGCTCCCGC TCCGGCGTAG GACTCGGTCA AGTCGCCGGG    4920

GGCGGTGTTG CGGTTGATCG TATCGGCGCC TATTGCCAGT GCATTGCCGG CCATGCCCGA    4980

GGCTACCAGG GCATAGGCGA TCTGCAGGGC GCTGGTGCCT GATTTGCCGG CAAACTGTAC    5040

GTCCGCGCAG AAGGCGTCAT AACCGCAGCC GAGCATTTCC AGAATGACCG CGGCCGAGGC    5100

GCGGGAGTCA TATGGGTTGG TGCACGTACC CAGGTACAGC GCTTCCAGGT CGCAAGAAGG    5160

GGCTTTGTCC AGCGCACGTT GAGCGGCCAG GACACTCAAG GTAATGACGT CCTCATCGGG    5220

TTGGAGTACA GCCCTTTCAA CGACGCCCAG TTGGTTGGTG ACCAGACTCA AGTCTGTGTT    5280

TTTCCAGACG TGGATCACGT CTTCCACTTT AAGGCGGCAC ACCGGGATGC CCGCGCCATA    5340

GCTCACAATT CCTACTTTAT TCACGTGTAC TTCCTCCAGA TTCCTTTCTT CACCTGCCAG    5400

CGGATAGCCG TGACCGATGC ATGAAATATT TAGAAACTAT CTAACGGTGC CCGCAAAGTG    5460

TCGTTGGCAG TCCTATGCCC GGAAATCGGG CTCCTCAAGG GGGAAAACTA CAGTTCCTTT    5520

GAGGGAGAAC GGGTTTATTA TCCTTCTATT ATTATGTATG ATACGAAACG TGCCGTATCG    5580

TTAAGGTCTT GTTAAAAATT GATGACTATT TATCGGGTTT CTTCCTATCT AGTGGCAAGT    5640

TCCGCTATTG AGGTGTGCAG TTAAGCAGAA ACTTAGATCA TAAAAACATA CCAAAACGAA    5700

ACGATCCGTT TCATTGCTTT TCGAGAGAAT CCTATACCTT GCGTCTCTTT TGTCAAGCGC    5760

CATATTGGAG ATTTTGAATT ATGGCCCGTA AACCGTCTCG GAGCTCCATT GGCTCATTGA    5820

GGAGCCCACA TACGCACAAA GCGATCATCA TCTCCGCTAT AGAAACACTC AAGGAGTGCG    5880

GTTATTCAGG GTTGAGTATC GAGGCTGTGG CTCGCCGTGC CGGCGCGAGC AAGCCGACCA    5940

TCTATCGATG GTGGGGTAAC AAGGCGGCTT TGATCGCCGA AGTCTACGAG AGCGAAAGCG    6000

AGCAGATTCG CAAGGAGCCT GATAAAGGAT CCTTCAAGGA GAACCTCAAT TTCCTGCTGC    6060

TCAATCTGTG GAAGGTCTGG AGAGAAACGA TTTGCGGGGA GGCGTTTCGG TGTGTCATCG    6120

CTGAAGCCCA GCTCGACCCC AGTACGCTGC CCAAGCTGAA GGATGAATTC               6170
```

(2) INFORMATION FOR SEQ ID NO:5:

(i) SEQUENCE CHARACTERISTICS:
        (A) LENGTH: 792 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pseudomonas fluorescens (ix) FEATURE:
        (A) NAME/KEY: CDS
        (B) LOCATION: complement (1..792)

(D) OTHER INFORMATION: /note= "phlA DNA sequence. SEQ ID
                 NO:6 is translation (protein) of SEQ ID NO:5."

(xi) SEQUENCE DESCRIPTION: SEQ ID NO:5:

```
GAGGTAGGCT GTCAGGGCGT AGTCAGGCCG CAAGTATTTG AACTCGTACT TGATCGACGT      60

CCCGTAATCC ACGTAATACT TGTCTTCCAG CAGCGTGCGC AGCGCAACGT TGGTCTTTTG     120

GTAGGCTTCG ATGGCATCGG TCACTGTCAA CGCAATCGCA TCGCTGCCCG CACCAAACCC     180

GTACGACACC AAGAGGATTT TTTCACCCGG ACGCGCTCGG TCCAGTACGC TCACCAAGCC     240

CAGCAACGGA CTCGCGGGCC CCGCATCACC GACACTCTGG GCATAAATGC CAGGTTCGAT     300

CTGCGCTTTG GTGAAGCCCA GGCCTTTGCC AAGAGAGAAG GGGGTCGAAA CCAGGTTTTG     360

CTGGAATACG ACATAGTCGA AATCGCTGGC CTGTACATTC ATCTTGGCCA TCAATCCCGA     420

CGCAGCACGA TGGGTCTGGT CTTCAAGGCC AATGCTGTTC TTGTCGGAGC CCAGCCCCAT     480

TCCTGAGCGA ATGTAGCGGT CTCCCTGGGG GCGGATGTTG TCAGCCACAT CGGCGGCGCA     540

AGAAAAGCTG GCATCGAAAT CGCGATCAC ATTTTCAGTA CCCAACAACA GTGCGGCGGC      600

TCCCGCTCCG GCGTAGGACT CGGTCAAGTC GCCGGGGGCG GTGTTGCGGT TGATCGTATC     660

GGCGCCTATT GCCAGTGCAT TGCCGGCCAT GCCCGAGGCT ACCAGGGCAT AGGCGATCTG     720

CAGGGCGCTG GTGCCTGATT TGCCGGCAAA CTGTACGTCC GCGCAGAAGG CGTCATAACC     780

GCAGCCGAGC AT                                                        792
```

(2) INFORMATION FOR SEQ ID NO:6:

(i) SEQUENCE CHARACTERISTICS:
        (A) LENGTH: 264 amino acids
        (B) TYPE: amino acid
        (D) TOPOLOGY: linear (ii) MOLECULE TYPE: protein (xi) SEQUENCE DESCRIPTION: SEQ ID NO:6:

```
Met Leu Gly Cys Gly Tyr Asp Ala Phe Cys Ala Asp Val Gln Phe Ala
 1               5                  10                  15

Gly Lys Ser Gly Thr Ser Ala Leu Gln Ile Ala Tyr Ala Leu Val Ala
             20                  25                  30

Ser Gly Met Ala Gly Asn Ala Leu Ala Ile Gly Ala Asp Thr Ile Asn
         35                  40                  45

Arg Asn Thr Ala Pro Gly Asp Leu Thr Glu Ser Tyr Ala Gly Ala Gly
     50                  55                  60

Ala Ala Ala Leu Leu Leu Gly Thr Glu Asn Val Ile Ala His Phe Asp
 65                  70                  75                  80

Ala Ser Phe Ser Cys Ala Ala Asp Val Ala Asp Asn Ile Arg Pro Gln
                 85                  90                  95

Gly Asp Arg Tyr Ile Arg Ser Gly Met Gly Leu Gly Ser Asp Lys Asn
            100                 105                 110

Ser Ile Gly Leu Glu Asp Gln Thr His Arg Ala Ala Ser Gly Leu Met
        115                 120                 125

Ala Lys Met Asn Val Gln Ala Ser Asp Phe Asp Tyr Val Val Phe Gln
    130                 135                 140

Gln Asn Leu Val Ser Thr Pro Phe Ser Leu Gly Lys Gly Leu Gly Phe
145                 150                 155                 160

Thr Lys Ala Gln Ile Glu Pro Gly Ile Tyr Ala Gln Ser Val Gly Asp
                165                 170                 175

Ala Gly Pro Ala Ser Pro Leu Leu Gly Leu Val Ser Val Leu Asp Arg
            180                 185                 190
```

```
Ala Arg Pro Gly Glu Lys Ile Leu Leu Val Ser Tyr Gly Phe Gly Ala
        195                 200                 205

Gly Ser Asp Ala Ile Ala Leu Thr Val Thr Asp Ala Ile Glu Ala Tyr
        210                 215                 220

Gln Lys Thr Asn Val Ala Leu Arg Thr Leu Leu Glu Asp Lys Tyr Tyr
225                 230                 235                 240

Val Asp Tyr Gly Thr Ser Ile Lys Tyr Glu Phe Lys Tyr Leu Arg Pro
                245                 250                 255

Asp Tyr Ala Leu Thr Ala Tyr Leu
            260
```

(2) INFORMATION FOR SEQ ID NO:7:

(i) SEQUENCE CHARACTERISTICS:
        (A) LENGTH: 708 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pseudomonas fluorescens (ix) FEATURE:
        (A) NAME/KEY: CDS
        (B) LOCATION: complement (1..708)
        (D) OTHER INFORMATION: /note= "phlB DNA sequence. SEQ ID
           NO:8 is translation (protein) of SEQ ID NO:7."

(xi) SEQUENCE DESCRIPTION: SEQ ID NO:7:

```
TTTCGCCAAT ACGAATTTAT AAGCGTATTG CCACGCCAGG TTGCTTTCCC GAACGTGCTT    60
GCGAATAACC ATTCGCACTG GTGCTCCAGT CACGACTTGC CGGGGATCGA CGACATCGAC   120
GATTTCCGAG GCGATCACCA AGCCATCGTC CAGGCGCACC ATTGCCATGA AGCGCGGGAC   180
GGTTTCGCCA TATCCCATGG CCGCGAGAAT GGGGTTTTCA GCATGGGCGC TGACCTGGAT   240
CGTGCCGGTG CGTGCGCAGC GATACGGTTC CACGTTCAAT GAGTTGCATG CGCCGCAGAC   300
GGTGCGCCGT GGGAAGAAGA TTTCTTCGCA ATCCTGGCAG CGGCTGCCTT CGAGACGATA   360
TTTTCCGCCA TGTTCGCGCC ATTCGCGCAA CATGCTGGCG GTGGTCATGC GGTGTATTTG   420
TTCTGGGTAA AGGGACATGG TCGGCTCCTT AATCGTTGGA AAGCACAATG ACGCTGTTAT   480
GCGCGGCGTA ACCGCCCAAG TTCCTGCGAG ACGCCAATGC GAGCGTCCTT GACTTGGTTG   540
TTGGACTCGC CGCGAAGTTG TCGGAACAGC TCGGTAATGT GCAGGATGCC GTCGCAACCA   600
GAGGCGTGGC CGCGGCCAAT ATTGCCGCCA TCGGTGTTTA ATGGCAGTTG CCCGTCGAGG   660
GCTATGCCGC CTTCCAATAC AAAGTCGCCT GCCTGGCCTG GACCACAT              708
```

(2) INFORMATION FOR SEQ ID NO:8:

(i) SEQUENCE CHARACTERISTICS:
        (A) LENGTH: 236 amino acids
        (B) TYPE: amino acid
        (D) TOPOLOGY: linear (ii) MOLECULE TYPE: protein (xi) SEQUENCE DESCRIPTION: SEQ ID NO:8:

```
Met Trp Ser Arg Pro Gly Arg Arg Leu Cys Ile Gly Arg Arg His Ser
 1               5                  10                  15
```

Pro Arg Arg Ala Thr Ala Ile Lys His Arg Trp Arg Gln Tyr Trp Pro
            20                  25                  30

Arg Pro Arg Leu Trp Leu Arg Arg His Pro Ala His Tyr Arg Ala Val
        35                  40                  45

Pro Thr Thr Ser Arg Arg Val Gln Gln Pro Ser Gln Gly Arg Ser His
    50                  55                  60

Trp Arg Leu Ala Gly Thr Trp Ala Val Thr Pro Arg Ile Thr Ala Ser
65                  70                  75                  80

Leu Cys Phe Pro Thr Ile Lys Glu Pro Thr Met Ser Leu Tyr Pro Glu
                85                  90                  95

Gln Ile His Arg Met Thr Thr Ala Ser Met Leu Arg Glu Trp Arg Glu
            100                 105                 110

His Gly Gly Lys Tyr Arg Leu Glu Gly Ser Arg Cys Gln Asp Cys Glu
        115                 120                 125

Glu Ile Phe Phe Pro Arg Arg Thr Val Cys Gly Ala Cys Asn Ser Leu
    130                 135                 140

Asn Val Glu Pro Tyr Arg Cys Ala Arg Thr Gly Thr Ile Gln Val Ser
145                 150                 155                 160

Ala His Ala Glu Asn Pro Ile Leu Ala Ala Met Gly Tyr Gly Glu Thr
                165                 170                 175

Val Pro Arg Phe Met Ala Met Val Arg Leu Asp Asp Gly Leu Val Ile
            180                 185                 190

Ala Ser Glu Ile Val Asp Val Val Asp Pro Arg Gln Val Val Thr Gly
        195                 200                 205

Ala Pro Val Arg Met Val Ile Arg Lys His Val Arg Glu Ser Asn Leu
    210                 215                 220

Ala Trp Gln Tyr Ala Tyr Lys Phe Val Leu Ala Lys
225                 230                 235

(2) INFORMATION FOR SEQ ID NO:9:

(i) SEQUENCE CHARACTERISTICS:
        (A) LENGTH: 1167 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pseudomonas fluorescens (ix) FEATURE:
        (A) NAME/KEY: CDS
        (B) LOCATION: complement (1..1167)
        (D) OTHER INFORMATION: /note= "phlC DNA sequence. SEQ ID
            NO:10 is translation (protein) of SEQ ID NO:9."

(xi) SEQUENCE DESCRIPTION: SEQ ID NO:9:

TGCGCGGCGT AACCGCCCAA GTTCCTGCGA GACGCCAATG CGAGCGTCCT TGACTTGGTT      60

GTTGGACTCG CCGCGAAGTT GTCGGAACAG CTCGGTAATG TGCAGGATGC CGTCGCAACC     120

AGAGGCGTGG CCGCGGCCAA TATTGCCGCC ATCGGTGTTT AATGGCAGTT GCCCGTCGAG     180

GGCTATGCCG CCTTCCAATA CAAAGTCGCC TGCCTGGCCT GGACCACATA CGCCCATGGA     240

TTCCATCTGA ATCAATCCGG CACCCAGCAA GTCGTAGACT TGGGCCACAT CGATATCCTT     300

GGCGGTGATG CCGGCTTTTT TGTAGGCGAT TTCGGCGCAA GCAATGGAGT TGGCGGAAAC     360

-continued

```
CGCCATGCCG ACGTCTTTTG GCAGGCCTGG ATATTTCAGG GTCGGGTTGT GATAGCGCGT    420

CCCGAAATAA TGGGATACGC CGGTATAGGC ACAACCACGG ACGAATACCG GTTGGGTCGT    480

GTAGCGGTGC GCCAGGTGTT CGGCGACCAG GATGGCGCAA CCGCTGGCTT CACCCCAGGC    540

CAGCATCGAG CCACATGCTT CGCTGTTCTT GAGGGTTTCA AGGGATGGCA CCGGCACGCC    600

ATAGCGGGTT GCCGTGGGCG TGTTGTGCGC ATAGATGCGC ATTTGCCGAC CAAACGTTGC    660

CAGGACATCC GCTTCGCGTC CTGCATAGCC AAATTTTTCA AAATATTCGG CGGTTGCGAG    720

GGCAAAGGCG TCGGTGTGCG AAATGCCCAG GAAATAATCG TACTCACATT CGGTACTGGA    780

GCCGATGTAT TCGGCATAGT TGAAGTGGTC GGTCATTTTT TCAAAGCCAC CACACAGGAC    840

GATGTCGTAC TCACCCGAGG CGACCATCTG ATGGGCCATC TGAAAGGAAA CCGAGCTGCT    900

GGTGCAGTTG GCAGTGCTCA TGAACGTCGG GGCAGGGCTG ATGCCCAGGG CATCGGAAAT    960

AGTCGGGCCC AGGCCGCCGT ATTCGGAAAT ACCTTCACCG TGATATCCAT AAGCGACTGC   1020

CTGAAGTTCA CGGGGATGCA TCTTGATGGC GTTGAGCGCC TGATAGGCGG ACTCGACGAT   1080

CATCTCCTTG AAGGTTTGAC GGACTCTGGA GCTGCCGGGT TTGGAAGTAT AGGCAGCCGA   1140

AACGATAGCA ACGCGTCGTG CGCTCAT                                      1167
```

(2) INFORMATION FOR SEQ ID NO:10:

(i) SEQUENCE CHARACTERISTICS:
        (A) LENGTH: 389 amino acids
        (B) TYPE: amino acid
        (D) TOPOLOGY: linear (ii) MOLECULE TYPE: protein (xi) SEQUENCE DESCRIPTION: SEQ ID NO:10:

```
Met Ser Ala Arg Arg Val Ala Ile Val Ser Ala Ala Tyr Thr Ser Lys
 1               5                  10                  15

Pro Gly Ser Ser Arg Val Arg Gln Thr Phe Lys Glu Met Ile Val Glu
            20                  25                  30

Ser Ala Tyr Gln Ala Leu Asn Ala Ile Lys Met His Pro Arg Glu Leu
        35                  40                  45

Gln Ala Val Ala Tyr Gly Tyr His Gly Glu Gly Ile Ser Glu Tyr Gly
    50                  55                  60

Gly Leu Gly Pro Thr Ile Ser Asp Ala Leu Gly Ile Ser Pro Ala Pro
65                  70                  75                  80

Thr Phe Met Ser Thr Ala Asn Cys Thr Ser Ser Val Ser Phe Gln
                85                  90                  95

Met Ala His Gln Met Val Ala Ser Gly Glu Tyr Asp Ile Val Leu Cys
            100                 105                 110

Gly Gly Phe Glu Lys Met Thr Asp His Phe Asn Tyr Ala Glu Tyr Ile
        115                 120                 125

Gly Ser Ser Thr Glu Cys Glu Tyr Asp Tyr Phe Leu Gly Ile Ser His
    130                 135                 140

Thr Asp Ala Phe Ala Leu Ala Thr Ala Glu Tyr Phe Glu Lys Phe Gly
145                 150                 155                 160

Tyr Ala Gly Arg Glu Ala Asp Val Leu Ala Thr Phe Gly Arg Gln Met
                165                 170                 175

Arg Ile Tyr Ala His Asn Thr Pro Thr Ala Thr Arg Tyr Gly Val Pro
            180                 185                 190

Val Pro Ser Leu Glu Thr Leu Lys Asn Ser Glu Ala Cys Gly Ser Met
        195                 200                 205
```

Leu Ala Trp Gly Glu Ala Ser Gly Cys Ala Ile Leu Val Ala Glu His
210                 215                 220

Leu Ala His Arg Tyr Thr Thr Gln Pro Val Phe Val Arg Gly Cys Ala
225                 230                 235                 240

Tyr Thr Gly Val Ser His Tyr Phe Gly Thr Arg Tyr His Asn Pro Thr
            245                 250                 255

Leu Lys Tyr Pro Gly Leu Pro Lys Asp Val Gly Met Ala Val Ser Ala
            260                 265                 270

Asn Ser Ile Ala Cys Ala Glu Ile Ala Tyr Lys Lys Ala Gly Ile Thr
            275                 280                 285

Ala Lys Asp Ile Asp Val Ala Gln Val Tyr Asp Leu Leu Gly Ala Gly
290                 295                 300

Leu Ile Gln Met Glu Ser Met Gly Val Cys Gly Pro Gly Gln Ala Gly
305                 310                 315                 320

Asp Phe Val Leu Glu Gly Gly Ile Ala Leu Asp Gly Gln Leu Pro Leu
            325                 330                 335

Asn Thr Asp Gly Gly Asn Ile Gly Arg Gly His Ala Ser Gly Cys Asp
            340                 345                 350

Gly Ile Leu His Ile Thr Glu Leu Phe Arg Gln Leu Arg Gly Glu Ser
            355                 360                 365

Asn Asn Gln Val Lys Asp Ala Arg Ile Gly Val Ser Gln Glu Leu Gly
370                 375                 380

Arg Leu Arg Arg Ala
385

(2) INFORMATION FOR SEQ ID NO:11:

(i) SEQUENCE CHARACTERISTICS:
        (A) LENGTH: 1047 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pseudomonas fluorescens (ix) FEATURE:
        (A) NAME/KEY: CDS
        (B) LOCATION: complement (1..1047)
        (D) OTHER INFORMATION: /note= "phlD DNA sequence. SEQ ID
            NO:12 is translation (protein) of SEQ ID NO:11."

(xi) SEQUENCE DESCRIPTION: SEQ ID NO:11:

GGCCACCCAC TTGCCCACGG CCATTTCAGC TGTGAAGCCA GGGCCGAAGG CTGCCAGCAT      60

GCCGGTCGCT CCATTGGCCG GCCCGCTGTC GAACTGGCGC TTGAGGACGT CGAAGACCAC     120

CACGCTGGCA ATATTGCCGG CCTCGCTCAA GCTGTCGCGA GACTGCGCGA CCCTGCCAGG    180

TTCCAGATCG AGCTGCAGCA CCAGCTCATC AAGAATTTTT CGTCCACCGG TGTGGAAGAT    240

GAAAAGTCA TTTTGAGCGC AATGTTGGTT GAAGGTCTCG AAGTTCAATT CCTCCATCAT     300

CGGGGCCACG TCTTTAATGG AGTTCATGAC GGCTTTGTCC AGGGTGAAGT GAAAGCCGCT    360

GTCCTTGACG TCATATTTAA TGTAGTGCTC GCTGTCAGGC AGGAAATAAG AGCCGGTTTT    420

GGCGATCTTG AATCCCGGCG CCTTATCGTC GGCGCGCATT ACGCAGGCCG AGACGGCATC    480

GCCGAACAGC GCTGCGGATA TGAACGCGTG CAACTTGGTG TCCTGTGGTT GATAGCAGAG    540

| | |
|---|---:|
| TGACGAGAAC TCCAGCGAGA CAATAAGGGC GTGGTTGTCT GGAGACAGGC TGCCAAAGTC | 600 |
| GTTGGCTCGA TTAATCGCCG CGGCGCCTGC CACGCATCCC AATTGAGCGA TCGGCAATTG | 660 |
| TACGGTCGAC GTTCGCAGTC CCAAGTCATT GATCAGGTGG GCTGTCAGCG ATGGCATCAT | 720 |
| GAACCCGGTG CAAGAGGTAA CGGCGACCAT CCGGATGTCG TCCGTGGTCA AGCCCGCGTT | 780 |
| TTCAATGGCC TGGCGCGCGG CGATTGAAGA CATGCGGCGA GCCTCTCGCT CATACACGAT | 840 |
| GCTGCGGTGG GTAAAGCCGG TATGCACCGC AAGTTCATCG ATGGGCAAGA CCAGATACCG | 900 |
| TTCATTGACT TGGGTGTTTT GAATCATCCG TTTAGCCAAT GCCATGCGCG GATGATCGTC | 960 |
| ATGCAACTGT TCCAAGTGAT CGATCATCTG TTGTTGGGTA ATTTTGTAAT GCGGGAAAAG | 1020 |
| CAAGCTGGGT TTGCAAAGAG TAGACAT | 1047 |

(2) INFORMATION FOR SEQ ID NO:12:

(i) SEQUENCE CHARACTERISTICS:
        (A) LENGTH: 349 amino acids
        (B) TYPE: amino acid
        (D) TOPOLOGY: linear (ii) MOLECULE TYPE: protein (xi) SEQUENCE DESCRIPTION: SEQ ID NO:12:

```
Met Ser Thr Leu Cys Lys Pro Ser Leu Leu Phe Pro His Tyr Lys Ile
  1               5                  10                  15

Thr Gln Gln Met Ile Asp His Leu Glu Gln Leu His Asp Asp His
             20                  25                  30

Pro Arg Met Ala Leu Ala Lys Arg Met Ile Gln Asn Thr Gln Val Asn
         35                  40                  45

Glu Arg Tyr Leu Val Leu Pro Ile Asp Glu Leu Ala Val His Thr Gly
 50                  55                  60

Phe Thr His Arg Ser Ile Val Tyr Glu Arg Glu Ala Arg Arg Met Ser
 65                  70                  75                  80

Ser Ile Ala Ala Arg Gln Ala Ile Glu Asn Ala Gly Leu Thr Thr Asp
                 85                  90                  95

Asp Ile Arg Met Val Ala Val Thr Ser Cys Thr Gly Phe Met Met Pro
            100                 105                 110

Ser Leu Thr Ala His Leu Ile Asn Asp Leu Gly Leu Arg Thr Ser Thr
        115                 120                 125

Val Gln Leu Pro Ile Ala Gln Leu Gly Cys Val Ala Gly Ala Ala Ala
    130                 135                 140

Ile Asn Arg Ala Asn Asp Phe Gly Ser Leu Ser Pro Asp Asn His Ala
145                 150                 155                 160

Leu Ile Val Ser Leu Glu Phe Ser Ser Leu Cys Tyr Gln Pro Gln Asp
                165                 170                 175

Thr Lys Leu His Ala Phe Ile Ser Ala Ala Leu Phe Gly Asp Ala Val
            180                 185                 190

Ser Ala Cys Val Met Arg Ala Asp Asp Lys Ala Pro Gly Phe Lys Ile
        195                 200                 205

Ala Lys Thr Gly Ser Tyr Phe Leu Pro Asp Ser Glu His Tyr Ile Lys
    210                 215                 220

Tyr Asp Val Lys Asp Ser Gly Phe His Phe Thr Leu Asp Lys Ala Val
225                 230                 235                 240

Met Asn Ser Ile Lys Asp Val Ala Pro Met Met Glu Glu Leu Asn Phe
                245                 250                 255

Glu Thr Phe Asn Gln His Cys Ala Gln Asn Asp Phe Phe Ile Phe His
            260                 265                 270
```

```
Thr Gly Gly Arg Lys Ile Leu Asp Glu Leu Val Leu Gln Leu Asp Leu
            275                 280                 285

Glu Pro Gly Arg Val Ala Gln Ser Arg Asp Ser Leu Ser Glu Ala Gly
            290                 295                 300

Asn Ile Ala Ser Val Val Phe Asp Val Leu Lys Arg Gln Phe Asp
305                 310                 315                 320

Ser Gly Pro Ala Asn Gly Ala Thr Gly Met Leu Ala Ala Phe Gly Pro
                325                 330                 335

Gly Phe Thr Ala Glu Met Ala Val Gly Lys Trp Val Ala
            340                 345
```

(2) INFORMATION FOR SEQ ID NO:13:

(i) SEQUENCE CHARACTERISTICS:
  (A) LENGTH: 1269 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (vi) ORIGINAL SOURCE:
  (A) ORGANISM: Pseudomonas fluorescens (ix) FEATURE:
  (A) NAME/KEY: CDS
  (B) LOCATION: complement (1..1269)
  (D) OTHER INFORMATION: /note= "phlE DNA sequence. SEQ ID
   NO:14 is translation (protein) of SEQ ID NO:13."

(xi) SEQUENCE DESCRIPTION: SEQ ID NO:13:

```
CTTATCCTCC AGCGTCAAGC GAGCGGGCAG GGGGCCGTAG TCCGCACGGT CATTGAAAAC      60

AGAGCTGGCT TCCTTGAGCC GCAGGGACAG AAACCCGCCC ATCAAACTAC CAGCCAGTGC     120

CAGAAACAGA ATGGCGGTAA GCCCCCAGTT CACGGCGATG TACCCGGCGA CCACGGGCGC     180

AACGCCACCG CCCAGGATTT CTCCGCAACC CACCACCAGG CCCGTAGCGG TGGCCAGTAA     240

ACTGGGTGGC ACTGATTCGC TGGTCAGTGG GCCGACGGTG ATGCAGATCA GGCTGAAATT     300

GATGAAAGAT AAAAAGAACA GCTGGAGGAA CAGTAGCCAC GGTAACGGCG GGGAAATGAT     360

GAGCAAGCCG ACCAGTAGTG TGCTGATCAG GAAGCAGATG GAAACGACAG GCTTGCGGCC     420

CAGTTGGTCA GACAAACCGG GAATGACGAG CTGGCCGAAA AAACCACCCA GGCCGATCGC     480

GGAGATGATC ATGGCCATGG AGAAATTGCT CAGGTGCAAG ACGTCTGTCA GGTAGCTGGG     540

GAGCAGGGCG CACAGGACGA ATTGGCACGT CAGTATGCAT AGCATCAAGG CAATGTTGAG     600

GCGCACGTTG CCGCTGGACA GGGCTGTTCG CCATTGGCTG CCGGAGGGTT CTACGAGCGG     660

CCTTGGATGG GGCGCCTGGC TCGGTTGGTA GGTTCGATAC AGATACCAGG CCACCAGCAG     720

GCCCGGCAAC GAGATGATGG CGAACACGGC GCGCCACGAT CCGAACATTT CAAACAATAC     780

GCCCGCCAGC AGCGGCCCCA GGCACAGGCC GATGATGGGA AACAGTGCCT GCTGGATGCC     840

CAGGTTGAGC CCGCGTCGGC ACGGCTGCGA AACTTCATCG GTGACAATGA TGCTGACCGG     900

GGTGAAGGCG CCTTCGCAGA TCCCCATCAA GGCGCGCAGG AGCACCAGGC CCATAAGGCT     960

TGAGATCAAC GCAGATGCGC CGGCCAGGAG CGATACCAAG GTAATCGAAA GCACCAGCAG    1020

TTGCTTGGTG CCCAATCGCC TGATAGCAAC GCCCATGAAG AGGGCCGAGC CTCCCCAGGC    1080

AAATGCCAGG ATCGCCGATA ACAGGCCCAG GTCCTGATAG TCCAGGGCCA GGTCATGCAT    1140
```

```
GATCACCGGG AACAACGGCA TGATAATGAA TCGATCAAGT CCTACCAGCC CGAAGCTCAG    1200

CGACAAAAGA ACGACCATGC GTCTTTCGTA GCCACCCCAA GGTCGAGTGG CAAGATACGT    1260

ACTCTCCAT                                                            1269
```

(2) INFORMATION FOR SEQ ID NO:14:

(i) SEQUENCE CHARACTERISTICS:
        (A) LENGTH: 423 amino acids
        (B) TYPE: amino acid
        (D) TOPOLOGY: linear (ii) MOLECULE TYPE: protein (xi) SEQUENCE DESCRIPTION: SEQ ID NO:14:

```
Met Glu Ser Thr Tyr Leu Ala Thr Arg Pro Trp Gly Gly Tyr Glu Arg
 1               5                  10                  15

Arg Met Val Val Leu Leu Ser Leu Ser Phe Gly Leu Val Gly Leu Asp
            20                  25                  30

Arg Phe Ile Ile Met Pro Leu Phe Pro Val Ile Met His Asp Leu Ala
        35                  40                  45

Leu Asp Tyr Gln Asp Leu Gly Leu Leu Ser Ala Ile Leu Ala Phe Ala
    50                  55                  60

Trp Gly Gly Ser Ala Leu Phe Met Gly Val Ala Ile Arg Arg Leu Gly
65                  70                  75                  80

Thr Lys Gln Leu Leu Val Leu Ser Ile Thr Leu Val Ser Leu Leu Ala
                85                  90                  95

Gly Ala Ser Ala Leu Ile Ser Ser Leu Met Gly Leu Val Leu Leu Arg
            100                 105                 110

Ala Leu Met Gly Ile Cys Glu Gly Ala Phe Thr Pro Val Ser Ile Ile
        115                 120                 125

Val Thr Asp Glu Val Ser Gln Pro Cys Arg Arg Gly Leu Asn Leu Gly
    130                 135                 140

Ile Gln Gln Ala Leu Phe Pro Ile Ile Gly Leu Cys Leu Gly Pro Leu
145                 150                 155                 160

Leu Ala Gly Val Leu Phe Glu Met Phe Gly Ser Trp Arg Ala Val Phe
                165                 170                 175

Ala Ile Ile Ser Leu Pro Gly Leu Leu Val Ala Trp Tyr Leu Tyr Arg
            180                 185                 190

Thr Tyr Gln Pro Ser Gln Ala Pro His Pro Arg Pro Leu Val Glu Pro
        195                 200                 205

Ser Gly Ser Gln Trp Arg Thr Ala Leu Ser Ser Gly Asn Val Arg Leu
    210                 215                 220

Asn Ile Ala Leu Met Leu Cys Ile Leu Thr Cys Gln Phe Val Leu Cys
225                 230                 235                 240

Ala Leu Leu Pro Ser Tyr Leu Thr Asp Val Leu His Leu Ser Asn Phe
                245                 250                 255

Ser Met Ala Met Ile Ile Ser Ala Ile Gly Leu Gly Gly Phe Phe Gly
            260                 265                 270

Gln Leu Val Ile Pro Gly Leu Ser Asp Gln Leu Gly Arg Lys Pro Val
        275                 280                 285

Val Ser Ile Cys Phe Leu Ile Ser Thr Leu Leu Val Gly Leu Leu Ile
    290                 295                 300

Ile Ser Pro Pro Leu Pro Trp Leu Leu Phe Leu Gln Leu Phe Phe Leu
305                 310                 315                 320

Ser Phe Ile Asn Phe Ser Leu Ile Cys Ile Thr Val Gly Pro Leu Thr
                325                 330                 335
```

```
Ser Glu Ser Val Pro Pro Ser Leu Leu Ala Thr Ala Thr Gly Leu Val
            340                 345                 350

Val Gly Cys Gly Glu Ile Leu Gly Gly Gly Val Ala Pro Val Val Ala
            355                 360                 365

Gly Tyr Ile Ala Val Asn Trp Gly Leu Thr Ala Ile Leu Phe Leu Ala
            370                 375                 380

Leu Ala Gly Ser Leu Met Gly Gly Phe Leu Ser Leu Arg Leu Lys Glu
385                 390                 395                 400

Ala Ser Ser Val Phe Asn Asp Arg Ala Asp Tyr Gly Pro Leu Pro Ala
            405                 410                 415

Arg Leu Thr Leu Glu Asp Lys
            420
```

(2) INFORMATION FOR SEQ ID NO:15:

(i) SEQUENCE CHARACTERISTICS:
        (A) LENGTH: 606 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pseudomonas fluorescens (ix) FEATURE:
        (A) NAME/KEY: CDS
        (B) LOCATION: 1..606
        (D) OTHER INFORMATION: /note= "phlF DNA sequence. SEQ ID
            NO:16 is translation (protein) of SEQ ID NO:15."

(xi) SEQUENCE DESCRIPTION: SEQ ID NO:15:

```
ATG GCC CGT AAA CCG TCT CGG AGC TCC ATT GGC TCA TTG AGG AGC CCA        48
Met Ala Arg Lys Pro Ser Arg Ser Ser Ile Gly Ser Leu Arg Ser Pro
1               5                   10                  15

CAT ACG CAC AAA GCG ATC ATC ATC TCC GCT ATA GAA ACA CTC AAG GAG        96
His Thr His Lys Ala Ile Ile Ile Ser Ala Ile Glu Thr Leu Lys Glu
                20                  25                  30

TGC GGT TAT TCA GGG TTG AGT ATC GAG GCT GTG GCT CGC CGT GCC GGC       144
Cys Gly Tyr Ser Gly Leu Ser Ile Glu Ala Val Ala Arg Arg Ala Gly
            35                  40                  45

GCG AGC AAG CCG ACC ATC TAT CGA TGG TGG GGT AAC AAG GCG GCT TTG       192
Ala Ser Lys Pro Thr Ile Tyr Arg Trp Trp Gly Asn Lys Ala Ala Leu
    50                  55                  60

ATC GCC GAA GTC TAC GAG AGC GAA AGC GAG CAG ATT CGC AAG GAG CCT       240
Ile Ala Glu Val Tyr Glu Ser Glu Ser Glu Gln Ile Arg Lys Glu Pro
65                  70                  75                  80

GAT AAA GGA TCC TTC AAG GAG AAC CTC AAT TTC CTG CTG CTC AAT CTG       288
Asp Lys Gly Ser Phe Lys Glu Asn Leu Asn Phe Leu Leu Leu Asn Leu
                85                  90                  95

TGG AAG GTC TGG AGA GAA ACG ATT TGC GGG GAG GCG TTT CGG TGT GTC       336
Trp Lys Val Trp Arg Glu Thr Ile Cys Gly Glu Ala Phe Arg Cys Val
            100                 105                 110

ATC GCT GAA GCC CAG CTC GAC CCC AGT ACG CTG CCC AAG CTG AAG GAT       384
Ile Ala Glu Ala Gln Leu Asp Pro Ser Thr Leu Pro Lys Leu Lys Asp
        115                 120                 125

GAA TTC ATG GAG CGT CGT CGG GAA TTG CCG CGA AAG CTG GTG GAA AAC       432
Glu Phe Met Glu Arg Arg Arg Glu Leu Pro Arg Lys Leu Val Glu Asn
130                 135                 140
```

```
GCC ATC CAG CAA GGT GAG TTG CCC AAG GAC ACG TCC CGT GAG TTG TTG      480
Ala Ile Gln Gln Gly Glu Leu Pro Lys Asp Thr Ser Arg Glu Leu Leu
145                 150                 155                 160

TTG GAC ATG ATC TTC GGA TTT TGC TGG TAC AGG CTG TTG ACT GAG CAA      528
Leu Asp Met Ile Phe Gly Phe Cys Trp Tyr Arg Leu Leu Thr Glu Gln
                165                 170                 175

CTG GAA GTG GAG GGT GAC ATC AAT GAA TTC ACG ACG CTT CTG TTG AAC      576
Leu Glu Val Glu Gly Asp Ile Asn Glu Phe Thr Thr Leu Leu Leu Asn
            180                 185                 190

GGC GTG TTG CGT ACG ACT TCG GCG GCG GAG                              606
Gly Val Leu Arg Thr Thr Ser Ala Ala Glu
        195                 200
```

(2) INFORMATION FOR SEQ ID NO:16:

(i) SEQUENCE CHARACTERISTICS:
        (A) LENGTH: 202 amino acids
        (B) TYPE: amino acid
        (D) TOPOLOGY: linear (ii) MOLECULE TYPE: protein (xi) SEQUENCE DESCRIPTION: SEQ ID NO:16:

```
Met Ala Arg Lys Pro Ser Arg Ser Ser Ile Gly Ser Leu Arg Ser Pro
1               5                   10                  15

His Thr His Lys Ala Ile Ile Ile Ser Ala Ile Glu Thr Leu Lys Glu
                20                  25                  30

Cys Gly Tyr Ser Gly Leu Ser Ile Glu Ala Val Ala Arg Arg Ala Gly
            35                  40                  45

Ala Ser Lys Pro Thr Ile Tyr Arg Trp Trp Gly Asn Lys Ala Ala Leu
        50                  55                  60

Ile Ala Glu Val Tyr Glu Ser Glu Ser Glu Gln Ile Arg Lys Glu Pro
65                  70                  75                  80

Asp Lys Gly Ser Phe Lys Glu Asn Leu Asn Phe Leu Leu Leu Asn Leu
                85                  90                  95

Trp Lys Val Trp Arg Glu Thr Ile Cys Gly Glu Ala Phe Arg Cys Val
                100                 105                 110

Ile Ala Glu Ala Gln Leu Asp Pro Ser Thr Leu Pro Lys Leu Lys Asp
            115                 120                 125

Glu Phe Met Glu Arg Arg Arg Glu Leu Pro Arg Lys Leu Val Glu Asn
        130                 135                 140

Ala Ile Gln Gln Gly Glu Leu Pro Lys Asp Thr Ser Arg Glu Leu Leu
145                 150                 155                 160

Leu Asp Met Ile Phe Gly Phe Cys Trp Tyr Arg Leu Leu Thr Glu Gln
                165                 170                 175

Leu Glu Val Glu Gly Asp Ile Asn Glu Phe Thr Thr Leu Leu Leu Asn
            180                 185                 190

Gly Val Leu Arg Thr Thr Ser Ala Ala Glu
        195                 200
```

(2) INFORMATION FOR SEQ ID NO:17:

(i) SEQUENCE CHARACTERISTICS:
        (A) LENGTH: 1254 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO

-continued (iv) ANTI-SENSE: NO (vi) ORIGINAL SOURCE:
    (A) ORGANISM: Pseudomonas fluorescens (ix) FEATURE:
    (A) NAME/KEY: CDS
    (B) LOCATION: 1..1254
    (D) OTHER INFORMATION: /note= "phlR DNA sequence.  SEQ ID
        NO:18 is translation (protein) of SEQ ID NO:17."

(xi) SEQUENCE DESCRIPTION: SEQ ID NO:17:

| | | | | | | | | | | | | | | | | |
|---|---|---|---|---|---|---|---|---|---|---|---|---|---|---|---|---|
| ATG | GGA | TAC | GCC | GGT | ATA | GGC | ACA | ACC | ACG | GAC | GAA | TAC | CGG | TTG | GGT | 48 |
| Met | Gly | Tyr | Ala | Gly | Ile | Gly | Thr | Thr | Thr | Asp | Glu | Tyr | Arg | Leu | Gly | |
| 1 | | | | 5 | | | | | 10 | | | | | 15 | | |
| CGT | GTA | GCG | GTG | CGC | CAG | GTG | TTC | GGC | GAC | CAG | GAT | GGC | GCA | ACC | GCT | 96 |
| Arg | Val | Ala | Val | Arg | Gln | Val | Phe | Gly | Asp | Gln | Asp | Gly | Ala | Thr | Ala | |
| | | | 20 | | | | | 25 | | | | | 30 | | | |
| GGC | TTC | ACC | CCA | GGC | CAG | CAT | CGA | GCC | ACA | TGC | TTC | GCT | GTT | CTT | GAG | 144 |
| Gly | Phe | Thr | Pro | Gly | Gln | His | Arg | Ala | Thr | Cys | Phe | Ala | Val | Leu | Glu | |
| | | 35 | | | | | 40 | | | | | 45 | | | | |
| GGT | TTC | AAG | GGA | TGG | CAC | CGG | CAC | GCC | ATA | GCG | GGT | TGC | CGT | GGG | CGT | 192 |
| Gly | Phe | Lys | Gly | Trp | His | Arg | His | Ala | Ile | Ala | Gly | Cys | Arg | Gly | Arg | |
| | 50 | | | | | 55 | | | | | 60 | | | | | |
| GTT | GTG | CGC | ATA | GAT | GCG | CAT | TTG | CCG | ACC | AAA | CGT | TGC | CAG | GAC | ATC | 240 |
| Val | Val | Arg | Ile | Asp | Ala | His | Leu | Pro | Thr | Lys | Arg | Cys | Gln | Asp | Ile | |
| 65 | | | | | 70 | | | | | 75 | | | | | 80 | |
| CGC | TTC | GCG | TCC | TGC | ATA | GCC | AAA | TTT | TTC | AAA | ATA | TTC | GGC | GGT | TGC | 288 |
| Arg | Phe | Ala | Ser | Cys | Ile | Ala | Lys | Phe | Phe | Lys | Ile | Phe | Gly | Gly | Cys | |
| | | | | 85 | | | | | 90 | | | | | 95 | | |
| GAG | GGC | AAA | GGC | GTC | GGT | GTG | CGA | AAT | GCC | CAG | GAA | ATA | ATC | GTA | CTC | 336 |
| Glu | Gly | Lys | Gly | Val | Gly | Val | Arg | Asn | Ala | Gln | Glu | Ile | Ile | Val | Leu | |
| | | | 100 | | | | | 105 | | | | | 110 | | | |
| ACA | TTC | GGT | ACT | GGA | GCC | GAT | GTA | TTC | GGC | ATA | GTT | GAA | GTG | GTC | GGT | 384 |
| Thr | Phe | Gly | Thr | Gly | Ala | Asp | Val | Phe | Gly | Ile | Val | Glu | Val | Val | Gly | |
| | | | 115 | | | | | 120 | | | | | 125 | | | |
| CAT | TTT | TTC | AAA | GCC | ACC | ACA | CAG | GAC | GAT | GTC | GTA | CTC | ACC | CGA | GGC | 432 |
| His | Phe | Phe | Lys | Ala | Thr | Thr | Gln | Asp | Asp | Val | Val | Leu | Thr | Arg | Gly | |
| | 130 | | | | | 135 | | | | | 140 | | | | | |
| GAC | CAT | CTG | ATG | GGC | CAT | CTG | AAA | GGA | AAC | CGA | GCT | GCT | GGT | GCA | GTT | 480 |
| Asp | His | Leu | Met | Gly | His | Leu | Lys | Gly | Asn | Arg | Ala | Ala | Gly | Ala | Val | |
| 145 | | | | | 150 | | | | | 155 | | | | | 160 | |
| GGC | AGT | GCT | CAT | GAA | CGT | CGG | GGC | AGG | GCT | GAT | GCC | CAG | GGC | ATC | GGA | 528 |
| Gly | Ser | Ala | His | Glu | Arg | Arg | Gly | Arg | Ala | Asp | Ala | Gln | Gly | Ile | Gly | |
| | | | | 165 | | | | | 170 | | | | | 175 | | |
| AAT | AGT | CGG | GCC | CAG | GCC | GCC | GTA | TTC | GGA | AAT | ACC | TTC | ACC | GTG | ATA | 576 |
| Asn | Ser | Arg | Ala | Gln | Ala | Ala | Val | Phe | Gly | Asn | Thr | Phe | Thr | Val | Ile | |
| | | | 180 | | | | | 185 | | | | | 190 | | | |
| TCC | ATA | AGC | GAC | TGC | CTG | AAG | TTC | ACG | GGG | ATG | CAT | CTT | GAT | GGC | GTT | 624 |
| Ser | Ile | Ser | Asp | Cys | Leu | Lys | Phe | Thr | Gly | Met | His | Leu | Asp | Gly | Val | |
| | | 195 | | | | | 200 | | | | | 205 | | | | |
| GAG | CGC | CTG | ATA | GGC | GGA | CTC | GAC | GAT | CAT | CTC | CTT | GAA | GGT | TTG | ACG | 672 |
| Glu | Arg | Leu | Ile | Gly | Gly | Leu | Asp | Asp | His | Leu | Leu | Glu | Gly | Leu | Thr | |
| | 210 | | | | | 215 | | | | | 220 | | | | | |
| GAC | TCT | GGA | GCT | GCC | GGG | TTT | GGA | AGT | ATA | GGC | AGC | CGA | AAC | GAT | AGC | 720 |
| Asp | Ser | Gly | Ala | Ala | Gly | Phe | Gly | Ser | Ile | Gly | Ser | Arg | Asn | Asp | Ser | |
| 225 | | | | | 230 | | | | | 235 | | | | | 240 | |
| AAC | GCG | TCG | TGC | GCT | CAT | TGG | AAG | TGC | TCC | TTG | CTG | GAT | GGT | TGG | GAA | 768 |
| Asn | Ala | Ser | Cys | Ala | His | Trp | Lys | Cys | Ser | Leu | Leu | Asp | Gly | Trp | Glu | |
| | | | | 245 | | | | | 250 | | | | | 255 | | |
| TCA | GAG | GTA | GGC | TGT | CAG | GGC | GTA | GTC | AGG | CCG | CAA | GTA | TTT | GAA | CTC | 816 |
| Ser | Glu | Val | Gly | Cys | Gln | Gly | Val | Val | Arg | Pro | Gln | Val | Phe | Glu | Leu | |

```
GTA CTT GAT CGA CGT CCC GTA ATC CAC GTA ATA CTT GTC TTC CAG CAG      864
Val Leu Asp Arg Arg Pro Val Ile His Val Ile Leu Val Phe Gln Gln
        275                 280                 285

CGT GCG CAG CGC AAC GTT GGT CTT TTG GTA GGC TTC GAT GGC ATC GGT      912
Arg Ala Gln Arg Asn Val Gly Leu Leu Val Gly Phe Asp Gly Ile Gly
        290                 295                 300

CAC TGT CAA CGC AAT CGC ATC GCT GCC CGC ACC AAA CCC GTA CGA CAC      960
His Cys Gln Arg Asn Arg Ile Ala Ala Arg Thr Lys Pro Val Arg His
305                 310                 315                 320

CAA GAG GAT TTT TTC ACC CGG ACG CGC TCG GTC CAG TAC GCT CAC CAA     1008
Gln Glu Asp Phe Phe Thr Arg Thr Arg Ser Val Gln Tyr Ala His Gln
                325                 330                 335

GCC CAG CAA CGG ACT CGC GGG CCC CGC ATC ACC GAC ACT CTG GGC ATA     1056
Ala Gln Gln Arg Thr Arg Gly Pro Arg Ile Thr Asp Thr Leu Gly Ile
        340                 345                 350

AAT GCC AGG TTC GAT CTG CGC TTT GGT GAA GCC CAG GCC TTT GCC AAG     1104
Asn Ala Arg Phe Asp Leu Arg Phe Gly Glu Ala Gln Ala Phe Ala Lys
        355                 360                 365

AGA GAA GGG GGT CGA AAC CAG GTT TTG CTG GAA TAC GAC ATA GTC GAA     1152
Arg Glu Gly Gly Arg Asn Gln Val Leu Leu Glu Tyr Asp Ile Val Glu
370                 375                 380

ATC GCT GGC CTG TAC ATT CAT CTT GGC CAT CAA TCC CGA CGC AGC ACG     1200
Ile Ala Gly Leu Tyr Ile His Leu Gly His Gln Ser Arg Arg Ser Thr
385                 390                 395                 400

ATG GGT CTG GTC TTC AAG GCC AAT GCT GTT CTT GTC GGA GCC CAG CCC     1248
Met Gly Leu Val Phe Lys Ala Asn Ala Val Leu Val Gly Ala Gln Pro
                405                 410                 415

CAT TCC                                                              1254
His Ser
```

(2) INFORMATION FOR SEQ ID NO:18:

(i) SEQUENCE CHARACTERISTICS:
        (A) LENGTH: 418 amino acids
        (B) TYPE: amino acid
        (D) TOPOLOGY: linear (ii) MOLECULE TYPE: protein (xi) SEQUENCE DESCRIPTION: SEQ ID NO:18:

```
Met Gly Tyr Ala Gly Ile Gly Thr Thr Thr Asp Glu Tyr Arg Leu Gly
1               5                   10                  15

Arg Val Ala Val Arg Gln Val Phe Gly Asp Gln Asp Gly Ala Thr Ala
                20                  25                  30

Gly Phe Thr Pro Gly Gln His Arg Ala Thr Cys Phe Ala Val Leu Glu
            35                  40                  45

Gly Phe Lys Gly Trp His Arg His Ala Ile Ala Gly Cys Arg Gly Arg
        50                  55                  60

Val Val Arg Ile Asp Ala His Leu Pro Thr Lys Arg Cys Gln Asp Ile
65                  70                  75                  80

Arg Phe Ala Ser Cys Ile Ala Lys Phe Phe Lys Ile Phe Gly Gly Cys
                85                  90                  95

Glu Gly Lys Gly Val Gly Val Arg Asn Ala Gln Glu Ile Ile Val Leu
                100                 105                 110

Thr Phe Gly Thr Gly Ala Asp Val Phe Gly Ile Val Glu Val Val Gly
            115                 120                 125

His Phe Phe Lys Ala Thr Thr Gln Asp Asp Val Val Leu Thr Arg Gly
        130                 135                 140
```

Asp His Leu Met Gly His Leu Lys Gly Asn Arg Ala Ala Gly Ala Val
145                 150                 155                 160

Gly Ser Ala His Glu Arg Arg Gly Arg Ala Asp Ala Gln Gly Ile Gly
                165                 170                 175

Asn Ser Arg Ala Gln Ala Ala Val Phe Gly Asn Thr Phe Thr Val Ile
            180                 185                 190

Ser Ile Ser Asp Cys Leu Lys Phe Thr Gly Met His Leu Asp Gly Val
        195                 200                 205

Glu Arg Leu Ile Gly Gly Leu Asp Asp His Leu Leu Glu Gly Leu Thr
    210                 215                 220

Asp Ser Gly Ala Ala Gly Phe Gly Ser Ile Gly Ser Arg Asn Asp Ser
225                 230                 235                 240

Asn Ala Ser Cys Ala His Trp Lys Cys Ser Leu Leu Asp Gly Trp Glu
                245                 250                 255

Ser Glu Val Gly Cys Gln Gly Val Val Arg Pro Gln Val Phe Glu Leu
                260                 265                 270

Val Leu Asp Arg Arg Pro Val Ile His Val Ile Leu Val Phe Gln Gln
            275                 280                 285

Arg Ala Gln Arg Asn Val Gly Leu Leu Val Gly Phe Asp Gly Ile Gly
290                 295                 300

His Cys Gln Arg Asn Arg Ile Ala Ala Arg Thr Lys Pro Val Arg His
305                 310                 315                 320

Gln Glu Asp Phe Phe Thr Arg Thr Arg Ser Val Gln Tyr Ala His Gln
                325                 330                 335

Ala Gln Gln Arg Thr Arg Gly Pro Arg Ile Thr Asp Thr Leu Gly Ile
                340                 345                 350

Asn Ala Arg Phe Asp Leu Arg Phe Gly Glu Ala Gln Ala Phe Ala Lys
            355                 360                 365

Arg Glu Gly Gly Arg Asn Gln Val Leu Leu Glu Tyr Asp Ile Val Glu
370                 375                 380

Ile Ala Gly Leu Tyr Ile His Leu Gly His Gln Ser Arg Arg Ser Thr
385                 390                 395                 400

Met Gly Leu Val Phe Lys Ala Asn Ala Val Leu Val Gly Ala Gln Pro
                405                 410                 415

His Ser (2) INFORMATION FOR SEQ ID NO:19:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pseudomonas fluorescens (ix) FEATURE:
        (A) NAME/KEY: CDS
        (B) LOCATION: 1..390
        (D) OTHER INFORMATION: /note= "phlF, truncated, DNA
            sequence. SEQ ID NO:20 is translation (protein)
            of SEQ ID NO:19. "

(xi) SEQUENCE DESCRIPTION: SEQ ID NO:19:

```
ATG GCC CGT AAA CCG TCT CGG AGC TCC ATT GGC TCA TTG AGG AGC CCA          48
Met Ala Arg Lys Pro Ser Arg Ser Ser Ile Gly Ser Leu Arg Ser Pro
  1               5                  10                  15

CAT ACG CAC AAA GCG ATC ATC ATC TCC GCT ATA GAA ACA CTC AAG GAG          96
His Thr His Lys Ala Ile Ile Ile Ser Ala Ile Glu Thr Leu Lys Glu
                 20                  25                  30

TGC GGT TAT TCA GGG TTG AGT ATC GAG GCT GTG GCT CGC CGT GCC GGC         144
Cys Gly Tyr Ser Gly Leu Ser Ile Glu Ala Val Ala Arg Arg Ala Gly
             35                  40                  45

GCG AGC AAG CCG ACC ATC TAT CGA TGG TGG GGT AAC AAG GCG GCT TTG         192
Ala Ser Lys Pro Thr Ile Tyr Arg Trp Trp Gly Asn Lys Ala Ala Leu
         50                  55                  60

ATC GCC GAA GTC TAC GAG AGC GAA AGC GAG CAG ATT CGC AAG GAG CCT         240
Ile Ala Glu Val Tyr Glu Ser Glu Ser Glu Gln Ile Arg Lys Glu Pro
 65                  70                  75                  80

GAT AAA GGA TCC TTC AAG GAG AAC CTC AAT TTC CTG CTG CTC AAT CTG         288
Asp Lys Gly Ser Phe Lys Glu Asn Leu Asn Phe Leu Leu Leu Asn Leu
                 85                  90                  95

TGG AAG GTC TGG AGA GAA ACG ATT TGC GGG GAG GCG TTT CGG TGT GTC         336
Trp Lys Val Trp Arg Glu Thr Ile Cys Gly Glu Ala Phe Arg Cys Val
             100                 105                 110

ATC GCT GAA GCC CAG CTC GAC CCC AGT ACG CTG CCC AAG CTG AAG GAT         384
Ile Ala Glu Ala Gln Leu Asp Pro Ser Thr Leu Pro Lys Leu Lys Asp
         115                 120                 125

GAA TTC                                                                 390
Glu Phe
    130

(2) INFORMATION FOR SEQ ID NO:20:

(i) SEQUENCE CHARACTERISTICS:
        (A) LENGTH: 130 amino acids
        (B) TYPE: amino acid
        (D) TOPOLOGY: linear (ii) MOLECULE TYPE: protein (xi) SEQUENCE DESCRIPTION: SEQ ID NO:20:

Met Ala Arg Lys Pro Ser Arg Ser Ser Ile Gly Ser Leu Arg Ser Pro
  1               5                  10                  15

His Thr His Lys Ala Ile Ile Ile Ser Ala Ile Glu Thr Leu Lys Glu
                 20                  25                  30

Cys Gly Tyr Ser Gly Leu Ser Ile Glu Ala Val Ala Arg Arg Ala Gly
             35                  40                  45

Ala Ser Lys Pro Thr Ile Tyr Arg Trp Trp Gly Asn Lys Ala Ala Leu
         50                  55                  60

Ile Ala Glu Val Tyr Glu Ser Glu Ser Glu Gln Ile Arg Lys Glu Pro
 65                  70                  75                  80

Asp Lys Gly Ser Phe Lys Glu Asn Leu Asn Phe Leu Leu Leu Asn Leu
                 85                  90                  95

Trp Lys Val Trp Arg Glu Thr Ile Cys Gly Glu Ala Phe Arg Cys Val
             100                 105                 110

Ile Ala Glu Ala Gln Leu Asp Pro Ser Thr Leu Pro Lys Leu Lys Asp
         115                 120                 125

Glu Phe
    130
```

SEQUENCES FOR PRODUCTION OF 2,4-DIACETYLPHLOROGLUCINOL AND METHODS

FIELD OF THE INVENTION

The present invention relates to materials and methods for improved control of plant pathogens. More particularly, the present invention relates to the identification, isolation, cloning, and sequencing of genetic elements which confer or enhance the ability of an organism to produce the antibiotic 2,4-diacetylphloroglucinol, and uses thereof, particularly the use to transform an organism to introduce or enhance 2,4-diacetylphloroglucinol biosynthetic capability.

BACKGROUND OF THE INVENTION

Rhizobacteria are plant-associated bacteria, derived from many genera, that have the ability to colonize roots aggressively (Schroth and Hancock, Ann. Rev. *Microbiol.* 35:453–576 (1981)). Plant growth-promoting rhizobacteria (PGPR) also are able to improve plant growth either through direct effects on the plant (Lugtenberg et al., *Curr. Opin. Biotechnol.* 2:457–464 (1991)) or by suppressing soilborne plant pathogens (O'Sullivan and O'Gara, *Microbiol. Rev.* 56:662–676 (1992); Weller, *Ann. Rev. Phytopathol.* 26:379–407 (1988)). PGPR when applied to soil, seeds or seed pieces, colonize the surface or inside of roots and channels in the rhizosphere that allow physical access to the root. Thus, they are ideally positioned to limit the establishment or spread of pathogens on the roots.

Bacteria introduced for the purpose of suppressing soilborne plant pathogens may interact with pathogens directly through one or more mechanisms of antagonism including competition, parasitism and predation, and antibiosis, or they may function indirectly to limit the initiation or spread of disease by triggering systemic defense responses in the host plant. It has become increasingly clear over the past decade that antibiosis, the inhibition or destruction of one organism by a metabolic product of another, has a dominant role in the control of several important fungal root and seed pathogens by bacterial biocontrol agents, and especially by fluorescent Pseudomonas species (Weller and Thomashow, pp. 173–180 in *Pest Management: Biologically Based Technologies*, R. D. Lumsden and J. L. Vaughn, eds. (1993)).

Pseudomonas is one of comparatively few bacterial genera capable of synthesizing an array of compounds with broad-spectrum antibiotic activity, and many of the most efficient bacterial biocontrol agents are fluorescent Pseudomonas strains. Antibiotics produced by strains of fluorescent Pseudomonas spp. with biocontrol activity include pyoluteorin and pyrrolnitrin, implicated in control of damping-off diseases of cotton caused by *Pythium ultimum* and *Rhizoctonia solani* (Howell et al., *Phytopathology* 69:480–482 (1979) and Phytopathology 70:712–715 (1980)); oomycin A, also involved in suppression of damping-off of cotton caused by *P. ultimum* (Gutterson, Crit. Rev. Biotechnol. 10:69–91 (1990)); 2,4-diacetylphloroglucinol, involved in control of take-all disease of wheat caused by *Gaeumannomyces graminis* var. *tritici* (Harrison et al., Soil Biol. Biochem. 25:215–221 (1993); Keel et al., *Mol. Plant-Microbe Interact.* 5:4–13 (1992); Vincent et al., *Appl. Environ. Microbiol.* 57:2928–2934 (1991)); and phenazine-1-carboxylic acid and its derivatives, active in suppression of take-all (Thomashow et al., *J. Bacteriol.* 170:3499–3508 (1988); Pierson et al., *Mol. Plant-Microbe Interact.* 5:330–339 (1992)). Of these pathogens, *Gaeumannomyces graminis* and Rhizoctonia species are particularly problematic because there are no satisfactory seed treatments for their control. Rhizoctonia and Pythium species are important because they can infect and causing damping-off and root rot diseases in a wide variety of crop plants. For these reasons, biocontrol agents active against these pathogens are of substantial interest to agriculture.

Whereas most individual biocontrol agents function acceptably only within fairly limited circumstances, biologically active plant-associated microorganisms in the aggregate have almost unlimited genetic biodiversity and are adapted to a wide range of environments. Thus, biocontrol agents that can both antagonize plant pathogens and compete successfully with the indigenous rhizosphere microflora of diverse crops or agroecosystems, are desirable. One proposed approach to obtain such biocontrol agents is to identify genetic elements that can confer or enhance the antifungal activities of rhizosphere colonists indigenous to and highly competitive in the plant and ecological environments where biological control is needed, and use these elements to genetically engineer strains of biocontrol agents. It is preferred that the biocontrol agents combine the ability to control the growth of one or more fungal pathogens with other desirable attributes such as adaptation to a particular host plant or environment or the ability to rapidly achieve peak growth rates.

The antibiotic 2,4-diacetylphloroglucinol (Phl) is a phenolic compound of possible polyketide origin with antifungal, antibacterial, antiviral, antihelminthic and phytotoxic properties. Phl is produced by fluorescent pseudomonads that suppress root diseases caused by a variety of soilborne plant pathogens of crops around the world. These include root rot of wheat caused by *Fusarium oxysporum*, black root rot of tobacco caused by *Thielaviopsis basicola* (Keel et al., *Symbiosis* 9:327–341 (1990); damping-off of sugar beet caused by Pythium ultimum (Fenton et al., *Appl. Environ. Microbiol.* 58:3873–3878 (1992)); damping-off of cotton caused by *P. ultimum* and *Rhizoctonia solani* (Kraus et al., *Phytopathology* 82:264–271 (1992)), blotch of wheat caused by *Septoria tritici* (Levy et al., *Plant Pathol.* 41:335–341 (1992)), and take-all of wheat caused by *Gaeumannomyces graminis* (Harrison et al., supra; Keel et al., (1992) supra; Vincent et al., supra). Strains that produce Phl therefore have considerable agricultural significance.

Three classes of DNA clones have been reported to affect Phl production. The first class contains genes including gacA (Laville et al., *Proc. Natl. Acad. Sci. USA* 89:1562–1566 (1992)), lemA (PCT Application WO 94/01561; Corbell et al., *Mol. Ecol.* 3:608 (1994)) and rpoS (Sarniguet et al., *Mol. Ecol.* 3:607 (1994)), the products of which function as global regulators of a variety of secondary metabolic pathways including that for the synthesis of Phl, thereby indirectly influencing Phl production.

The second class includes DNA sequences of unknown function encoded on the plasmids pME3128 (Keel et al., 1992, supra) and pME3090 (Maurhofer et al., *Phytopathology* 82:190–195 (1992)) from strain CHA0. The former complemented the Tn5 Phl⁻ mutant CHA625 to Phl⁺ and the latter was selected for its ability to cause overproduction of pyoluteorin when introduced into wild-type CHA0; it subsequently was found also to increase Phl production by about 50%. Neither of these loci has been implicated directly in Phl synthesis, nor reported to be able to confer Phl production to strains deficient in this capacity.

A third class of DNA sequences known to influence Phl production includes those reported by Vincent et al., supra;

Fenton et al., supra, and Hara, et al. (Hara et al., pp. 247–249 in *Improving Plant Productivity with Rhizobacteria*, Ryder, Stephens and Bowen, eds. (1994)) that are capable of transferring Phl biosynthetic capability. Vincent et al., supra, described a locus from *P. fluorescens* (formerly aureofaciens) Q2-87 (Pierson and Weller, *Phytopathology* 84:940–947 (1994)) that, when disrupted with the transposon Tn5, resulted in the mutant Q2-87::Tn5-1, which was unable to synthesize Phl. Either of two cosmid clones designated pMON5117 and pMON5118 and isolated from genomic DNA of strain Q2-87 restored antifungal activity and Phl production to Q2-87::Tn5-1.

Mobilization of pMON5118 into two Phl-nonproducing strains conferred the ability to synthesize Phl and increased their antagonistic activity in vitro against *Gaeumannomyces graminis*, *Pythium ultimum*, and *Rhizoctonia solani*. Vincent et al. did not provide any information as to whether a particular portion of the cloned fragment was required, or if the transferred sequences functioned indirectly as a global regulator or specifically to encode enzymes that catalyze the synthesis of Phl.

Fenton et al., supra, reported that pCU203, containing a 6-kb fragment of DNA cloned from *P. fluorescens* F1 13, partially restored Phl production to a Phl⁻ Tn5 mutant of F113 and transferred Phl biosynthetic capability only to Ml 14, one of eight nonproducer strains into which it was introduced. Strains F113(pCU203) and M114(pCU203) were more inhibitory to *P. ultimum* in vitro and increased sugarbeet seedling emergence in soil relative to the parental strains. The 6-kb fragment carried monoacetylphlorogluciol transacetylase activity (Shanahan et al., *Anal. Chem.* 272:271–277 (1993)). Fenton et al. did not indicate that a particular portion of the cloned fragment was required, or if the transferred sequences functioned indirectly as a global regulator or specifically to encode enzymes that catalyze the synthesis of Phl. Shanahan et al. likewise did not specify what portion of the 6-kb fragment was required for the transacetylase reaction, nor did they indicate or suggest that the fragment contains genetic information sufficient to encode the full complement of enzymes required to catalyze Phl biosynthesis. Neither Shanahan et al. nor Fenton et al. have demonstrated that the transacetylase activity is required for or participates in the Phl biosynthetic pathway in F113.

Hara et al., supra, reported that all of eight strains of Phl-nonproducing strains of fluorescent Pseudomonas spp., when transformed with the plasmid pPHL5122 containing a 7-kb fragment of DNA from Q2-87, produced Phl, and that the overall severity of take-all was reduced on seedlings of wheat treated with strains that contained the cloned Phl locus as compared to those treated with unmodified parental strains. Hara et al. did not indicate whether a particular portion of the cloned fragment was required, or suggest any particular biological function, e.g., catalytic or regulatory, for the transferred sequences.

SUMMARY OF THE INVENTION

The present invention comprises DNA sequences in isolated and purified form which function specifically in the biosynthesis of 2,4-diacetylphloroglucinol (Phl) and which can effect the production of 2,4-diacetylphloroglucinol (Phl). By effecting production of Phl, is meant that, a DNA sequence of the invention (1) is capable of conferring the ability to produce Phl in a Phl-nonproducing bacterial strain transformed with the sequence; (2) is capable of enhancing Phl production in a Phl-producing bacterial strain transformed with the sequence, or (3) is capable of both conferring and enhancing Phl production.

In effecting production of Phl, a sequence of the invention may function in the biosynthesis of Phl, the regulation of the biosynthesis of Phl, the export of Phl from the producing cell, the modulation of Phl production or activity, or all of the foregoing. Sequences which function specifically in the biosynthesis of Phl include those encoding catalytic enzymes and regulatory proteins specific for the Phl biosynthetic pathway, proteins that export Phl, and sequences that modulate Phl production or activity.

The genetic elements containing the Phl locus are illustrated in FIG. 1, and the sequence data are given in SEQ ID NO: 3. As discussed in detail below, biosynthetic, bioregulator, export, and modulator elements are contained within the locus. The present invention also encompasses sequences shorter than SEQ. ID NO:3 which have the ability to effect Phl production.

The present invention further comprises DNA sequences in isolated and purified form for phlA, phlB, phlC, phlD, phlE, phlF, and phlR genes, which genes function in the production of Phl. The aforenamed genes encode proteins, which proteins function in the production (synthesis, regulation of synthesis or modulation) of Phl in bacteria. Genomic sequences encoding particular phl gene biosynthetic proteins are specifically exemplified herein. DNA sequences which hybridize specifically to phl biosynthetic gene coding sequences or to their components under standard conditions and which encode phl gene proteins which function in the biosynthesis of Phl are also encompassed by the present invention.

DNA sequences which function to regulate the biosynthesis of Phl include regulatory and coding sequences which influence expression of the Phl biosynthetic sequences and Phl biosynthetic capability. In particular, a DNA sequence is described which encodes a repressor of Phl biosynthesis, which protein has the function of repressing (stopping) the expression of phl biosynthetic genes in bacteria that can otherwise synthesize Phl. Truncation of the repressor sequences resulted in loss of regulation of the phl biosynthetic sequences, and overproduction of Phl. The modification of these regulatory and coding sequences to modulate Phl production or to enhance the biocontrol capability of the host bacterial strain is also part of the present invention. Genomic sequences encoding a particular phl repressor gene protein, and a truncated derivative thereof, are specifically exemplified herein. DNA sequences that hybridize specifically to the phi repressor gene or its complement under standard conditions and which encode repressor genes that function to modulate or repress expression of phl biosynthetic genes are included in the present invention.

The present invention further comprises recombinant nucleic acid molecules containing a sequence of the invention. Such molecules include, for example, recombinant vectors, such as cloning, expression, or transformation vectors, which contain a DNA sequence which affects the production of Phl. The invention encompasses recombinant nucleic acid molecules which contain a bacterial regulatory element operably linked to a DNA sequence of the invention. The bacterial regulatory element may be a promoter from a gene isolated from Pseudomonas, Bacillus, *Escherichia coli*, or any other bacterium. In one embodiment of the present invention, the bacterial regulatory element is the native promoter of the sequences encoding for the production of Phl. The bacterial regulatory element may be from a gene which is homologous or heterologous to genes of the host bacterial strain.

Another aspect of the invention is the provision of cells which are transformed by the above vectors or DNA sequences.

A particular use of the invention is the provision of bacteria, bacterial biocontrol agents, or bacterial cells transformed with sequences that confer or enhance the ability of the bacteria or bacterial cell to produce Phl. Using the sequences of the invention, biocontrol agents can be produced which combine the ability to control growth of a plant pathogen and to compete aggressively in colonization of the plant rhizosphere. Further, the sequences of the invention contribute to the production of biocontrol agents which are able to inhibit a broad spectrum of plant pathogens.

The present invention also comprises methods of conferring or enhancing Phl biosynthetic capability in a host bacterial strain by transforming the host strain with the recombinant DNA sequences of the present invention. In a particular embodiment of the present invention, the transformed host strain is rendered active or more effective against fungal plant pathogens such as Gaeumannomyces graminis, Rhizoctonia solani, and species of the genera Pythium and Fusarium.

The present invention also comprises methods of conferring or enhancing Phl biosynthetic capability in a host bacterial strain by introducing the DNA sequence into the genome of a host bacterial strain. In the preferred embodiments of the invention, the host bacterial strain may be a pseudomonad, particularly strains of the species Pseudomonas fluorescens.

The present invention further comprises DNA sequences in isolated and purified form that can be used as probes or oligonucleotide primers for the identification of phl genes or functional equivalents thereof in bacterial strains and the use of such probes or primers to isolate DNA sequences encoding phl genes or functional equivalents thereof. The DNA sequences that specifically hybridize to the probes or primers and which encode functional phl genes are encompassed by the present invention. Further, because bacterial strains that contain phl genes are of potential value as biocontrol agents, the use of any portion of the DNA sequences that confer or enhance Phl biosynthetic capability to identify other strains of bacteria with potential Phl biosynthetic capability is included in the present invention.

Accordingly, it is one object of the present invention to provide DNA sequences and genes that confer or enhance Phl biosynthetic capability in bacterial strains.

It is another object of the present invention to provide gene constructs comprising DNA sequences which have the function of conferring or enhancing Phi biosynthetic capability in bacterial strains.

It is another object of the present invention to provide transformation vectors comprising phl gene constructs, which vectors are effective for stably introducing phl gene constructs into bacteria.

It is a further object of the invention to provide transgenic bacterial strains wherein the capability to produce Phl has been conferred or enhanced as a result of the introduction of phl gene constructs.

It is another object of the invention to provide transgenic bacterial strains enhanced in biocontrol activity against fungal pathogens, wherein the enhancement results from introduction of phl gene constructs.

It is a further object of the present invention to provide DNA sequences for use as probes or primers in the identification of strains of bacteria with potential biocontrol activity. Further, DNA sequences and genes are provided as probes and primers for the isolation of homologous genes from related and unrelated hosts. Using such sequences facilitates the identification of genes and the hosts strains harboring them for protection of plants against fungal pathogens.

It is a further object of the present invention to provide DNA sequences and genes which encode proteins that function in the production of Phl, including DNA sequences and genes which encode modified proteins that modulate the production of Phl in bacterial strains. Such modifications may alter the activity of regulatory genes, the expression of phl genes encoding biosynthetic proteins, and the biocontrol activity of host bacterial strains.

According to the present invention, the above objectives may be carried out by the isolation and use of DNA sequences that confer or enhance the production of 2,4-diacetylphloroglucinol in bacterial strains. The isolation of these genes and associated regulatory sequences is important for several reasons. First, in bacterial strains they confer or enhance the production of Phl, which is able to inhibit a wide range of fungal plant pathogens including Gaeumannomyces graminis, Rhizoctonia solani, and species of the genera Pythium and Fusarium. Secondly, they can function as probes and primers to screen for and identify naturally-occurring strains of bacteria with Phl biosynthetic capability. The use of bacterial strains transformed with DNA sequences that confer or enhance the production of Phl, or of Phl-producing strains identified by use of probes or primers derived from such sequences, provides an environmentally safe and effective method for control of these pathogens.

Examples of the sequences conferring Phl biosynthetic capability of the present have been deposited. Accordingly, the sequences conferring or enhancing Phl biosynthetic capability include the exemplified or deposited DNA sequences as well as the fragments derived from the exemplified or deposited sequences. By fragment is intended a DNA sequence which is capable of functioning to confer or modulate Phl biosynthetic capability or to identify the potential for such capability in bacteria.

The present invention further includes portions of such DNA fragments which function specifically in the synthesis of Phl but may not in themselves be sufficient to effect the production of PHL in transformed cells.

Other objects and advantages of this invention will become readily apparent from the ensuing description.

DEFINITONS

As used in the present application, the following terms have the meaning set out below:

Promoter or regulator DNA sequence: An untranslated DNA sequence which assists in, enhances, or otherwise affects the transcription, translation, or expression of an associated structural DNA sequence which codes for a protein or other DNA product. The promoter DNA sequence is usually located at the 5' end of a translated DNA sequence, typically between 20 and 100 nucleotides to the 5' end of the starting site for translation.

Structural or coding DNA sequence: A DNA sequence that is translated or transcribed in an organism to produce an RNA, a protein, or other DNA product.

Associated with/operably linked: Two DNA sequences which are "associated" or "operably linked" are related physically or functionally. For example, a promoter or regulator DNA sequence is said to be "associated with" a DNA sequence that codes for an RNA or a protein if the two sequences are operably linked, or situated such that the regulator DNA sequence will affect the expression level of the coding or structural DNA sequence.

Derived from: A first DNA sequence or fragment is said to be "derived from" a second DNA sequence or fragment if the former is physically isolated from the latter, or if the former is isolated by using part or all of the latter as a probe for isolation.

Substantial sequence homology: A sequence having substantial functional and structural equivalence between sequences of nucleotides or amino acids. In the case of a nucleotide sequence, a sequence having substantial sequence homology will have at least 70%, preferably 85%, and more preferably 90% homology to a reference nucleotide sequence, as opposed to nonspecific binding, and function specifically in the biosynthesis of Phl. Homologous sequences can be identified in a hybridization experiment. Conditions of high and low stringency are described below. In the case of amino acid sequences, the different sequences have at least 70%, more preferably 80%, and most preferably 90% or more similarity between the polypeptides coded for by the amino acid sequences and function specifically in the biosynthesis of Phl.

Locus: A segment of DNA that includes one or more coding or regulator DNA sequences that specifically affect a particular phenotypic trait.

Transformed cell: A cell or an ancestor of a cell that contains DNA introduced by the hand by any means known to the art, including but not limited to transformation, conjugation, and electroporation.

The arrow marked Red⁻ represents the region within which insertions caused loss of red pigment production and reduced Phl production. A vertical arrow indicates the position of the Tn5 insertion in Q2-87::Tn5-1. Restriction sites: B=BamHI, Bs=BstEII, C=ClaI, E=EcoRV, H=HindIII, P=PstI, Pv=PvuII, S=SalI .

Figure 3:
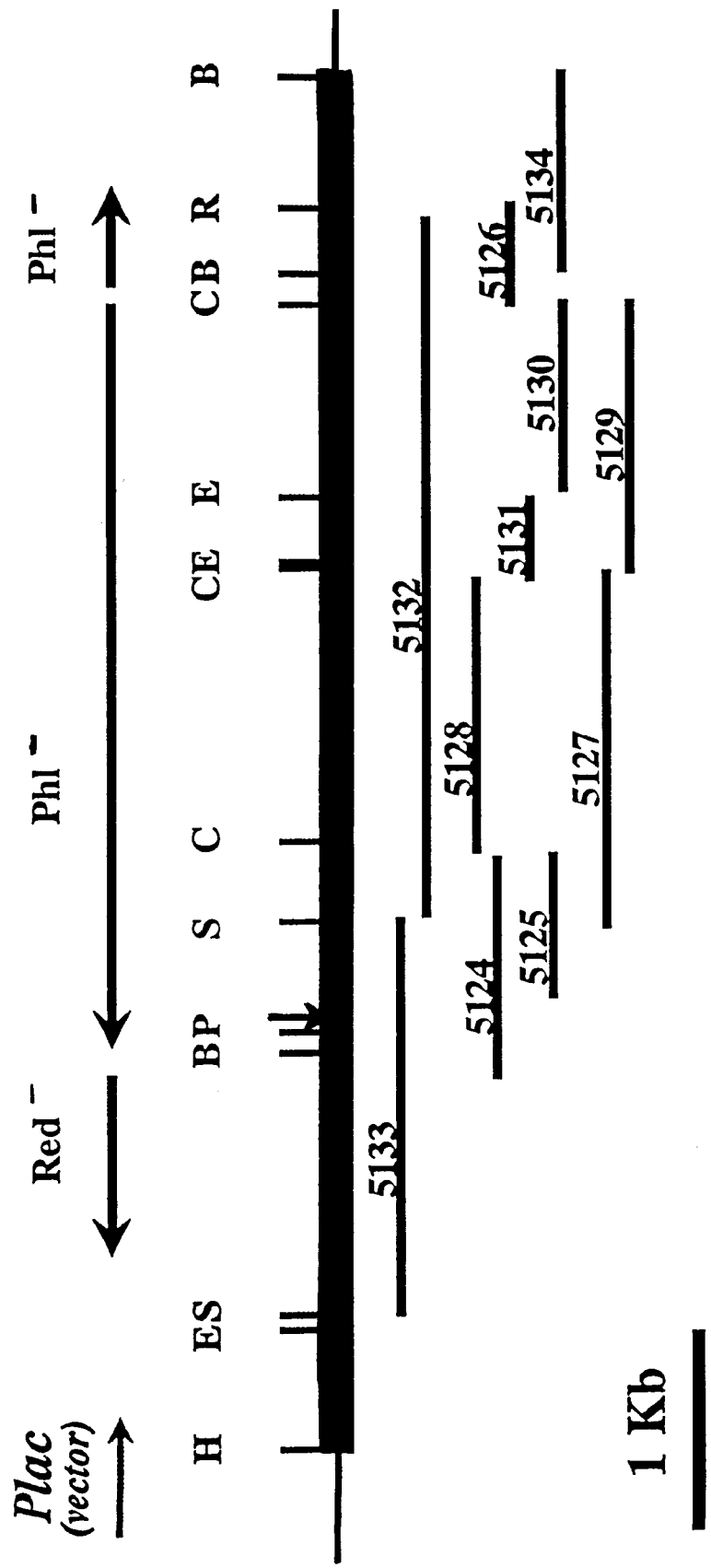

FIG. 3. Subclones generated for determination of the DNA sequences given in SEQ ID NO:3. Restriction enzyme sites used to generate the subclones were: 5124, BamlHI, ClaI; 5125, PstI, ClaI; 5126, ClaI, EcoRI; 5127, SalI, EcoRV; 5128, ClaI; 5129, ClaI; 5130, EcoRV, ClaI; 5131, ClaI, EcoRV; 5132, SalI, EcoRI; 5133, SalI; 5134, BamHI. Horizontal arrows marked Phl⁻ indicate the regions in which transposon insertions caused loss of Phl biosynthetic capability. The arrow marked Red⁻ represents the region within which insertions caused loss of red pigment production and reduced Phl production. The vertical arrow identifies the site of insertion of the Tn5 transposon in Q2-87::Tn5-1. Restriction enzyme sites: B=BamHI, C=ClaI, E=EcoRV, H=HindIII, P=PstI, R=EcoRI, S=SalI.

Figure 4:
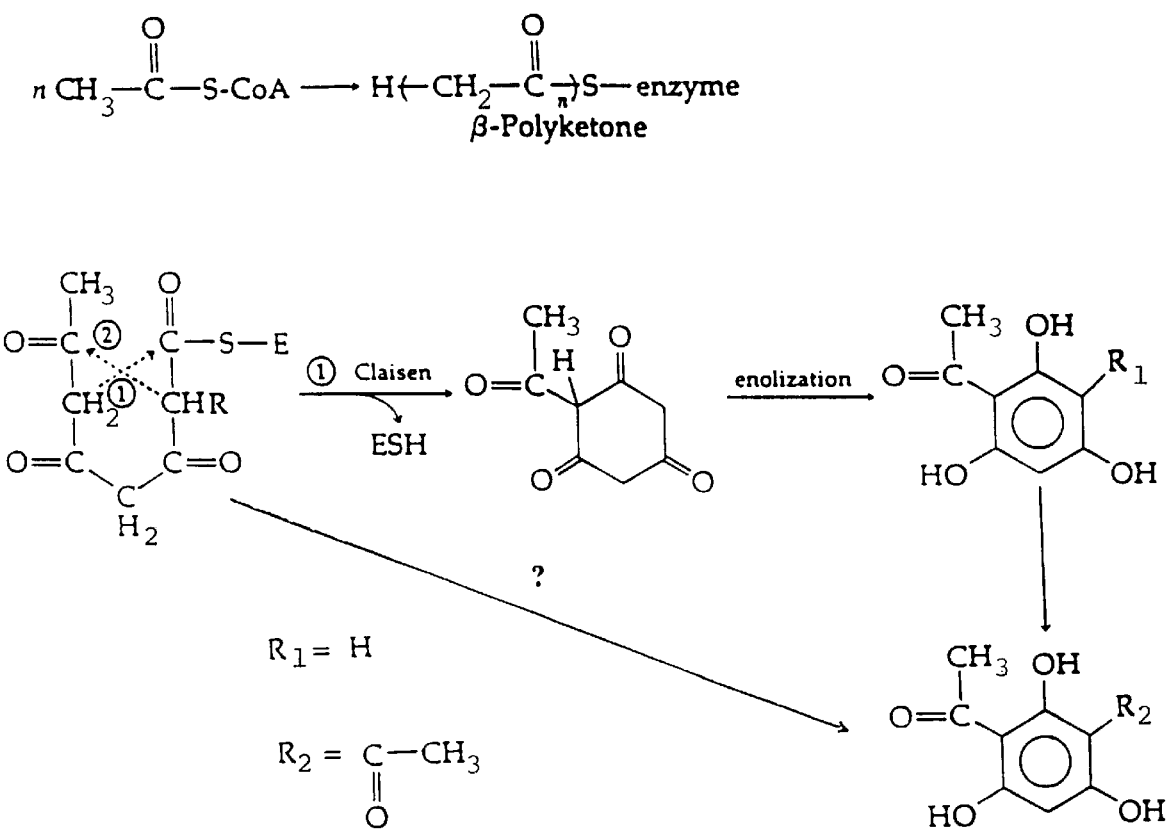

FIG. 4. Proposed biosynthetic pathway for 2,4-diacetylphloroglucinol, adapted from D. E. Metzler, BIOCHEMISTRY, The Chemical Reactions of Living Cells. Chain building is thought to be initiated by the condensation of an acyl thioester "starter" unit with a malonyl "extender" unit to yield $CO_2$ plus a $C_4$ acetoacetyl intermediate which is then further elongated by sequential condensation reactions with additional acetyl groups donated by malonyl extender units. Monoacetylacetylphloroglucinol (MAPG) could then be formed as shown. The conversion of MAPG to 2,4-diacetylphloroglucinol (Phl) by an enzyme designated MAPG acetyltransferase has been demonstrated in vitro by *P. fluorescens* F113 by Shanahan et al. Whether Phl also may arise directly by cyclization of a ketodecanoyl thioester intermediate is not known.

Figure 5:
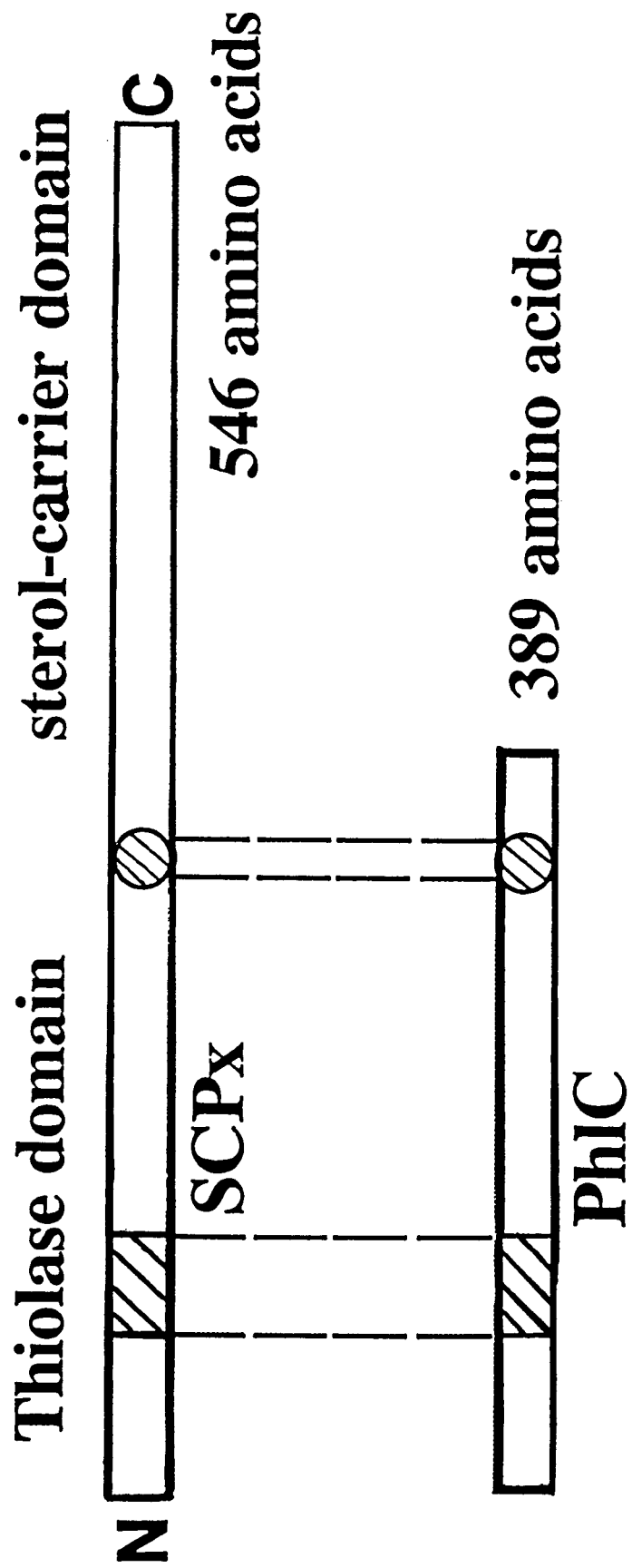

FIG. 5. Similarity of PhlC to the thiolase portion of sterol carrier protein x (SCPx). Boxed region at the left end of PhlC indicates the position of the conserved putative substrate-binding site; oval represents conserved glycine-rich C-terminal region.

Figure 6:
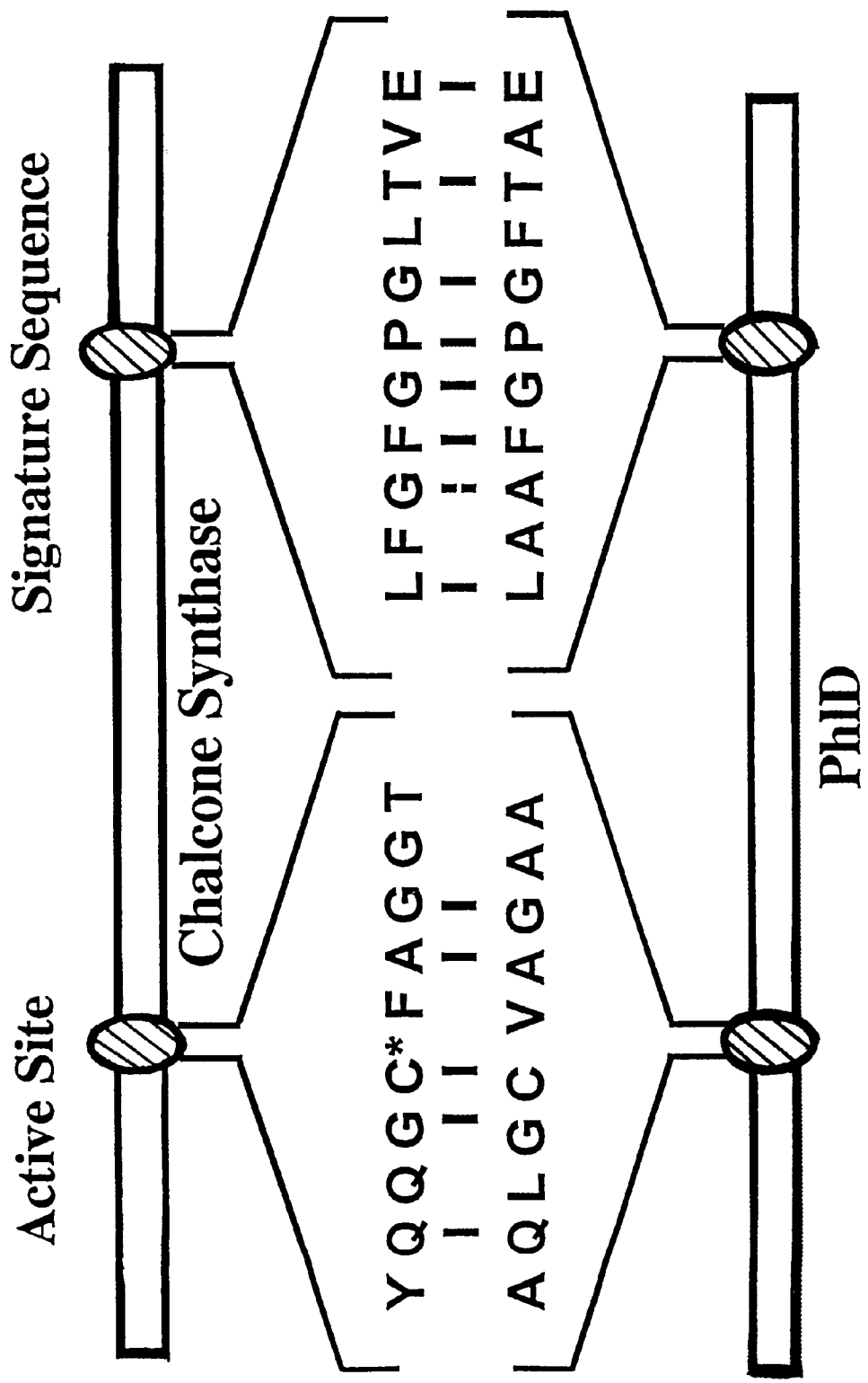

FIG. 6. Conservation in PhlD of the active site residues and the signature sequence of the chalcone synthase family. The asterisk marks the catalytic cysteine.

Figure 7:
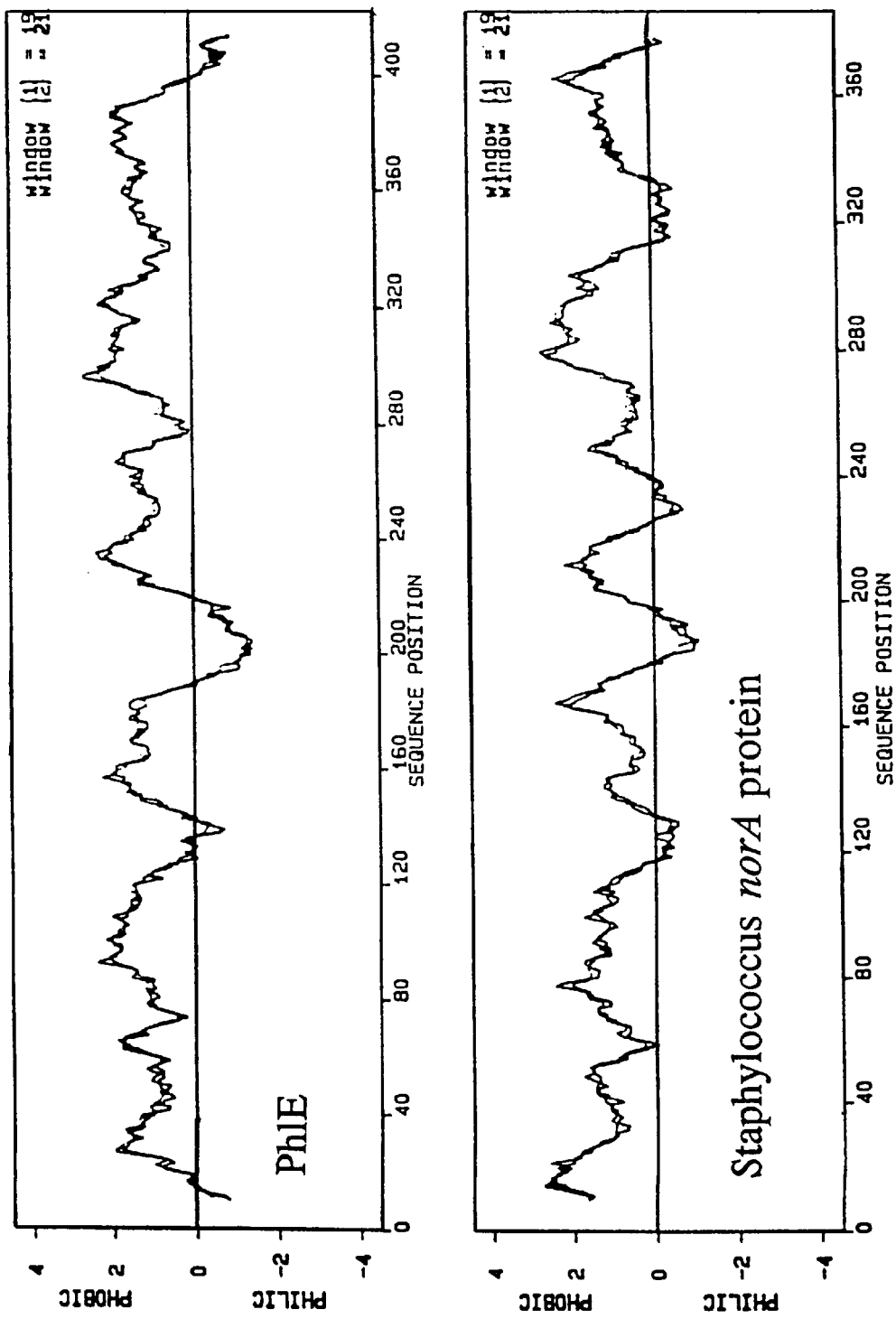

FIG. 7. Kyte-Doolittle hydropathy plots of PhlE and Staphylococcus norA protein. Both show central hydrophilic loops flanked by hydrophobic, potential membrane-spanning regions of 19 or 21 amino acids (Window size=19, 21).

FIG. 8. Conserved helix-turn-helix motif of the repressor protein PhlF as compared to similar domains in other known repressor proteins including the λ cro and λ repressor proteins, phage 434 cro and repressor proteins, lac repressor, catabolite reactive protein (CRP), and *E. coli* tetracycline repressor protein. The HTH score is a measure of probability that the amino acid sequence predicts a functional DNA-binding domain and was higher for the PhlF protein than for the known λ cro and λ repressor proteins as well as the phage 434 cro and repressor proteins.

DETAILED DESCRITION OF THE INVENTION

The present invention provides DNA sequences in isolated and purified form which function specifically in the biosynthesis of 2,4-diacetylphloroglucinol (Phl) and which can effect the production of Phl by conferring or enhancing the ability of an organism to produce Phl. Manipulation of these genetic elements, either separately or in combination, can be used to introduce or enhance biosynthetic capability in organisms transformed with the sequences.

In particular, we have identified, cloned, and sequenced DNA sequences from *Pseudomonas fluorescens* Q2-87 and used the sequences to introduce Phl biosynthetic capability in Phl-nonproducing bacterial strains. We also have determined that strains of Pseudomonas capable of producing Phl, when transformed with these sequences, are enhanced in Phl production. Further, bacterial biocontrol agents transformed with these sequences produce Phl and are enhanced in their biocontrol activity.

The present disclosure is the first report of the cloning, sequencing and reproducible mediation of transgenic Phl production by phl genes of Pseudomonas.

The phl genes include genomic sequences which encode phl gene proteins and coding and regulatory sequences which direct and regulate the transcriptional and translational expression of the phl-coding sequences. As defined herein, "phi gene proteins" refers to proteins having the ability to function in the production of 2,4-diacetylphloroglucinol in bacteria synthesizing phl gene proteins. The phi locus is that segment of DNA that encompasses the coding and associated regulator DNA sequences that specifically encode the ability to confer or enhance Phl production. Exemplified phl gene products have predicted molecular masses of 27,679 kDa (PhlA); 27,445 kDa (PhlB); 41,721 kDa (PhlC); 38,389 kDa (PhlD); 45,259 kDa (PhlE); 23,044 kDa (PhlF) and 45,473 kDa (PhlR). The predicted amino acid sequence of PhlA is given in SEQ ID NO:6. The predicted amino acid sequence of PhlB is given in SEQ ID NO:8. The predicted amino acid sequence of PhlC is given in SEQ ID NO: 10. The predicted amino acid sequence of PhlD is given in SEQ ID NO: 12. The predicted amino acid sequence of PhlE is given in SEQ ID NO: 14. The predicted amino acid sequence of PhlF is given in SEQ ID NO:16. The predicted amino acid sequence of PhlR is given in SEQ ID NO: 18. The predicted amino acid sequence of a truncated PhlF protein is given in SEQ ID NO:20. The exemplified genomic DNA sequence which encompasses regulatory and coding sequences for these phl gene products is provided in SEQ ID NO:3. A truncated genomic DNA sequence (from pMON5122) is given in SEQ ID NO:4.

The degeneracy of the genetic code is well known to the art; therefore, synonymous coding sequences with one or more codon substitutions can be readily determined by one of ordinary skill in the art. Synonymous coding sequences vary from the exemplified coding sequences but encode proteins of the same amino acid sequences as as those specifically provided herein.

Specific embodiments of nucleotide sequences which encode phl gene proteins which have the function of participating in the synthesis of Phl are given in SEQ ID NOS:5 (phlA), 7 (phlB), 9 (phlC), 11 (phlD), and 17 (phlR). A nucleic acid sequence that encodes a phl gene protein that functions to regulate the expression of phl genes and the production of Phl is given in SEQ ID NO: 15 (phlF). A truncated version of this sequence which encodes a truncated phl gene protein that facilitates overproduction of Phl is given in SEQ ID NO: 19. A nucleic acid sequence that encodes a phl gene protein that functions to enhance the antagonistic activity of Phl-producing bacteria transformed with phl genes is given in SEQ ID NO: 13 (phlE).

Figure 1:
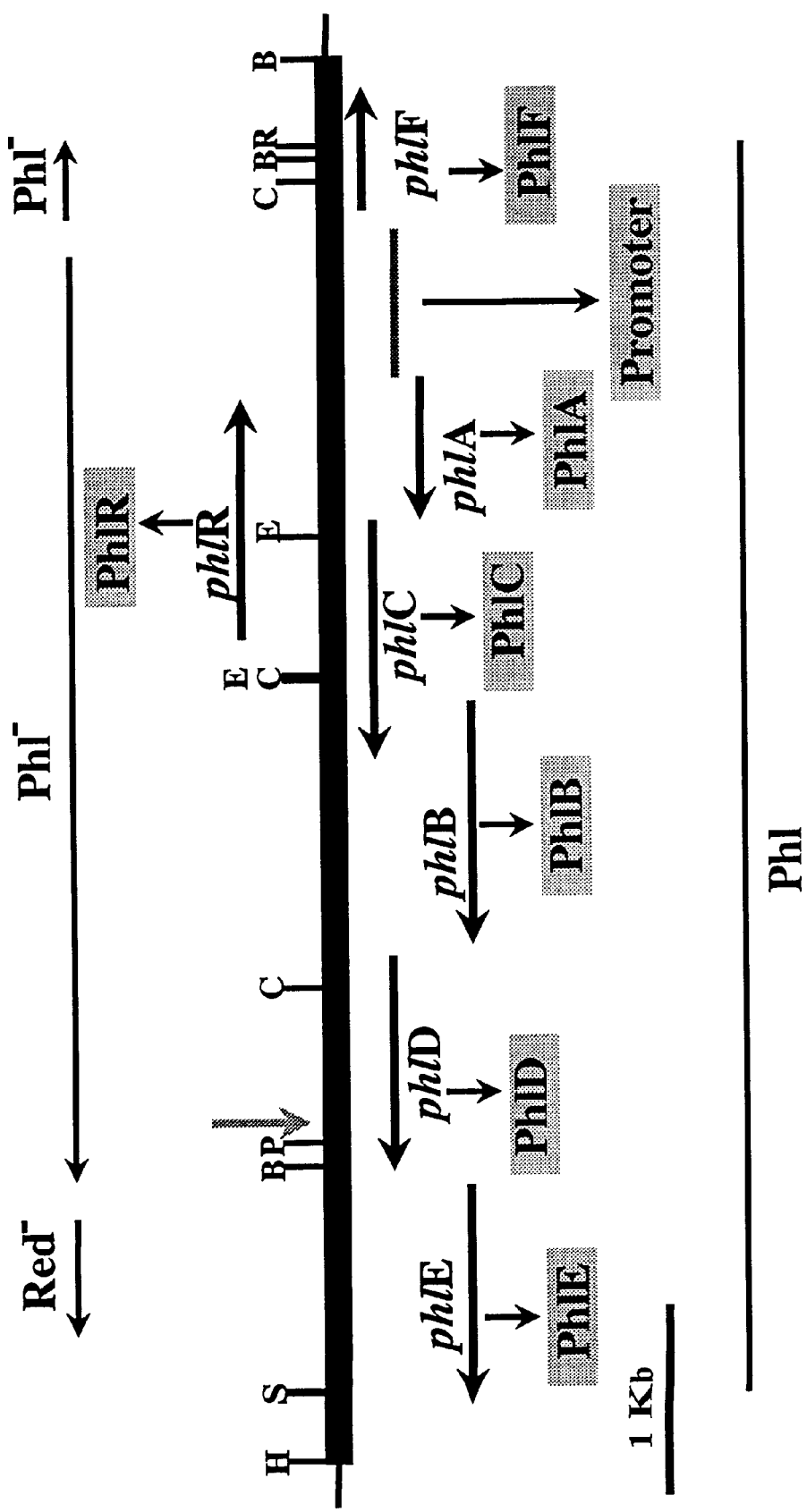
FIG. 1. This figure shows the genetic organization of the DNA sequences present in SEQ ID NO:3. Names in italics represent open reading frames (genes), whereas names within boxes represent the predicted protein sequences. The gray vertical arrow identifies the site of insertion of the Tn5 transposon in Q2-87::Tn5-1. The line at the bottom marked by Phl shows the approximate location of the segment of DNA included in SEQ ID NO:4, and capable of conferring or enhancing Phl production in transformed strains of Pseudomonas. The arrows marked Phl⁻ delineate the position and orientation of sequences identified by Tn3HoHo1 mutagenesis as being essential for Phl biosynthesis. The arrow marked Red⁻ represents the region within which insertions caused loss of red pigment production and reduced Phl production. Restriction enzyme sites: B=BamHI, C=ClaI, E=EcoRV, H=HindIII, P=PstI, R=EcoRI, S=SalI.

A genomic DNA sequence containing phl genes required for Phl synthesis is presented in SEQ ID NO: 1. The DNA sequence is 3680 bp in length. Nucleotide sequence analysis reveals five open reading frames (coding portions) and intergenic spaces that initiate at base 2 and terminate at base 3680 (FIG. 1). The open reading frame designated phlA initiates at base 3680, terminates at base 2889 and encodes a protein, PhlA, 264 amino acids in length. The open reading frame designated phlB initiates at base 1917, terminates at base 1210, and encodes a protein, PhlB, 236 amino acids in length. The open reading frame designated phlC initiates at base 2855, terminates at base 1689, and encodes a protein, PhlC, 389 amino acids in length. The open reading frame designated phlD initiates at base 1048, terminates at base 2, and encodes a protein, PhlD, 349 amino acids in length. The open reading frame designated phlR initiates at base 2118, terminates at base 3371, and encodes a protein, PhlR, of 418 amino acids. The predicted proteins PhlA, PhlB, PhlC, PhlD and PhlR are described in Example 4, below.

A genomic DNA sequence containing phl genes that function in Phl production is presented in SEQ ID NO:2. The DNA sequence is 5076 bp in length. The resulting open reading frames and intergenic spaces initiate at base 2 and terminate at base 5076. This sequence encompasses that of SEQ ID NO: 1 and 1396 contiguous bases which include an open reading frame initiating at base 1270 and terminating at base 2. This open reading frame encodes a protein, PhlE, 423 amino acids in length. The encoded protein is described in Example 4, below.

A genomic DNA sequence containing phl genes that function in Phl production is presented in SEQ ID NO:3. The DNA sequence is 6387 bp in length. The resulting open reading frames, intergenic spaces and regulatory regions initiate at base 2 and terminate at base 6387. This sequence encompasses that of SEQ ID NO:2 and 1311 contiguous bases which include regulatory sequences and an open reading frame initiating at base 5781 and terminating at base 6386. This open reading frame encodes a protein, PhlF, 202 amino acids in length. The encoded protein is described in Example 4, below. The DNA sequence of SEQ ID NO:3 is contained within a SalI-BamHI fragment of 7203 base pairs in the clone pMON5120, was deposited under terms of the Budapest Treaty Jun. 21, 1995 with the USDA Agricultural Research Service Culture Collection, Northern Regional Research Laboratory (NRRL), and has been designated NRRL accession number B-21477.

A genomic DNA sequence which contains phlACBDE, phlR, and a truncated phlF gene relative to that of SEQ ID NO:3 and SEQ ID NO: 15 is given in SEQ ID NO:4. This genomic DNA is 6170 bp in length. Open reading frames, intergenic spaces and regulatory regions initiate at base 2 and terminate at base 6170. This sequence encompasses that of SEQ ID NO:2 and 1094 contiguous bases which include regulatory sequences and a portion of the phlF open reading frame initiating at base 5781 and terminating at base 6170. The truncated phlF protein is 130 amino acids in length. Its DNA coding and amino acid sequences are given in SEQ ID NO: 19 and SEQ ID NO:20, respectively. When transformed into bacterial strains, the sequences present in SEQ ID NO:4 confer or enhance Phl production. The DNA sequence of SEQ ID NO:4 is contained within a SalI-EcoRI fragment of 6586 bp in the plasmid pPHL5122, was deposited under terms of the Budapest Treaty Jun. 21, 1995 in the Agricultural Research Culture Collection (NRRL), 1815 North University Street, Peoria, Ill., and has been designated NRRL accession number B-21476.

Nucleotide and amino acid sequences having substantial sequence homology to the exemplified or deposited sequences are encompassed in this invention.

Sequences for Phl Production

Genomic sequences capable of inducing Phl production may transfer either gene(s) that encode biosynthetic enzymes or a positive regulatory element that can activate the expression of unassociated and unexpressed (cryptic) genes indigenous to the host strain. Examples of cryptic genes that have been activated by introduction of positive regulatory elements include those for the synthesis of Phl and HCN. Mutations in genes encoding positive regulators typically have a complex phenotype because the functional gene product is unavailable to activate the expression of other genes, including those for the production of Phl and HCN. We found no evidence that Phl production in the transformed strains could be explained by introduction of a positive global activator of gene expression.

We have found that DNA sequences encompassing production of Phl are contained within a DNA fragment encompassing five genes, phlACBD and phlR (FIG. 1), and that the coding sequences of these genes predict proteins with catalytic activities consistent with roles in the biosynthesis of Phl.

Of the DNA fragments from *P. fluorescens* Q2-87 implicated by Vincent et al. in the production of the Phl, only the fragment designated pMON5122 was able to transfer Phl biosynthetic capability to the Phl-nonproducing strain *P. fluorescens* M4-80R (Example 1; Table 1). Fragments smaller than that in pMON5122 were unable to transfer Phl biosynthetic activity, suggesting that essential sequences had been deleted, and fragments larger than pMON5122 also failed to confer biosynthetic capability, suggesting that they contained negative regulator sequences.

The cloned fragment from pMON5122 was transferred to the plasmid pVSP41, a vector which is stably maintained in Pseudomonas in the absence of antibiotic selection, and introduced into five Phl-nonproducing strains and into Q2-87. Derivatives of all of Phl-nonproducing strains containing pPHL5122 produced Phl but were unaltered in other phenotypes including production of HCN. Phl production by Q2-87(pPHL5122) was enhanced over that by Q2-87 alone or that by Q2-87(pVSP41), the vector-bearing strain (Example 1, Table 2).

Q2-87::Tn5-1, shown by Vincent, et al. to be defective in Phl production, contains the transposon Tn5 within a genomic copy of the sequences cloned on pPHL5122. Phenotypic characterization Q2-87::Tn5-1 revealed that it remained HCN$^+$.

Field studies of strains containing the cloned sequences that confer or enhance Phl production will require that introduced genes be stably incorporated into the chromosome of the host strain. As illustrated in Example 1, below, we used the mini-transposon vector pUT mini-Tn5 Km (de Lorenzo and Timmis, *Meth. in Enymol.* 235:386–405 (1994)) to transfer sequences from pMON5122 to the chromosomes of rhizosphere pseudomonads including strains Q69c-80, Q65c-80, and the phenazine antibiotic-producing strains 2–79 and 30–84. Other materials for stable introduction are known to those in the art and are encompassed by this invention.

To confirm insertion of the mini-Tn5 vector, the kanamycin-resistant transposition derivatives of Q69c-80 were characterized. Results from Southern hybridization indicated that single copies of the Phl genes had transposed to different sites in individual derivatives, and all of the derivatives initially produced Phl in vitro. Quantities of Phl sometimes were over twenty-fold greater than produced by Q69c-80(pPHl5122) (Example 1; Table 3), and Phl usually was not detectable in cultures of strain Q2-87 grown under comparable conditions.

The reproducibility of transfer and the specificity of the affected phenotype in these studies indicate that sequences present on pMON5122 include genes encoding a Phl biosynthetic pathway, rather than a global activator of Phl synthesis.

Figure 2:
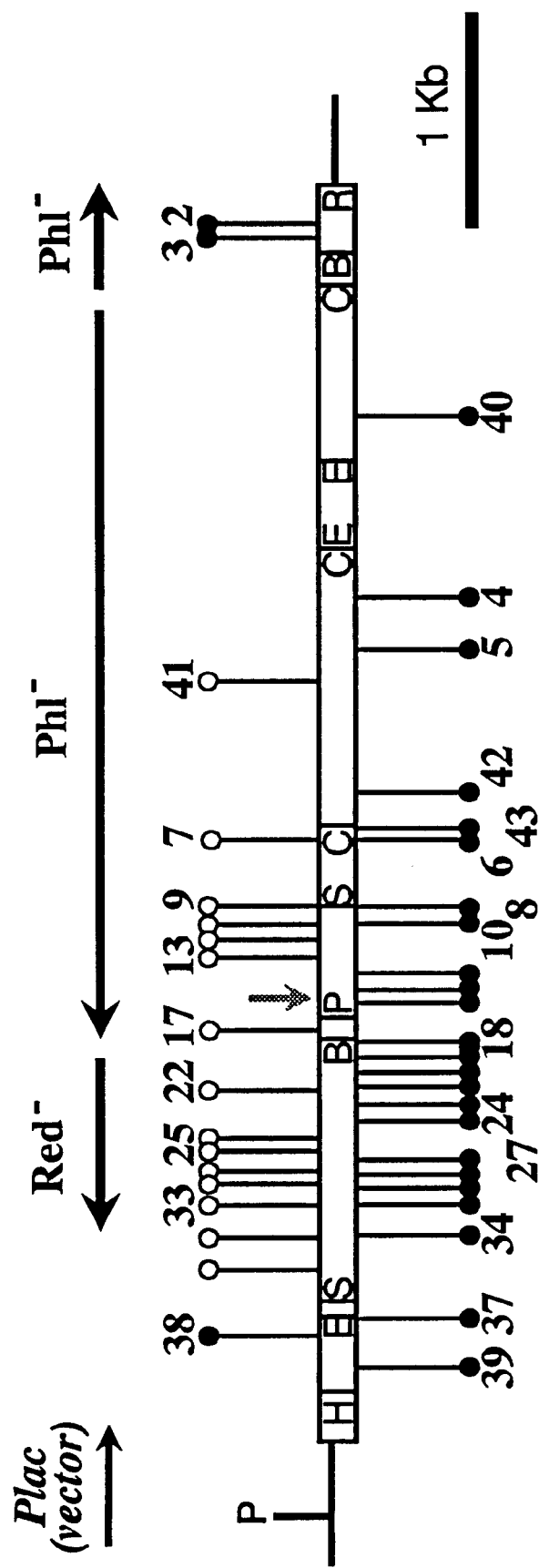
FIG. 2. This figure indicates the location of Tn3HoHo1 insertions used to define sequences required to confer or enhance Phl biosynthetic capability in the plasmid pMON5122. Filled and open circles represent Lac⁺ and Lac⁺ insertions respectively. Lac⁺ insertions are transcriptionally active, whereas Lac insertions are not. Insertions are numbered sequentially from right to left except for insertions 40, 41, 42, and 43 which are marked. Horizontal arrows marked Phl⁻ indicate the regions in which insertions caused loss of Phl biosynthetic capability.

The portion of pMON5122 active in Phl production was defined by mutagenesis with the transposon Tn3HoHo1 (Stachel et al., *EMBO J.* 4:891–898.(1885)). The site and orientation of each insertion were determined (Example 2; FIG. 2), and the effect on Phl production and expression of the transposon-encoded lacZ gene were evaluated after introduction of the mutated plasmids into the Phl-nonproducing strain M4-80R. All insertions which resulted in expression of lacZ, except three, were similarly oriented, only the Lac$^+$ insertions 2 and 3 at the right end and insertion 38 at the left end of the cloned fragment had the opposite orientation (Example 3; FIG. 2).

Insertions resulting in reduction or loss of Phl production, spanned approximately 5 kb of the 6.5 kb fragment and delineated at least two similarly oriented transcriptional/translational units (Example 2; FIG. 2, Table 4). These results show that not all of the sequences present on pMON5122 are necessary for Phl production.

As shown in Example 2 below, whereas all insertions up to and including number 18 that were Phl$^-$ also also failed to produce the red pigment, insertions downstream of number 18 exhibited different phenotypes. Most of these insertions had no effect on Phl synthesis (Table 4) and transformants containing the mutated plasmids had the characteristic red color. However, insertion derivatives 20, 25, and 33 exhibited a level of Phl production that was intermediate between the positive and negative controls, remained inhibitory to *C. michiganensis* subsp. *michiganensis* in vitro (Table 4), and failed to exhibit red pigmentation. The region containing insertions 20, 25 and 33 is designated Red$^-$ in FIGS. 1 and 2 and is considered to provide a function that enhances, but is not required for Phl production in M4-80R.

Subclones spanning the ca. 5-kb region were generated (FIG. 3) and submitted to the Nucleic Acid Sequencing Facility, Iowa State University, for sequence determination. Using the Genetics Computer Group (GCG) package as supported by the Washington State University VADMS facility, we have identified six large complete open reading frames, designated phlA, phlB, phlC, phlD, phlE, and (in the opposite orientation) phlR within this region (FIG. 1). The fragment containing phlA through phlD encoded on one DNA strand, with phlR on the other strand, contains genes necessary to confer or enhance Phl production, and phlD is required for the synthesis of Phl. A larger fragment encompassing the above plus the adjacent phlE gene can confer or enhance Phl production and includes an additional gene, the product of which enhances the synthesis, activity, and/or export of Phl. The function of this gene is not required for Phl production in transformed M4-80R, but such function may be necessary for Phl production or export in other bacterial host strains.

DNA sequences for production of Phl encode catalytic proteins

The enzymatic steps required for Phl synthesis in bacteria are unknown, but can be anticipated based on knowledge that the structure of Phl is consistent with synthesis via a polyketide mechanism (FIG. 4). Similarities also are known to exist between fatty acid and polyketide synthases, β-ketoacyl synthases (FAS), thiolases, and polyketide synthases (PKS) in bacteria, and the stilbene and chalcone synthase (STS/CHS) enzymes from plants. Synthesis of both polyketides and fatty acids is known to initiate by condensation of an acetyl starter unit with malonyl-ACP; this step generally is catalyzed by a β-ketoacyl synthase separate from the one(s) that catalyze subsequent chain elongation via condensation reactions that sequentially add $C_2$ units from malonyl thioesters to the growing chain. In bacterial FAS, separate acetyl and malonyl transferases are required, as is a transferase for chain termination. PKS in Streptomyces resembles PAS in that ACP-linked residues are implicated as building units based on the presence in PKS loci of an ACP gene. A significant difference between CHS and the FAS and PKS β-ketoacyl synthases is that CHS requires neither ACP nor specific transferases; malonyl-CoA units are added to a coumaroyl-CoA starter unit. Based on these precedents, it is reasonable that Phl synthesis minimally will require a chain-initiating β-ketoacyl synthase; a malonyl condensing enzyme, and a cyclase for ring closure. Depending on the mechanism of transfer, and acyl carrier protein may also be required.

Analysis of the protein sequences encoded by SEQ ID NO: 1 and comparison to other protein sequences revealed conserved structural motifs and similarities to known proteins that are consistent with predicted functions in Phl biosynthesis via the polyketide pathway. Motifs conserved (mismatch=1) within PhlA include the short chain alcohol dehydrogenase family signature, the ornithine/diaminopimelic acid/arginine decarboxylase family 2 signature, and a phosphopantetheine attachment site (Example 4). These motifs suggest that PhlA may function either in the provision of substrates for PhlD and/or as an acyl carrier.

A partially conserved (mismatch=1) thiolase signature sequence within the PhlR protein sequence indicates similarity to type II thiolases that catalyze the thiolysis of acetoacetyl-coA and are involved in pathways such as poly-β-hydroxybutyrate synthesis and steroid biogenesis which resemble the Phl pathway (FIG. 4) in their dependence on condensation reactions involving short-chain acyl thioesters.

Analysis of the PhlC protein sequence and comparison to other protein sequences revealed significant similarity to the N-terminal portion of mammalian peroxisomal sterol carrier protein X (SCPx) (example 4; FIG. 5). This portion of SCPX has 3-oxoacyl-CoA thiolase activity, and is hypothesized to supply acetyl-CoA for anabolic reactions in cells well-supplied with energy. By analogy to SCPx, the PhlC product may provide a source of CoA starter units for the synthesis of Phl. Alternatively, because thiolases share conserved residues in their condensing domains with β-ketoacyl synthases and chalcone synthases, the similarity we have detected between PhlC and SCPx may indicate activity in chain elongation reactions analogous to those that occur in fatty acid and polyketide biosynthesis.

PhlD is required for Phl production, and the PhlD protein revealed a highly significant similarity to members of the chalcone synthase/stilbene synthase (CHS/STS) family of enzymes from higher plants. PhlD contained regions with extensive similarity to the active site and signature sequence domains of CHS/STS enzymes (Example 4; FIG. 6) but had surprisingly little similarity to prokaryotic β-ketoacyl synthases, including those that catalyze similar condensing reactions (e.g., polyketide synthesis by actinomycetes) in bacteria. It is, to our knowledge, the first prokaryotic protein to show such extensive similarity to the CHS/STS protein family. Acylphloroglucinols have been recovered as by-products of chalcone synthesis in vitro, suggesting that PhlD may be sufficient to catalyze the condensation and/or cyclization reactions required for synthesis of monoacetylphloroglucinol (FIG. 4).

Based on results from mutagenesis (Example 2), phenotypic characterization of transformants (example 1) containing DNA fragments that confer or enhance Phl biosynthetic capability, and sequence analysis of the predicted protein sequences encoded within these fragments (Example 4), the segment of DNA containing phlACBD and phlR comprises the minimum known to date to be required for production of Phl.

Contiguous sequences modulate Phl production

Mutagenesis of pMON5122 with Tn3HoHo1 revealed a locus designated Red and located adjacent to those sequences present in SEQ ID NO: 1. The Red locus was not itself required for Phl production, but M48-R(pMON5122), containing certain mutations in Red were less inhibitory in vitro (Table 4). The Red locus therefore had the capacity to enhance Phl production or activity, perhaps by facilitating Phl export, in strains transformed with a DNA segment that includes phlACBD and phlR.

The DNA sequences within the Red locus were found to contain an open reading frame encoding a protein designated PhlE with significant similarity to Staphylococcus aureus norA protein, which contributes to fluoroquinone resistance. NorA and other such proteins are members of a very large superfamily of transmembrane solute facilitators; among the most well-known representatives of the drug efflux subfamily are the tetracycline resistance proteins. PHlE retained conserved structural features of these integral membrane permeases (FIG. 7), including a central hydrophilic loop bordered on either side by six hydrophobic α-helices. The results of phenotypic analysis of mutations in the Red region, combined with knowledge of the predicted structure of the PHlE protein are consistent with PHlE functioning in the export of Phl. Such export would reduce the intracellular Phl concentration, and may represent a mechanism of resistance by which bacteria producing Phl avoid autointoxication.

A seventh open reading frame designated phlF was identified upstream of and oriented divergently from phlAB-CDE. This open reading frame is present in truncated form in pPHl5122. The DNA sequences including phlABCDE, phlR, the intervening sequences (which are likely to contain promoters based on their position and AT-richness) and the truncated phlF gene are included in SEQ ID NO:4. In pPH5122 this DNA fragment was capable of conferring or enhancing Phl production in all strains of Pseudomonas into which it was introduced (Example 1). The DNA sequence consisting of phlABCDE, phlR, the intervening sequences containing the putative promoter region, and the complete phlF gene are given in SEQ ID NO:3.

The PhlF protein sequence was similar to those of tetracycline repressor protein, and other known repressors, particularly within a conserved helix-turn-helix domain (FIG. 8) which is a characteristic feature of such DNA-binding repressors. It is known that the tetracycline repressor controls expression of the terR resistance gene, and that repressor gene deletions resulting in truncation of the carboxy-terminal end of the repressor protein can result in overexpression of the resistance protein. By analogy, the very high levels of Phl production by transformed derivatives of P. fluorescens Q69c-80 containing a construct consisting of the truncated phlF and the phlACBDE and phlR genes (Table 3) support the argument that the phlF gene is a repressor of phl gene expression. That pMON5120, containing an intact phlF gene, does not transfer Phl biosynthetic capability (Table 1) further strengthens the argument.

Those skilled in the art will also be aware that it will be possible to improve the effectiveness of a Phl-producing biological control strain by modulating the level of expression or activity of that strain's Phl biosynthetic genes. This can be accomplished by genetic manipulation of cloned genes such as phlE and phlF, followed by introduction into the genome. In strains that already produce Phl, the altered genes may be introduced to replace the native genes by homologous recombination, or may be introduced at a separate location. An example of the latter is the introduction by transposition (according to the method given in Example 1) of a heterologous promoter operably linked to the truncated phlF gene. The truncated PhlF protein competes with the intact protein, relieving the repression caused by the native protein and permitting increased Phl production. The level of competition, and hence, the level of Phl overproduction, is controlled by the strength of the heterologous promoter relative to the native phlF promoter. Such promoters are readily available to those skilled in the art, and a possible means of fusing them to genes such as the truncated phlF gene, involves the use of the overlap extension polymerase chain reaction strategy (Horton et al., *Gene* 77:61 (1989)). Alternatively, the truncated phlF gene, under control of its native promoter or a heterologous promoter, is substituted by homologous recombination for the genomic phlF gene, again effecting increased Phl production.

Another aspect of the invention is genetically engineered recombinant nucleic acid molecules, i.e., non-naturally occurring nucleic acid molecules, preferably DNA, containing a portion encoding a phl gene protein or a functional phl gene homolog, which has the function of conferring or enhancing Phl production in bacteria expressing phl genes or functional homologs thereof. A recombinant DNA molecule refers to a hybrid DNA sequence comprising at least two DNA sequences, the first sequence not normally being found together in nature with the second. Such molecules can be obtained by manipulation of genetic material using restriction enzymes, ligases, and similar recombinant techniques as described by, for example, Sambrook et al., (*Molecular Cloning*, second edition, Cold Spring Harbor Laboratory, Plainview, N.Y.; (1989)), Ausubel et al., *Current Protocols in Molecular Biology*, Current Protocols (1989), and *DNA Cloning: A Practical Approach*, Volumes I and II (ed. D. N. Glover) IREL Press, Oxford, 1985. Examples include recombinant vectors, such as cloning or expression vectors which contain DNA sequences encoding phl gene proteins which are in a 5' to 3' (sense) orientation or in a 3' to 5' (antisense) orientation. "Recombinant," as used in the present application, does not refer to naturally-occurring genetic recombinations.

The recombinant DNA sequences of the present invention may originate from Pseudomonas or from organisms of a different taxonomic classification. The recombinant DNA sequences of the present invention may further comprise one or more regulatory DNA sequences operably linked to the structural DNA sequences above. Such regulatory sequences include promoter sequences, leader sequences, and other DNA sequences which may affect the expression of the regulatory DNA sequences, as well as those fragments of a regulator DNA sequence that are able to act with such effect. Bacterial regulatory elements known in the art include any bacterial regulatory element that is known to function as a promoter, enhancer, ribosome binding site, and/or any other regulatory control mechanism of the associated coding sequence. Bacterial regulatory elements include hybrid regulatory regions comprising mixtures of parts of regulatory elements from different sources. For example the trp-lac (tac) promoter combines the -35 region of the *E. coli* tryptophan operon with the -10 region of the *E. coli* lac operon promoter and functions effectively in Pseudomonas (Bagdasarian et al., *Gene* 26:273–282 (1983)). An associated coding DNA sequence is one that is adjacent or adjoining 3' to the regulatory elements and which codes for a protein when transcribed and translated. Bacterial regulatory elements can be isolated from commercially available vectors, bacterial regulatory elements known in the art, and bacterial regulatory elements identified by using promoter-less marker-containing transposons or promoter selection vectors.

As used herein, a nucleic acid molecule can be a DNA molecule, an RNA molecule or a DNA-RNA hybrid molecule. A non-naturally occurring nucleic acid molecule is one which does not occur in nature. A non-naturally-occurring nucleic acid molecule, includes, for example, DNA sequences, in isolated and purified form; a recombinant nucleic acid molecule having a heterologous region, that is, an identifiable segment of DNA that is not covalently linked to the Phl gene coding sequences in nature; or such a non-naturally occurring molecule may be constructed of parts which have been chemically synthesized; or a synthetic sequence having codons different than the native gene. Parts from heterologous sources may be joined by any means known to the art, e.g., by ligation in vitro. Alternatively, parts may be joined in an in vivo process such as by recombination, but such recombination will be directed by the hand of man and the desired result will be identified by man.

The Use of Phl Sequences for Plant Pathogen Control

It is an aspect of the present invention that improved biological control strains can be generated following the introduction of genes that confer Phl biosynthetic capability into a variety of bacterial isolates from nature. This approach represents a method for the generation of potentially effective biocontrol strains adapted to a variety of crop plants or ecosystems.

It is a further aspect of the present invention that Phl-producing biological control strains can be rendered more effective by the introduction of genes described herein that enhance Phl biosynthetic capability.

In another embodiment of the present invention, biocontrol agents are provided which are able to inhibit the growth of fungal pathogens, such as *Gaeumannomyces graminis, Rhizoctonia solani*, and species of the genera Pythium and Fusarium. These biocontrol agents may be bacteria, plant cells or animal cells transformed with the recombinant DNA sequences above, but are preferably bacterial strains, and more preferably Gram negative bacteria, such as those of the genus Pseudomonas. Most preferred as biocontrol agents are strains of the species *Pseudomonas fluorescens*.

Another embodiment of the present invention provides methods of inhibiting the growth of fungal pathogens, such as *Gaeumannomyces graminis, Rhizoctonia solani*, and species of the genera Pythium and Fusarium. In the methods of the present invention, the DNA sequences that confer or enhance Phl production can be introduced into the genome of a bacterial strain which may not ordinarily be effective as an inhibitor of fungal pathogens, resulting in an effective biocontrol strain.

DNA in the form of plasmids can be transferred from one bacterium to another by a sexual process termed conjugation. Plasmids that mediate conjugal transfer contain genes that code for the synthesis of pili. These pili are hollow filaments that join the plasmid-bearing (donor) bacterium with another bacterium (recipient), and through which replicated copies of the plasmid pass from the donor to the recipient. This procedure occurs naturally and is utilized in the laboratory as a method of transferring genes between bacteria. For some strains of Pseudomonas, conjugal transfer is the preferred method of transfer because these bacteria are not readily transformed with isolated and purified DNA.

Most of the plasmids commonly used as vectors for conjugal transfer in the laboratory do not themselves cause conjugation, but are transmissible and can be mobilized when conjugation is mediated by a coresident conjugative plasmid. Transmissible plasmids may have a broad host range (i.e., able to replicate in a variety of bacterial hosts) or a narrow host range (i.e., replication is limited to *E. coli*). Examples of broad host range transmissible plasmids suitable for genetic analysis in Gram-negative soil bacteria are provided in *Transformation of Plants and Soil Microorganisms*, K. Wang, A. Herrero-Estrella, and M. Van Montagu, Eds., Cambridge University Press, Cambridge (1995). Broad host range transmissible plasmids may be stably maintained in Pseudomonas in the absence of selection (e.g., pPHL5122) or more usually maintained only in the presence of an antibiotic, resistance to which is encoded on the plasmid (e.g., pMON5122).

Plasmids that are stably maintained under selection are suitable as vectors in vitro (Tables 1 and 2), but are unacceptable when the cloned DNA they carry must be functionally evaluated in an environment such as soil where it is not possible to maintain continuous antibiotic selection. Stably maintained transmissible plasmids are appropriate for use as vectors under contained conditions such as the growth chamber where persistence of the plasmid in the host is desired, and there is no danger of gene escape into the environment (Table 5). Bacteria harboring transmissible vectors containing cloned DNA may not be released into natural environments, however, because the possibility exists for uncontrolled mobilization of recombinant DNA mediated by conjugative plasmids indigenous to native soil microorganisms.

Stable insertion of cloned phl genes into bacterial strains in a manner suitable for environmental release may be accomplished by homologous recombination or by transposition. When mediated by recombination, a selectable marker is first introduced into or adjacent to the Phl DNA in such a way that phi gene functions are not disrupted. The marked phl genes are cloned into a fragment of chromosomal DNA containing the target site of insertion such that the sequences containing the marker gene and the phl genes are flanked on either side by target site sequences of no less than 500 bp, and preferrably of at least 1 kb. The entire recombinant fragment is introduced into the target strain on a transmissible plasmid, and transformants are selected that retain the Phl gene marker, but not that of the vector.

Transposons provide an alternative means to the generation of stable chromosomal insertions. Sequences containing phl genes are cloned within a transposable element which contains a selectable marker and is carried on a transmissible plasmid. Transposition functions are provided by genes encoded on a plasmid not maintained in the target strain; this may be the plasmid carrying the transposable element (Herrero et al., *J. Bacteriol.* 172:6557–6567 (1990); de Lorenzo et al., supra) or a separate plasmid (Barry, *Gene* 71:75–84 (1988)). The construction of a transposable element containing phl genes is described in Example 1, and an example of its use in in situ assessment of phl gene activity is given in Example 8.

In another embodiment of the present invention, methods are provided for producing Phl which is effective in inhibiting the growth of fungal pathogens including *Gaeumannomyces graminis*, *Rhizoctonia solani*, and species of the genera Pythium and Fusarium. This method comprises introducing the recombinant sequences of the present invention into the genome of of a bacterium, allowing the transformed bacteria to produce Phl, and extracting the antibiotic from cultures of the transformed agent.

The present invention encompasses the preparation of antifungal formulations in which one or more transformed bacterial strains is used as an active ingredient. The present invention further encompasses the preparation of antifungal formulations in which the active ingredient is Phl produced by the transformed bacterial agent of the present invention. Formulations in which the active ingredient is a bacterial biocontrol agent or the antibiotic Phl produced by such agent may be applied in any manner known for seed and soil treatment with such preparations.

Other uses

To identify phl genes from other bacterial species, preferably species of the genus Pseudomonas, genomic DNA from a culture of the bacteria is isolated as described below. The isolated DNA is cut with one or more restriction enzymes, cloned in an appropriate vector such as a cosmid vector to generate a library, and DNA from colonies containing clones from the library is blotted onto a nylon membrane such as Nytran. The blots are probed with an oligonucleotide probe containing a phl gene or portion thereof greater than 9 nucleic acids in length, and preferably greater than about 18 nucleic acids in length. Probes to specific structural features of the Phl proteins are preferred as they provide a means to isolate phl genes with similar structural domains. Most preferred are probes including the catalytic and signature domains of phlD, which is required for production of Phl. Probes may be based on the sequence of either strand of the DNA comprising the motif, and can be degenerate (i.e., a mixture of all possible coding sequences for a given amino acid sequence). General methods for designing and preparing such probes are provided, for example, in Ausubel et al., supra, and *Guide to Molecular Cloning Techniques*, 1987, S. L. Berger and A. R. Kimmel, eds., Academic Press, New York. These oligonucleotides are useful for phl gene isolation, either through their use as probes capable of hybridizing to phl complementary sequences or as primers for various polymerase chain reaction cloning strategies.

Hybridization procedures and techniques are well known to those skilled in the art and are described in Ausubel, supra, and in *Guide to Molecular Cloning Techniques*, 1987, S. L. Berger and A. R. Kimmel, eds., Academic Press, New York. If desired, a mixture of different oligonucleotide probes may be used for the screening of the recombinant library. Conditions of high stringency for detecting a phl gene include hybridization at about 42° C. and about 50% formamide; and sequential washes at 65° C. in 2×SSC-1% SDS and 0.1×SSC. Lower stringency conditions can be achieved by one or more of the following: hybrdiziation at 42° C. without formamide, washing at 42° C., and washing in 6×SSC-1% SDS followed by 6×SSC-0.1% SDS.

Oligonucleotides derived from phl gene sequences can also be used as primers in PCR cloning strategies. PCR methods are well known in the art and described, for example, in *PCR Technology*, H. A. Erlich, ed., Stockton Press, London, 1989; *PCR Protocols: A Guide to Methods and Applications*, M. A. Innes, D. H. Gelfand, J. J. Snitsky, and T. J. White, eds. (1990), and Ausubel et al., supra. *P. fluorescens* contains one genomic region encoding phl proteins. The conserved regions in the phl genes are useful in the design of primers to mediate the recovery of functional phl homolog genes in other bacteria, particularly members of the genus Pseudomonas. Such primers are designed to amplify only sequences flanked by the oligonucleotides in genes having sequence identity to phl genes.

Once a clone encoding a putative phl gene is identified, it is then determined whether the candidate gene is capable of producing a functional Phl homolog protein. A functional Phl homolog protein is one encoded by DNA from a source other than *P. fluorescens* Q2-87 which can, when substituted for the homologous phl gene protein from strain Q2-87, function in place of that Q2-87 phl gene protein. Assays based on the functional substitution of one protein for another are termed complementation assays and, in bacteria, generally are conducted in a strain in which the gene to be complemented is inactivated by mutation, and the gene to be tested for complementation activity is introduced on a plasmid. Thus, in Table 1 the mutant Q2-87::Tn5-1 was complemented with the plasmid pMON5122, and in Example 7, Q2-87::Tn5-1 was not complemented with a BamHI-ClaI fragment from phlD.

The availability of the *P. fluorescens* nucleic acid molecules encoding phl gene proteins makes accessible phl gene sequences encoding phl gene proteins or functional homologs from other bacterial strains. The phl gene sequences or portions thereof are used as oligonucleotide probes to hybridize to the additional genomic sequences by hybridization under standard conditions. Sequences which hybridize specifically to a phl gene coding sequence or its complement and which encode a Phl functional homolog protein are encompassed by the invention. Such oligonucleotides are prepared by standard methods and assembled by procedures known to those in the art. The length of the probe employed must be sufficient to hybridize to homologous regions of DNA wherein hybridization is due to at least about 70% homology, as opposed to nonspecific binding.

It is well known in the biological arts that certain amino acid substitutions can be made in protein sequences without affecting the function of the protein. Generally, conservative animo acid substitutions or substitutions of similar amino acids are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in *Atlas of Protein Sequence and Structure*, Vol. 5, Supplement 3, Chapter 22, pages 345–352, which is incorporated by reference herein, provides frequency tables for amino acid substitutions which can be employed as a measure of amino acid similarity. Dayhoff's frequency tables are based on comparisons of amino acid sequences for proteins having the same function from a variety of evolutionarily different sources.

The amino acid sequence of the protein may or may not be identical with the amino acid sequence which occurs naturally in bacteria. The identity of phl genes can be confirmed by their ability to produce a functional Phl homolog protein as defined above. In addition, artificially induced mutations can be included so long as they do not destroy activity. A "mutated Phl protein" refers to protein which has the same activity as its unmutated predecessor, but which is derived by mutation of a DNA encoding a Phl protein. By "derived from mutation" is meant both direct physical derivation from a DNA encoding the starting material Phl gene protein using, for example, site specific mutagenesis or indirect derivation by synthesis of DNA having a sequence related to, but deliberately different from, that of the Phl gene. As means for constructing oligonucleotides of the required length are available, such DNAs can be constructed wholly or partially from their individual constituent nucleotides.

Genetically engineered means that the result has been directed by the hand of man. A bacterium genetically engineered to contain a particular DNA molecule is one into which the DNA has been introduced by any means known to the art, including but not limited to transformation, conjugation, electroporation, particle bombardment, and the like. A genetically engineered nucleic acid molecule, such as a genetically engineered DNA molecule, is one which is the product of molecular biological process including but not limited to DNA ligation, in vitro mutagenesis or the like.

The DNA sequences of the invention are useful to prepare DNA expression molecules by cloning the sequence in any suitable expression vector that is capable of introducing a foreign gene into a heterologous bacterial host. The recombinant vector is constructed so that the coding sequence is located in the vector with the appropriate control sequence and operationally associated therewith, that is, the positioning and orientation of the phl gene DNA coding sequence with respect to the control sequences is such that the coding sequence is transcribed under the control of the control sequences (i.e., by RNA polymerase which attaches to the DNA molecule at the control sequences). The control sequences may be ligated to the coding sequence prior to insertion into a vector. Alternatively, the coding sequence can be cloned directly into an expression vector which already contains the control sequence and an appropriate restriction site downstream from the control sequence. The vector should be selected so as to have a promoter operable in the host cell into which the vector is to be inserted (that is, the promoter should be recognized by the RNA polymerase of the host cell). In addition, the vector should have a region which codes for a ribosome binding site positioned between the promoter and the site at which the DNA sequence is inserted so as to be operatively associated with the phl gene coding sequence once inserted. The vector should be selected to provide a region which codes for a ribosomal binding site recognized by the ribosomes of the host cell into which the vector is to be inserted.

EXAMPLES

The following examples are intended only to further illustrate the invention and are not intended to limit the scope of the invention as claimed. The examples use many techniques well known and accessible to those skilled in the arts of molecular biology and in the manipulation of recombinant DNA in bacteria. Enzymes are obtained from commercial sources and are used according to the vendors' recommendations or other variations known to the art. Reagents, buffers and culture conditions are also known to the art. References providing standard molecular biological procedures include Sambrook et al. (1989) *Molecular Cloning*, second edition, Cold Spring Harbor Laboratory, Plainview, N.Y.; R. Wu (ed.) (1993) *Methods in Enzymology* 218: Wu et al. (eds.) *Methods in Enzymology* 100, 101; Glover (ed.) (1985); *DNA Cloning*, Vols. I and II, IRL Press, Oxford, UK; and Hames and Higgins (eds.) (1985) *Nucleic Acid Hybridization*, IRL Press, Oxford, UK. Abbreviations and nomenclature, where employed, are deemed standard in the field and are commonly used in professional journal such as those cited herein. All references cited in the present application are expressly incorporated by reference herein.

Example 1

Identification of a fragment capable of conferring and enhancing Phl production.

A. The genetic region that carries all the information necessary to direct Phl biosynthesis is identified by cloning DNA segments from a Phl-producing strain such as Q2-87 into a suitable broad host range vector such as pRK415 (carries a tetracycline resistance marker) that can be maintained in transformed Pseudomonas strains, and introducing the cloned DNA segments into a rifampicin-resistant mutant of the Phl-nonproducer *P. fluorescens* M4-80R via a triparental mating (Thomashow and Weller, *J. Bacteriol.* 170:3499–3508 (1988). The transformed derivatives were then screened for (1) the presence of a soluble red pigment, the presence of which is correlated with production of Phl; (2) the ability to inhibit in vitro the growth of the indicator bacterium *Clavibacter michiganensis* subsp. michiganensis; and (3) production of Phl as determined directly by extraction and analysis by thin layer chromatography.

For triparental matings, overnight cultures (in 5 ml LB with appropriate antibiotic selection) of the donor *Escheri*- chia coli strain DH5α carrying plasmids with inserted Q2-87 DNA, and the helper E. coli strain HB101 (pRK2013) (provides functions required for DNA transfer by bacterial conjugation) were centrifuged and resuspended in 500 μl of fresh LB broth. 25 μl of each of these cultures was spotted onto Millipore filter papers (1 cm$^2$) and mixed; after incubation for 2 hours at 37° C., 30 μl of the recipient strain P. fluorescens M4-80R, (10 ml LB culture grown overnight at 28° C., centrifuged, and resuspended as above) was added. Filters were incubated overnight at 28° C. and the resulting cell mass was resuspended in 1 ml of sterile distilled water. Aliquots of 200 μl of this suspension were spread on LB plates containing rifampicin and tetracycline.

Rifampicin and tetracycline resistant transformants obtained from triparental matings were evaluated for production of red pigment visually after growth on Yeast Malt (YM) broth or King's Medium B (King, et. al., J. Lab. Clin. Med. 44:301–307 (1954)), after incubation at 28° C. for 4 to 7 days.

A spontaneous, tetracycline-resistant mutant of Clavibacter michiganensis subsp. michiganensis was used to assess inhibition in vitro. Inhibition of C. m. michiganensis by Phl was analyzed as follows: 100 μl of a 48-hour old-culture of the indicator organism in water agar (3ml) was overlayed on YM plates with appropriate antibiotic. These plates were incubated for 4 to 6 h to let the agar solidify and allow initial growth of C. m. michiganensis. Strains to be tested for Phl production were spotted onto these plates using a toothpick. Strains were assayed in sets of three per plate and each set was analyzed in triplicate. Each plate also included the positive control strain M4-80R (pMON5122) and the negative control strain, M4-80R (pRK415). The diameter of the zones of inhibition was measured after two to four days and the values were compared statistically among sets by an analysis of variance (ANOVA); the set means were compared by a least significant different test (LSD) when significant differences among sets was indicated by the ANOVA (Fisher's protected LSD).

For extraction of Phl and monoacetylphloroglucinol (MAPG), a possible Phl precursor, cultures were grown for 4 to 7 days either in liquid YM medium or on YM plates. The cells were removed by centrigation and the antibiotic was extracted from the cell pellet as described by Keel et al. (1992) except that the final extract was dissolved in 100% methanol. The samples were chromatographed on Uniplate™ Silica Gel GHLF TLC plates (Alltech Associates Inc. Deerfield, Ill.) in a solvent system of chloroform:acetone 9:1 (v/v). Spots were visualized by UV absorption at 254nm.

For example, the plasmid pMON5118 and its deletion derivatives, described by Vincent et al. (Appl. Environ. Microbiol. 57:2928–2934 (1991), were introduced into P. fluorescens strain M4-80R by triparental mating.

Strain M4-80R carrying any of the plasmids pMON5116, pMON5117, pMON5118, pMON5120 and pMON5123 did not produce the red pigment and did not inhibit C. m. michiganensis. Neither Phl nor MAPG could be isolated from any of these strains. On the other hand, strain M4-80R (pMON5122) showed red pigment production, inhibited C. m. michiganensis, and both Phl and MAPG were isolated from broth as well as agar cultures of this strain (Table 1). Thus, only plasmid pMON5122 was able to transfer Phl biosynthetic capability to strain M4-80R. The fact that larger fragments (pMON5120, pMON5118 and pMON5117) carrying DNA sequences flanking the fragment in pMON5122 were unable to transfer Phl synthesis may indicate that they carry negative regulator sequences.

TABLE 1

| Plasmids | Q2-87::Tn5 | | | M480R | | |
|---|---|---|---|---|---|---|
| | Ph1 | Red pigment | HCN | Ph1 | Red pigment | HCN |
| pMON5118 | + | 4 | 5 | − | 0 | 0 |
| pMON5117 | + | 3 | 5 | − | 0 | 0 |
| PMON5120 | + | 3 | 5 | − | 0 | 0 |
| pMON5122 | + | 4 | 5 | + | 4 | 0 |
| pMON5123 | + | N.D. | 5 | − | 0 | 0 |

B. To determine whether the fragment from pMON5122 was able to confer or enhance Phl biosynthetic capability in a wide range of P. fluorescens strains, it was cloned as a HindIII-EcoRI fragment into pVSP41, a plasmid that can be maintained in Pseudomonas strains without antibiotic selection. This construction, called pPHL5122, was introduced into 6 Pseudomonas strains by triparental matings as described above, and the production of phl by the transformed strains was assessed by production of red pigment and extraction of Phl from broth cultures as described above. Plasmid pPHL5122 directed Phl synthesis in all of the six transformed recipients. Strains that did not already produce Phl acquired ability to produce the antibiotic. Strains that already produced Phl, i.e., Q2-87, showed an increase in antibiotic production (e.g. Q2-87(pPHL5122), Table 2). pPHL5122 also transferred Phl biosynthetic capability to seven other Phl nonproducing recipient strains into which it was introduced as indicated by the presence of the red pigment. Thus, pPHL5122 conferred or enhanced Phl biosynthesis in all strains into which it was introduced.

To determine whether the locus contained on pMON5122 specifically directed Phl production, or if it also affected the production of other secondary metabolites as would be expected of a global regulatory gene, HCN production was assayed in Q2-87, Q2-87::Tn5 (a mutant described by Vincent et al. with a Tn5 transposon that inactivates the genomic homologue of the genes cloned in pPHL5122), and the seven transconjugant derivative strains into which pPHL5122 (or pMON5122) was introduced. Strains were grown on modified KMB medium containing 4.4g/L glycine (Pierson and Thomashow, Mol. Plant-Microbe Interact. 5:330–339 (1992)). HCN indicator paper was taped to the lid of the plates and the plates were sealed with Parafilm and incubated for 2 to 4 days at 28° C. HCN indicator paper was prepared by soaking Whatmann 3MM filter paper in a solution of 2% sodium carbonate and 0.5% picric acid and air drying. HCN production was detected by the yellow to red color change of the indicator paper. P. fluorescens strain CHAO, which produces copious amounts of HCN, was used as positive control and strain M4R-80, which does not produce HCN, was included as a negative control. Four of the recipient strains (M4-80R, M7z-80, Q26a-80, and Q29z-80) did not produce HCN, whereas three others (M23dz-80, Q69c-80R2, and Q2-87) were HCN$^+$ (Table 2). Both Q2-87 and Q2-87::Tn5 produced similar amounts of HCN as detected by the conversion of the yellow HCN indicator paper to red color, indicating that the Tn5 insertion specifically inactivated production of Phl. Further, HCN production was not coordinately transferred with Phl biosynthesis in the HCN-nonproducing strains upon introduction of pPHL5122, nor was the amount of HCN produced by strain M23dz-80 detectably changed by plasmid pPHL5122. However, HCN production was slightly reduced in Q69c-80 (PVSP 41) and Q69c-80 (pPHL5122) and markedly lessened in Q2-87 (pPHL5122) (Table 2). As expected, pPHL5122 also conferred the Red phenotype characteristic of Phl biosynthesis; otherwise, the appearance of the transgenic strains was unchanged. These results indicate that the fragment contained on pPHL5122 does not mediate global activation of genes involved in secondary metabolism.

TABLE 2

| Strains | Phl synthesis μg/ml culture | Red pigment production | HCN production |
|---|---|---|---|
| M7z-80 | 0 | 0 | 0 |
| M7z-80(pVSP41) | 0 | 0 | 0 |
| M7z-80(pPHL5122) | 0.25 | 2 | 0 |
| Q2a-80 | 0 | 0 | 0 |
| Q2a-80(pVSP41) | 0 | 0 | 0 |
| Q2a-80(pPHL5122) | 600–2000 | 4 | 0 |
| Q29z-80 | 0 | 0 | 0 |
| Q29z-80(pVSP41) | 0 | 0 | 0 |
| Q29z-80(pPHL5122) | 20–35 | 4 | 0 |
| M23dz-80 | 0 | 0 | 1 |
| M23dz-80(pVSP41) | 0 | 0 | 1 |
| M23dz-80(pPHL5122) | 10–20 | 5 | 1 |
| Q69c-80R2 | 0 | 0 | 4 |
| Q69c-80R2(pVSP41) | 0 | 0 | 3 |
| Q69c-80R2(pPHL5122) | 1.0–3.75 | 4 | 3 |
| Q2-87 | 0.5 | 5 | 5 |
| Q2-87(pVSP41) | 0 | 5 | 5 |
| Q2-87(pPHL5122) | 30–200 | 5 | 2 |

C. We have used the mini-transposon vector pUT mini-Tn5 Km described by de Lorenzo, et al., supra, to introduce Phl biosynthetic genes from pMON5122 into the chromosomes of rhizosphere pseudomonads including strains Q69c-80, Q65c-80, and the PCA-producing strains 2–79 and 30–84. The HindIII-EcoRI fragment from pMON5122 was cloned into the plasmid vector pUCNotI such that NotI restriction sites were added at either end of the fragment, and the fragment was then excised by digestion with NotI and ligated into the NotI site in the vector pUT::Km. This site is located between two IS-terminal sequences that also flank a transposable miniTn5 element carrying a kanamycin resistance gene, and pUT::Km also carries a transposase gene adjacent to but outside of the mobile DNA segment (Herrero et al, *J. Bacteriol.* 172:6557–6567 (1990)). The resulting plasmid, pUT::Km-Phl, can only replicate in bacterial strains that provide an R6K-specified π protein not produced by recipient strains of Pseudomonas. Transfer of the plasmid pUT::Km-Phl from the donor strain *E. coli* S17-1λpir, into the Pseudomonas recipient strains Q69c-80, Q65c-80, 2–79 and 30–84 was by conjugation. The donor strain, which provides the necessary conjugation factors, was grown overnight with shaking at 37° C. in 5 ml of LB broth amended with ampicillin and kanamycin (each 100 μg/ml). Each rifampicin-resistant recipient pseudomonad was grown overnight in 5 ml of LB broth without antibiotics. The cultures were centrifuged at 6,000 rpm for 5 min and resuspended in 1 ml of fresh LB broth. For each recipient strain, thirty μl of the donor was spotted onto a membrane filter placed on an LB plate, and then 20 μl of cell suspension of one recipient strain was added and the two were mixed. These plates were incubated at 27° C. overnight, and then the bacterial growth on each filter was suspended in 1 ml of sterile distilled water, centrifuged, and resuspended in 1 ml of sterile distilled water. The washed cells were diluted 10-fold, and 100 μl of each dilution was plated on M9 minimal medium (0.3 g $KH_2PO_4$, 0.5 g sodium chloride, 1.0 g ammonium chloride, 1 ml calcium chloride (50 mM), 1 ml $MgSO_4 \cdot 7H_2O$ (1 M)) amended with 100 μg/ml of kanamycin ($M9_{kmn100}$) and incubated at 27° C. for 3 days. By selecting for kanamycin-resistant transconjugants from this mating, strains were obtained in which the mini-Tn5 element containing phl genes and the kanamycin resistance gene had transposed into the Pseudomonas genome. Twenty kanamycin-resistant transposition derivatives of Q69c-80 have been evaluated for the presence of phl genes and for Phl production. Strain Q69c-80::mTn5PHL20 was deposited under terms of the Budapest Treaty Jun. 21, 1995 in the Agricultural Research Culture Collection (NRRL), 1815 North University Street, Peoria, Ill., and has been assigned accession number NRRL B-21474. Southern blot analysis (Photogene Nucleic Acid Detection System, BRL®, Life Technologies, Inc., Gaithersburg, Md. 20898, USA) was carried out to confirm insertion of the Phl biosynthetic locus and reveal the insertion pattern of the locus on the chromosome of *P. fluorescens* Q69c-80. For Southern hybridization, genomic DNA was prepared as described by Ausubel et al., supra. Cultures were grown overnight in 1.5 ml of LB broth, the bacterial cells were centrifuged and resuspended in a lysis solution (561 μl $T_{10}E_1$ buffer, 15 μl of 20% SDS, and 12 μl of 5 mg/ml Pronase®) and incubated at 37° C. for 1 h. One hundred two microliters of 5 M NaCl was added and mixed thoroughly. Eighty microliters of CTAB/NaCl solution was added and mixed, and the suspension was incubated at 65° C. for 10 min. The DNA was extracted sequentially with equal volumes of phenol/chloroform/isoamyl alcohol (25:24:1) and with chloroform /isoamyl alcohol (24:1). The DNA was precipitated with 60% volume of isopropanol and washed with 70% ethanol before resuspending in $T_{10}E_1$ buffer. Genomic DNA from each of the 20 derivatives was digested with SalI (first experiment) or EcoRV (second experiment). Digested DNA was separated by electrophoresis on a 0.7% agarose gel, and transferred and bound to a nylon membrane (Magnagraph®, Micron Separations Inc., Westboro, Mass. 01581, USA) by known methods.

Eight hundred microliters (5 mg/ml) of salmon sperm DNA (Sigma, St. Louis, Mo. 63178, USA) was boiled for 10 min and diluted into 40 ml of hybridization solution (1× HPB, 1% SDS). The membrane and the hybridization solution were introduced into a sealable plastic bag and incubated for 2 to 4 h at 65° C.

A DNA probe consisting of the excised and purified fragment from pMON5122 labeled as directed by the manufacturer with the BioNick Labeling System (Gibco BRL, Life Technologies, Inc., Gaithersburg, Md. 20898, USA) was boiled for 10 min, added to the plastic bag, and incubated overnight at 65° C. After hybridization, the membrane was washed twice in 100 ml of a solution (5× SSC, 0.5% SDS) at 65° C. for 5 min per wash, once with 100 ml of a solution (0.1× SSC, 1% SDS) at 65° C. for 30 min, once in 100 ml of 2× SSC at room temperature for 5 min, and then incubated in 100 ml of blocking solution (Tris-buffered saline (TBS)-Tween 20, 3% BSA) for 1 h at 65° C. Seven microliters of streptavidin-alkaline phosphatase (SA-AP) was diluted into 7 ml of TBS-Tween 20 (1:1000 dilution), and the resultant solution was poured on the membrane and incubated at room temperature for 10 min with repeated pipetting. The membrane was washed twice in 100 ml of TBS-Tween 20 at room temperature for 15 min each time and in 100 ml of the BRL final wash buffer at room temperature for 1 h. The membrane was briefly blotted to remove excess liquid and placed on a plastic development sheet. One milliliter of the development reagent was dropped near the membrane on the plastic development sheet and immediately covered with another plastic sheet to spread the reagent evenly under conditions of reduced light. After 30 min, a piece of film was placed over the membrane, exposed for 2–4 h and developed. Results from Southern hybridization indicated that single copies of the Phl genes had transposed to unique sites in the individual derivatives.

All of the derivatives initially produced Phl in vitro as indicated by the presence of the soluble red pigment described above. Phl production was quantified by using High Pressure Liquid Chromatography (HPLC). Pseudomonads were grown with shaking (200 rpm) in 15 ml culture tubes with 4.0 ml yeast malt broth for 60 h at room temperature. Cultures were acidified with 125 μl of 3.0 N HCl, and extracted twice with 10 ml ethyl acetate (90% extraction efficiency). The organic phase contained Phl and MAPG and was evaporated to dryness and suspended in 3.0 ml of 35% (v/v) of acetonitrile (ACN);water both containing 0.1% trifluoroacetic acid (TFA). Crude extracts were filtered through 0.20 μm syringe filters, followed by C-18 reverse phase HPLC (Waters NOVA-PAK C-18 Radial-PAK cartridge, 4μm, 8×100 mm). The Waters HPLC system consisted of a 710B WISP, 510 pumps, and 680 automated gradient controller, with a 990 photo-diode array detector. HPLC solvent conditions were at a flow rate of 1.0 ml/min, with a 2 min initial condition at 10% ACN/water/0.1%TFA, followed by a 20 min linear gradient to 100% ACN/0.1% TFA. HPLC gradient profiles were monitored at the spectral peak maxima characteristic for Phl in the designated solvent system (270 nm, 330 nm). Phl eluted at a retention time of 17.02 min at approximately 78% ACN/0.1% TFA. Standard curves were run using complementary Phl-nonproducing strains, where cultures spiked with known concentrations of standard were subjected to the same extraction procedure described above. Seven point, extracted, standard curves were completely linear and reproducible yielding correlation coefficients ranging from 0.9997–0.9994.

TABLE 3

| Derivative | $A_{600}$ | μg/ml of culture | μg/g dry wt of culture | $μg/A_{600}$ |
|---|---|---|---|---|
| Q69c-80 (pPHL5122) | — | 8 | 0.33 | — |
| Q69c-80 (pVSP41) | — | n.d. | — | — |
| Q69c-80::mTN5 Phl 1 | 1.06 | 87 | 3.3 | 329 |
| Q69c-80::mTN5 Phl 2 | 1.09 | 59 | 2.6 | 213 |
| Q69c-80::mTn5 Phl 3 | 0.92 | 153 | 6.5 | 665 |
| Q69c-80::mTn5 Phl 4 | 1.96 | 0.4 | 0.03 | 0.7 |
| Q69c-80::mTn5 Phl 5 | 1.26 | 24 | 1.0 | 76 |
| Q69c-80::mTn5 Phl 6 | 1.21 | 34 | 1.5 | 111 |
| Q69c-80::mTn5 Phl 7 | 0.70 | 153 | 6.7 | 870 |
| Q69c-80::mTn5 Phl 8 | 1.10 | 40 | 1.7 | 146 |
| Q69c-80::mTn5 Phl 9 | 0.76 | 196 | 8.1 | 1,034 |
| Q69c-80::mTn5 Phl 10 | 0.83 | 143 | 6.3 | 690 |
| Q69c-80::mTn5 Phl 11 | 0.82 | 173 | 7.0 | 850 |
| Q69c-80::mTn5 Phl 12 | 1.05 | 32 | 1.3 | 121 |
| Q69c-80::mTn5 Phl 13 | 0.87 | 175 | 7.4 | 806 |
| Q69c-80::mTn5 Phl 14 | 0.76 | 91 | 4.0 | 483 |
| Q69c-80::mTn5 Phl 15 | 0.95 | 85 | 4.0 | 409 |
| Q69c-80::mTn5 Phl 16 | 0.98 | 87 | 4.0 | 352 |
| Q69c-80::mTn5 Phl 17 | 0.81 | 104 | 4.8 | 540 |
| Q69c-80::mTn5 Phl 18 | 0.71 | 149 | 6.4 | 832 |
| Q69c-80::mTn5 Phl 19 | 0.99 | 95 | 4.0 | 383 |
| Q69c-80::mTn5 Phl 20 | 0.83 | 97 | 4.5 | 465 |

Considerable variation was observed among individual strains in growth on yeast-malt broth, stability of the phenotype (there was a strong tendency to loss of red pigmentation and failure to produce detectable Phl), and amount of Phl produced (Table 3). Quantities of Phl sometimes were over twenty-fold greater than produced by Q69c-80 (pPHL5122), and Phl usually was not detectable in cultures of strain Q2-87 grown under comparable conditions (data not shown). These results suggest that expression of the transposed genes is deregulated, a hypothesis supported by DNA sequence data indicating that phlF, a putative repressor of Phl synthesis, is truncated and probably unable to repress phl gene expression in constructs containing the sequences shown in SEQ ID NO:4.

Example 2

Generation and characterization of mutants to delineate the size of the fragment capable of conferring Phl biosynthetic capability.

A restriction map of the DNA fragment cloned into pMON5122 was generated using the following restriction enzymes: BamHI, BstEII, ClaI, EcoRI, EcoRV, HindIII, PstI, PvuII, and SalI. This map revealed the cloned fragment to be 6.5 kb in size, and thus substantially smaller than the 9.5 kb value that was reported by Vincent et. al., supra. The relative positions of restriction sites were, however, sufficiently similar to those reported by Vincent et al. to suggest that Vincent's size estimate was in error, rather than that the maps were of two entirely different DNA segments.

That portion of the cloned fragment that is necessary to direct Phl biosynthesis was determined by mutating pMON5122 with the transposon Tn3HoHo1 (Stachel et. al., The EMBO J. 4:891–898 (1985)). Insertions of Tn3HoHo1 were obtained by transforming E. coli strain HB101(pHoHo/pSShe) with pMON5122. Transformants containing all three plasmids were subsequently mated with E. coli containing the conjugal helper plasmid pRK2013 and E. coli C2110, a nalidixic acid-resistant, polA-deficient recipient strain which does not support replication of pHoHo and pSShe. Donor, helper and recipient strains were spotted onto Millipore filters (1 cm$^2$) and incubated at 37° C. for 6 hours. The growth on the filters was suspended in 1 ml of sterile distilled water and 200 μl of this suspension was spread on LB agar containing tetracycline (to select for pMON5122), ampicillin (to select for those plasmids containing the transposed Tn3HoHo1 element) and nalidixic acid (selects strain C21 10). Transconjugants resistant to all three antibiotics were isolated in 18 sets of 48 on a grid. The site and orientation of insertion of the transposon in each pMON5122 derivative was analyzed by digestion of isolated plasmid DNA with EcoRI, and in triple digests with HindIII, BamHI and EcoRI. Of 846 mutants that were analyzed, 19% contained transposon insertions within the cloned fragment. Duplicate insertions giving rise to identical restriction fragments were obtained with high frequency in the left half of the fragment, whereas few insertions were obtained within the right end. In all, 43 unique insertions were analyzed further.

Those plasmids containing insertions within the cloned fragment then were introduced by triparental mating into M4-80R and tested for the ability to direct Phl biosynthesis by TLC and by the C. michiganensis subsp. michiganensis inhibition bioassay described in Example 1. The bioassay method (detection limit 250 ng) was more sensitive than TLC (detection limit about 1 μg) and therefore was chosen for evaluation of the effect of the various insertions on Phl synthesis by strain M4-80R carrying the mutated plasmids.

In Table 4, the value given for each insertion represents the percent decrease or increase in the size of the zone of inhibition on bioassay plates, relative to the positive control strain M4-80R(pMON5122) within one assay set. An assay set consisted of positive and negative controls and three different insertion derivatives of M4-80R(pMON5122). For each insertion, statistical comparisons were made only within assay sets by analysis of variance and Fisher's protected least significant difference test at p=0.05. ** indicates not significantly different from the positive control within the same assay set. * indicates % reduction of inhibition was intermediate between the positive and negative control (p=0.05) and the phenotype was Red$^-$. M represents the average value for the negative control across all assay sets.

TABLE 4

| Insertion | % Reduction | Insertion | % Reduction |
|---|---|---|---|
| 2 | 67 | 23 | 36 |
| 3 | 54 | 24 | 29 |
| 4 | 57 | 25 | 28* |
| 5 | 74 | 26 | 17 |
| 6 | 66 | 27 | 24 |
| 7 | 55 | 28 | 8** |
| 8 | 13** | 29 | 23 |
| 9 | 19** | 30 | −7** |
| 10 | 74 | 31 | 20** |
| 11 | 46 | 32 | 32** |
| 12 | 57 | 33 | 31* |
| 13 | 68 | 34 | 22 |
| 14 | 56 | 35 | 24 |
| 15 | 70 | 36 | 32 |
| 16 | 67 | 37 | 22 |
| 17 | 66 | 38 | 34 |
| 18 | 31 | 39 | 27 |
| 19 | 46 | 40 | 56 |
| 20 | 56* | 41 | 76 |
| 21 | 36** | 42 | 80 |
| 22 | 32 | 43 | 68 |
|  |  | M | 72 |

M4-80R containing derivatives of pMON5122 with insertions at positions 2 through 7 and 10 through 18, located within a 5-kb region at the right end of the fragment shown in FIG. 2, were significantly less inhibitory of C. m. michiganensis than was M4-80R(pMON5122), indicating partial or full loss of Phl production (Table 4). Insertion derivatives 8 and 9, which map to approximately the same site but contain Tn3HoHo1 in opposite orientations, enabled levels of *C. m. michiganensis* inhibition that were not significantly different from those of M4-80R(pMON5122), the positive control. Insertion derivative 8 was, however, $Lac^+$ indicating no break in transcription. Insertion derivatives 34 through 39 at the left end of the fragment shown in FIG. 2 were not significantly less inhibitory than the positive control. Thus, only the sequences within the 5-kb region at the right end of the fragment were required for inhibition of the indicator organism and for production of Phl.

Strain M4-80R containing the various pMON5122::Tn3 HoHo1 derivatives also was evaluated visually for the presence of the red pigment after 4–7 days in YM broth or on KMB agar plates. Whereas all insertions up to and including number 18 that were Phl were also $Red^-$, insertions downstream of number 18 exhibited other phenotypes. Most of these insertions had no effect on the presence of the red indicator pigment. However, insertion derivatives 20, 25, and 33 were $Red^-$ and had a level of inhibition of *C. m. michiganensis* intermediate between the positive and negative controls (FIG. 2, Table 4). The region encompassing these insertions was therefore designated "Red" in FIGS. 1, 2, and 3. While not required for Phl production, it clearly is involved in Phl production or activity.

Example 3

Determination of size, orientation and number of potential transcriptional units within the fragment required for Phl biosynthesis.

The M4-80R(pMON5122::Tn3HoHo1 ) derivatives described in Example 2 were evaluated for expression of the lacZ gene carried on the transposon Tn3HoHo1 to determine the presence, number, size, and orientation of the transcriptional units within the mutated sequences. Expression of the lacZ gene in each derivative was detected by the development of blue colored colonies on LB medium containing 5-bromo4-chloro-3-indolyl-β-D-galactoside (X-gal). Results of this analysis are indicated in FIG. 2. In strain M4-80R, all insertions which resulted in expression of lacZ, except three, were oriented in the same direction; only the $Lac^+$ insertions 2 and 3 at the right end and insertion 38 at the left end of the locus were oriented in the opposite direction. These results indicate the presence of at least two divergent transcriptional units. The long unit running from right to left continues past the region strictly necessary for the biosynthesis of Phl and into the Red region. The smaller unit running from left to right also extends beyond the fragment present in pMON5122.

Reporter derivative strains of Q2-87::Tn3HoHo1-15 and Q2-87::Tn3HoHo1-40 were generated by introducing two of the Tn3HoHo1 insertions (15 and 40) into the Q2-87 chromosome by a process called marker exchange, which occurs due to spontaneous recombination between the sequences on the plasmid flanking the Tn3HoHo1 insertion and homologous sequences in the chromosome. In practice, such process is directed by the hand of man and the desired result is identified by man.

Strain M4-80R carrying pMON5122::Tn3HoHo1 derivatives 15 and 40 were inoculated into LB broth without tetracycline; after incubation overnight at room temperature, 100 μl of the culture was transferred to fresh LB broth. After a second such transfer, serial dilutions of the culture were prepared and 200 μl of each was plated on LB agar containing (X-gal). Cells in which homologous recombination had taken place gave rise to blue colonies, and could no longer grow on LB agar containing tetracycline. The reporter lacZ gene introduced into Phl locus in the chromosome of Q2-87 provides a simple means of monitoring Phl gene expression either visually, as colony color on LB agar containing X-gal, or quantitatively, with a β-galactosidase assay readily accessible to those in the art.

Example 4

Analysis of the region including the Phl biosynthetic genes.

FIG. 1 depicts the genetic organization of the 7-kb region which encompasses the entire region known to be involved in Phl production. A variety of subclones were prepared as double-stranded templates for automated sequencing by digestion of the 6.5-kb fragment from pMON5122 with various restriction endonucleases, either singly or in combination, followed by ligation with the cloning vector pIC19H (Marsh, et. al., *Gene* 32:481–485 (1984)) (FIG. 3). A fragment of DNA which overlaps the right end of the pMON5122 fragment also was cloned from pMON5120 to determine the end point of phlF (FIG. 3).

Sequences were determined at the Nucleic Acid Research Facility at Iowa State University with an ABI automated sequencer. Sequence analysis was performed with the University of Wisconsin Genetics Computer Group (GCG) software (Staden, et. al., Program Manual for the GCG package, Version 7.2 (Incremental Release—Documentation Updates), October 1992, 575 Science Drive, Madison, Wis., USA 53711 (1992)). The program MAP was used to predict potential open reading frames in the sequence which was further supported by the results of the program CODONPREFERENCE using the Pseudomonas codon preference table. The program TRANSLATE was used to translate the open reading frames into protein sequences. The coordinates of the open reading frames in SEQ ID NO:3 are as follows:

| | | |
|---|---|---|
| phlA | 4285–5076; | transcribed from right to left |
| phlB | 2606–3313; | transcribed from right to left |

| | | |
|---|---|---|
| phlC | 3085–4251; | transcribed from right to left |
| phlD | 1398–2444; | transcribed from right to left |
| phlE | 2–1270; | transcribed from right to left |
| phlR | 3514–4767; | transcribed from left to right |
| phlF | 5781–6386; | transcribed from left to right |

The coordinates of the truncated phlF open reading frame in SEQ ID NO:4 are as follows:

phlF (truncated) 5781–6170; transcribed from left to right

Protein sequences were compared to known proteins from all organisms within the NCBI database using the program BLAST (Altschul et. al., *J. Mol. Biol.* 215:403–410 (1990)). The predicted proteins were analyzed for the presence of characteristic sequence motifs using the program MOTIFS and the PROSIE database (Bairoch, Nucleic Acids Res. 19:2241–2245 (1991)). This analysis has led so far to the genetic organization of the fragment shown in FIG. 1 as well as potential functions for some of the predicted proteins.

The significance of the similarity of a predicted protein to known proteins is determined by calculating the binary comparison score (Z-score), which is measured in standard deviations. To have significant similarity the score must be 3 or greater. A value of 6 or greater corresponds to a probability of about $10^{-9}$ that the degree of similarity seen in the two sequences arose by chance. Values in this range suggest a common origin by divergent evolution but do not rule out convergent evolution. When a score is greater than 9 the degree of similarity is considered to be too great to have arisen by chance or for the proteins to have evolved convergently so the sequences are considered to be homologous.

phlA predicted PhlA, a protein of 264 amino acids that has no similarity to any proteins in the database but that shows partial conservation (mismatch=1) of a short chain alcohol dehydrogenase family signature, an ornithine/diaminopimelic acid/arginine decarboxylase family signature and a phosphopantetheine attachment site.

Short-chain alcohol dehydrogenase family signature

```
                     *   #
    Consensus     Y(A)(G)(A)K x(A)(A)x{2}(L)
                  | |  |  |  | |  |  |   |
    PhlA          Y A  G  A  G A  A  A L L L
```

* – marks the tyrosine residue important for catalytic activity and/or substrate binding

– marks the lysine residue to which the pyridoxal phosphate binds; it is replaced by a glycine residue in PhlA.

Ornithine/Diaminopimelic acid/Arginine decarboxylase family signature

```
                              ***
    Consensus     (S)x{2}(F)(S)(L)GGG(L)(G)
                   |  |   |  |  |   |  |  |
    PhlA          S T P   F  S  L GKG L  G
```

* – marks the three glycine residues proposed to be part of a substrate-binding region.

Phosphopantetheine attachment site

```
                              *
    Consensus     (I)G(A)(D)S(I)x{3}(T)x{4}(L)
                   | |  |  . |  |   |    |   |
    PhlA          I G A  D T I N RN T APGD L
```

* – marks the serine to which the phosphopantetheine moiety is attached via its hydroxyl moiety. In PhlA this serine is replaced by threonine which has a similar reactive hydroxyl moiety.

Symbols:
| – represents identical residue;
: – represents conservative replacement;
. – represents semi-conservative replacements based on the similarity scores assigned in a PAM120 matrix.

Short chain alcohol dehydrogenases catalyze the reversible oxidation of an alcohol to an aldehyde and are involved in many types of biosynthetic reactions. For example, in bacteria, acetoacetyl-CoA reductase (a member of the short-chain alcohol dehydrogenase family) in *Zooglea ramigera* and *Alcaligenes eutrophus* (Persson, et. al., *Eur. J. Biochem.* 200:537–543(1991)) is involved in the biosynthesis of poly-β-hydroxybutyrate. Ornithine, arginine and diaminopimelic acid decarboxylases are enzymes that act in the biosynthesis of polyamines and lysine, respectively. Phosphopantetheine is the prosthetic groups of acyl carrier proteins (ACP) in some multienzyme complexes where it serves as a "swinging arm" for the attachment of activated fatty and amino acid groups.

phlB predicted protein PhlB, of 236 amino acids. PhlB did not show similarity to any known protein in the database nor did it show conservation of any common protein signatures. PhlB therefore may be a unique, as yet unidentified protein.

phlC predicted PhlC, a protein of 389 amino acids with 27.9% identity and 49.7% similarity to the N-terminal portion of mammalian peroxisomal sterol carrier protein X (SCPx); the Z score for the two is 15; i.e., it is homologous to SCP-X. The 400 N-terminal amino acids of SCPx function as a 3-oxoacyl-CoA thiolase (Seedorf et. al., *J. Biol. Chem.* 269:21277–21283 (1993)); a hypothetical substrate binding site containing a cysteine residue and a glycine-rich C-terminal domain are conserved (FIG. 5; Ossendorp et. al., *Eur. J. Biochem.* 201:233–39 (1991)).

Putative substrate binding site:

```
                                           *
    Rat SCPx      78  SLGLTGIPIINVNNNCSTGST
                      .||:.. |.:  ..||..:|.
    PhlC          73  ALGISPAPTFMSTANCTSSSV
```

* – marks the reactive cysteine residue.

```
    Rat SCPx     343  NPSGGLISKGHPLGATGLA
                      |..|| |::||:  |..|:
    PhlC         337  NTDGGNIGRGHASGCDGIL
```

Symbols:
| – represents identical residue;
: – represents conservative replacement;
. – represents semi-conservative replacements based on the similarity scores assigned in a PAM120 matrix.

The thiolase domain of SCPx efficiently catalyzes the thiolytic cleavage of a wide variety of 3-oxoacyl-CoA substrates, with preference for medium-length substrates; it is hypothesized to supply acetyl-CoA for anabolic reactions when cells are well-supplied with energy (Seedorf et. al., *J. Biol. Chem.* 269:21277–21283 (1993)). Thus, PhlC may provide a source of starter units for the synthesis of Phl. Alternatively, thiolases share conserved residues in their condensing domains with β-ketoacyl synthases and chalcone synthases (M. Siggard-Andersen, *Protein Seq. Data Anal.* 3:325–335 (1993)), and the similarity we have detected between PhlC and SCPx may be consistent with activity analogous to chain elongation in fatty acid and polyketide synthesis.

phlD predicted a protein, PhlD, of 349 amino acids with 27.9% identity and 48.0% similarity to members of the chalcone synthase/stilbene synthase (CHS/STS) family of enzymes from higher plants. Randomized binary comparisons of the amino acid sequences of PhlD and CHS from tomato gave a Z-score of 19.5. Thus, PhlD is homologous to chalcone synthases from plants.

PhlD contained regions with extensive similarity to the active site and signature sequence domains of CHS/STS enzymes (FIG. 6), but had surprisingly little similarity to prokaryotic p-ketoacyl synthases, including those that catalyze similar condensing reactions (e.g., polyketide synthesis by actinomycetes) in bacteria. It is, to our knowledge, the first prokaryotic protein to show such extensive similarity to the CHS/STS protein family. These observations, and the apparent functional and biochemical parallels between plant defense by Phl-producing plant-associated microorganisms and plant self-defense mediated by phytoalexins (products of CHS/STS enzymes), provoke speculation as to possible gene exchange between plants and their bacterial colonists or more likely, a common evolutionary origin for these two mechanisms of defense.

Chalcone synthases function as polyketide synthases to catalyze condensation reactions. For example, the CHS from *Lycopersicon esculentum* catalyzes the sequential addition of 3 acetyl units from malonyl-CoA to the phenylpropanoid ring of 4-coumaroyl-CoA and cyclization of the enzyme-bound intermediate to form naringenin chalcone, the central intermediate in the biosynthesis of many flavonoids. CHS accepts aliphatic-CoA esters as starter molecules, and acylphloroglucinols have been recovered as by-products of chalcone synthesis in vitro. This suggests that PhlD may be sufficient to catalyze the condensation and/or cyclization reactions required for MAPG synthesis (FIG. 4).

phlE predicted PhlE, a protein of 423 amino acids, that had 24.1% identity and 49.7% similarity to *Staphylococcus aureus* norA protein, a multidrug efflux transporter that contributes to fluoroquinone resistance. The Z score for the two proteins was 10.8. NorA and other such proteins are members of a very large superfamily of transmembrane solute facilitators that extends throughout prokaryotes, cyanobacteria, lower eukaryotes and higher plants and animals. Transporters specific for simple sugars, oligosaccharides, organic acids, organophosphate esters and drugs have been identified; among the most well-known representatives of the drug efflux subfamily are the tetracycline-$H^+$ antiporters driven by proton motive force. PHIE retained conserved structural features of these integral membrane permeases (FIG. 7), including a central hydrophilic loop bordered on either side by six hydrophobic α-helices.

The region designated Red based on the results of Tn3HoHo1 mutagenesis (see Example 2) includes phlE. The homology between PhlE and known multidrug efflux proteins suggests that PhlE may function to export Phl from the cell, where it can react with media constituents or oxygen to produce the red pigment. That export occurs under native conditions is indicated by the fact that Phl is recovered in significant quantity from culture media (Table 3). Phloroglucinol (unacetylated) can condense with the coniferaldehyde moiety of lignin compounds from plants to give a reddish color; the reactive group here is the carbonyl of the aldehyde. Such reactive carbonyl groups may be present on compounds naturally present in media, or may be produced in media by growth of the Phl-producing bacteria.

phlR predicted protein PhlR, of 418 amino acids. PhlR did not show similarity to any known proteins in the database but showed partial conservation (mismatch 1) of the thiolases 3 signature sequence.

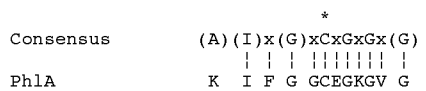

```
                              *
Consensus         (A)(I)x(G)xCxGxGx(G)
                   |  | |  ||||||| |
PhlA               K  I F G GCEGKGV G
```

\* - marks the active site cysteine residue
   involved in deprotonation in the condensation
   reaction.
Symbols:
| - represents identical residue;
: - represents conservative replacement;
. - represents semi-conservative replacements based
   on the similarity scores assigned in a
   PAM120 matrix. Type II thiolases are involved
   in the thiolysis of acetoacetyl-CoA and in
   biosynthetic pathways such as poly-β-hydroxy-
   butyrate synthesis and steroid biogenesis.

phlF predicted PhlF, a protein of 202 amino acids with 23% identity and 47% similarity to tetracycline repressor protein. Conservation was concentrated within a helix-turn-helix (HTH) domain typical of known DNA-binding regulatory proteins such as λ cro and repressor proteins, phage 434 cro and repressor proteins, lac repressor, catabolite reactive protein (CRP), and *E. coli* tetracycline repressor protein. The HTH score obtained by using the Helix-Turn-Helix program in the EGCG package (Rice, P., Computer Group, European Molecular Biology Laboratory, PostFach 10–2209, 69012 Heidelberg, Germany) was higher for PhlF than were the scores for λ cro and repressor proteins and the phage 434 cro and repressor proteins. This score is a measure of the probability that the amino acid sequence predicts a functional DNA-binding domain, and strongly supports a role for PhlF in the regulation of gene expression.

It is known that deletions of the Tn10 and class E tetR tetracycline repressor genes resulting in truncation of the carboxy-terminal end of the encoded repressor proteins are derepressed in expression of the tetracycline resistance protein. The very high levels of Phl produced by transformed derivatives of *P. fluorescens* Q69c-80 containing a single chromosomal copy of a fragment including the truncated phlF gene and the phlACBDE and phlR genes (Table 3) argues that the phlF gene is a repressor of phl gene expression, and that truncation of PhlF permits derepressed synthesis of Phl in a manner analogous to that reported in the tetracycline resistance operon. The fact that pMON5120, containing the intact phlF gene, does not transfer Phl biosynthetic capability to the nonproducer strain M4-80R further strengthens this argument.

Subcloning experiments are performed with the objective of determining whether the intact phlF gene is sufficient to repress expression of phl biosynthetic genes. The phlF gene is cloned in its entirety from pMON5120 on an EcoRV fragment, BamHI adapters are ligated to the ends, and the fragment is cloned into the BamHI site in pRK415, a broad host-range vector that can be maintained in Pseudomonas strains. This construction is introduced into Q2-87::Tn3HoHo1-15 and Q2-87::Tn3HoHo1-40, reporter strains in which Tn3HoHo1 transposon insertions 15 (in phlD) 40 (in phlA) have been introduced into the chromosome of Q2-87 by marker exchange (homologous recombination). The BamHI fragment is sufficient to repress expression of phlA and phlD, as indicated by loss of blue colony color on media containing the chromogenic substrate X-gal, or by failure to detect 6-galactosidase activity in a standard enzyme assay known to those skilled in the art. In contrast, introduction of pRK415 alone causes no change in colony color.

Most of the proteins predicted by each of the phl genes showed similarities to proteins with known functions. However, since the pathway for synthesis of Phl in Pseudomonas is at present unknown, and because the identified sequence simiarities are to proteins other than those known to catalyze polyketide biosynthetic reactions in bacteria (such as actinomycetes), the actual role of the predicted proteins in Phl synthesis is yet to be determined. The cloned genes described herein permit fundamental studies on the mechanism of Phl biosynthesis in Pseudomonas spp. by providing information and materials for the generation of clones to express individual phl genes and to analyze the activities and roles of their products in the biosynthesis of Phl.

Example 5

The native promoters for phlF and for phlA, phlB, phlC, phlD and phlR are contained within SEQ ID NO:4.

The majority of the Tn3HoHo1 insertions in M480R (pMON5122::Tn3HoHo1) derivative strains that were Lac⁺ were oriented from right to left; only insertions 2, 3 and 38 were oriented from right to left (FIG. 2). The lac promoter in the vector pRK415 is located distal to the left end of the cloned fragment as shown in FIG. 2 and could direct expression of the lacZ gene only in M4-80R (pMON5122::Tn3HoHo1-38). Expression of the lacZ genes in the remaining Tn3HoHo1insertions therefore must be driven from promoters other than those in the vector. There were two sets of such insertions, one including those numbered 4, 5, 6, 8, 10, 14, 15, 16, 18, 19, 20, 21, 23, 24, 27, 28, 31, 32, 34, 37, and 39 in FIG. 2, and the other including insertions 2 and 3. As these two sets of insertions are divergently oriented, the cloned fragment illustrated in FIG. 2 must contain at least two divergently oriented transcriptional units and two promoters situated between phlA and phlF that are the native promoters of these genes.

That this region carried promoter sequences was supported by the nature of its sequence. There were few or no open reading frames, and the sequence was very high in the bases A and T, which is characteristic of promoter sequences.

Example 6

Cloning of the phlD gene and expression of its gene product.

a. Cloning of phlD. The phlD gene is cloned as follows based on results of sequence analysis: the 5' end of phlD is cloned as a AccI-SalI fragment into pIC19H cut with ClaI and SalI. The remaining 3' portion of the phlD is then introduced into the SalI site to regenerate the entire phlD gene in plasmid pPHLD. The cloned fragment from pPHLD is isolated as a HindIII fragment and cloned into pTrcHis expression vectors A, B, and C (Invitrogen) to express the PhlD protein for assays of enzyme activity. The fragment is also cloned into the broad host range vector pRK415, and the resulting construction is introduced into Q2-87:Tn5-1 by triparental mating to determine if it is sufficient to complement the mutation in the chromosomal phlD gene. The transconjugant so generated is tested for Phl biosynthesis by production of red pigment, bioassay, and extraction of Phl and MAPG.

b. Expression of phlD and assay of enzymatic activity of expressed protein. S For the preparation of active enzyme, the cells are grown, expression is induced, and the protein is isolated according to manufacturer's instructions. To assay enzyme activity, mix 15 μl of the isolated enzyme, 75 μl of buffer (0.2 M Hepes/KOH (Ph 7.0), 1 mM EDTA), 5 μl of starter unit (e.g., 4-acetoacetyl-CoA or acetyl-CoA (1 nmol)), and 5 μl of extender unit (e.g., [2-14C]malonyl-CoA (1.5 nmol, 0.78 GBq/mmol, Amersham Corp.). Incubate 30 min at 37° C.; stop reaction by two sequential extractions with 0.15 ml of ethyl acetate. The solvent is removed by evaporation under vacuum (Speedvac), and the residue is dissolved in 10 μl ethyl acetate and analyzed by TLC in 15% acetic acid. Negative control samples spiked with Phl and/or MAPG are used to quantitate the efficiency of recovery (Lanz et al., *J. Biol. Chem.* 266:9971–9976 (1991)). Detection is by scintillation counting of samples scraped from the TLC plate.

Cerulenin binds to the active site cysteine of condensing enzymes and is known to inhibit the activity of chalcone synthases. For cerulenin inhibition assays, cerulenin is dissolved in ethylene glycol monomethyl ether. Reactions mixes (as above) are pre-incubated with this solution for 10 min at 25° C. before starting the reaction by adding substrates.

Example 7

Intact phlD is necessary for Phl synthesis.

The Tn5 insertion in Q2-87:Tn5-1 is located with phlD; this mutation completely eliminates production of Phl as well as MAPG, suggesting that phlD is essential for the production of Phl. The BamHI-ClaI fragment that encodes the 293 amino acids at the 3' end of the 349 amino acid PhlD protein was cloned into pIC19H, excised as HindIII fragment, cloned in both orientations into the broad-host range vector pRK415 and introduced into Q2-87:Tn5-1 and into strain M4-80R by triparental mating. In either orientation the cloned fragment was unable to complement the mutation in Q2-87:Tn5-1 and did not direct Phl synthesis in M4-80R. Thus, intact PhlD is necessary for Phl synthesis.

Example 8

Improvement of biocontrol capability of strains transformed with DNA sequences that confer of enhance Phl production.

a. Preparation of *Gaeumannomyces graminis* var. *tritici* inoculated soil. Isolates of *G. g. tritici* were stared from single ascospores from the roots of diseased wheat plants. The isolates were maintained on fifth-strength potato dextrose agar (PDA) (Duffy and Weller, *Phytopathology* 84:1407–1415 (1994)). To prepare *G. g. tritici* inoculum, an isolate was grown for 5–7 days on PDA in petri plates and then transferred as mycelium and accompanying agar medium to a 1-liter flask containing autoclaved oat kernels. Two hundred fifty cc of oat kernels per flask plus 125 ml of water were autoclaved at 121° C. for 90 min on each of two consecutive days. The flasks were incubated at 25° C. until the fungus colonized the oat kernels (about 3 wk). The oats were shaken once during the incubation period. After colonization, the oat kernels were removed from the flasks, dried and stored. The inoculum was pulverized using a Waring blendor and sieved to obtain particles 0.25–0.5 mm in size. *G. g. tritici* inoculum was added to either steamed Ritzville silt loam or raw Puget silt loam (Pierson and Weller, *Phytopathology* 84:940–947 (1994)).

b. Preparation of bacterial treated seeds. Wheat seeds were surface-sterilized by immersion in a 2.6% solution of sodium hypochlorite for 2 min followed by a 10 min rinse under a stream of water and a final rinse of sterile water. Seeds were dried in a stream of sterile air. Wild-type strains (Q2-87, Q65c-80, and Q69c-80), strains transformed with Phl biosynthetic genes carried on the plasmid pVSP41 [(Q2-87(pPHL5122), Qc65(pPHL5122), and Q69c-80 (pPHL5122)], strains bearing only the plasmid vector [Q65c-80(pVSP41) and Q69c-80(pVSP41)] and strain Q69c-80 transformed by Phl biosynthetic genes carried on a mini-transposon (Q69c-80::mTn5PHL12, Q69c-

80::mTn5PHL15 and Q69c-80::mTn5PHL20) were cultured individually into 250-ml flasks containing 25 ml of nutrient broth yeast extract broth (Bacto-nutrient broth, 8 g; Bacto-yeast extract, 2 g; $K_2HPO_4$, 2 g $KH_2PO_4$, 0.5 g; $MgSO_4$ $7H_2O$, 0.25 g; glucose, 5 g; $H_2O$, 1000 ml) Vidaver, (*Appl. Microbiol.* 15:1523–1524 (1967)) for 72 hr, centrifuged at 5,000 rpm for 10 min at 4° C., and suspended in 3 ml of 0.5% (w/w) of methylcellulose. Six grams of the surface-sterilized seeds were poured into the bacteria-methylcellulose mixture, shaken and then dried under a stream of sterile air. Seeds became coated with populations ranging from 4.0–9.0 log cfu/seed depending on the strain. A wide variety of microbiological media (both solid and liquid) can be substituted to culture the bacteria and a wide variety of compounds can be substituted to formulate the bacteria and to apply them to the seeds (PCT Application WO 94/01561).

c. Growth chamber test using bacteria-treated seeds. Tests of bacterial strains and controls (nontreated seed or seed treated with methylcellulose) were conducted similar to tests reported by Ownley et al. (*Phytopathology* 82:178–184 (1992)). The test used plastic tubes (2.5-cm diameter×16.5-cm long) held upright in plastic racks. The bottom of each tube was plugged with cotton and filled with a 6.5-cm-deep layer of sterile vermiculite overlaid with 10 g of soil amended with *G. g. tritici* oat kernel inoculum. Two wheat seeds treated with a bacterial strain or control seeds were sown per tube and covered with vermiculite. Each tube received 10 ml of water. The cones were incubated at 15–18° C. for 34 weeks with a dark/light cycle of 12 hr and watered twice per week with 5 ml of dilute (1:3, v/v) Hoagland's solution (macroelements only) (Hoagland and Arnon, *J. Cal. Agr. Exp. Stat. Circ.* 347 (1950)). Each treatment was replicated five times, and each replicate consisted of a row of 10 separate tubes (20 individual plants). Treatments were arranged in racks in a randomized complete block design. After incubation, seedlings were removed from the soil, washed with water and evaluated on the basis of overall take-all severity and the number of root lesions using the following criteria. Overall take-all severity was measured on a scale of 0 (no disease) to 8 (plant nearly dead) as described by Ownley et al., (*Phytopathology* 82:178–184 (1992)). The severity of root disease (root disease index) was measured on the sections of the roots 3 cm or greater from the seed using a scale of 0–4, where 0=no take-all lesions, 1=up to 25% of the roots infected, 2=26%–50% of the roots infected, 3=51%–75% of the roots infected and 4=over 75% of roots infected. Disease rating was compared statistically among treatments by an analysis of variance (ANOVA). Treatment means were compared by a least significant differences test (LSD) when significant differences among treatments was indicated by the ANOVA (Fisher's protected LSD). Differences among treatments were determine based on a probability level of P=0.05. Table 5 shows the enhanced biocontrol of take-all achieved by insertion of the DNA sequences that code for Phl production. For example, strain Q2-87 (pPHL5122) had a significantly lower root disease index score than Q2-87. Strain Q65c-80(pPHL5122) had a significantly lower overall disease severity rating than Q65c-80 or Q65c-80(pVSP41). Strain Q69c-80(pPHL5122) had a significantly lower overall disease severity rating than the wild-type strain Q69c80 or Q69c-80(PVSP41). There was no soil x treatment interaction, therefore data from the raw Puget silt loam and pasteurized Ritzville silt loam were pooled.

TABLE 5

| Seed treatment | PM produced | Log cfu /seed | Overall disease severity | Root disease index |
|---|---|---|---|---|
| Non treated | | | 3.56 a[z] | 2.01 a[z] |
| Methylcellulose | | | 3.53 a | 1.94 a |
| Q2-87 | + | 7.9 | 3.09 b | 1.22 b |
| Q2-87(pPHL5122) | ++ | 5.6 | 3.03 b | 0.89 c |
| Q65c-80 | + | 8.4 | 3.03 b | 0.63 d |
| Q65c-80(pPHL5122) | ++ | 8.0 | 2.75 cd | 1.22 b |
| Q65c-88(pVSP41) (vector) | + | 7.8 | 2.97 b | 1.30 b |
| Q69c-80 | – | 8.5 | 2.95 bc | 1.39 b |
| Q69c-80(pPHL5122) | ++ | 8.8 | 2.61 d | 1.19 b |
| Q69c-80(pVSP41) (vector) | – | 9.1 | 2.93 bc | 1.35 b |

[z]Means in the same column followed by the same letter are not significantly different at P = 0.05 according to Fishers' protected least significant difference test (LSD).

Table 6 shows that DNA sequences that code for Phl production, when stably inserted into the genome of the recipient strain, conferred on the recipient strain the ability to suppress take-all at a substantially lower bacterial dose on the seed as compared to the wild-type strain. For example, strains Q69c-80::mTn5PHL112, Q69c-80::mTn5PHL115 and Q69c-80::mTn5HL20 applied at doses that were approximately 10,000-fold, 10,000-fold and 100-fold less, respectively than the dose of the wild-type strain Q69c-80 provided the same level of take-all suppression as Q69c-80. This is important because each 10-fold reduction in the dose of the bacterial treatment results in a substantial reduction in the cost of the biocontrol treatment to the farmer. There was no soil x treatment interaction, therefore data for the raw Puget silt loam and pasteurized Ritzville silt loam were pooled.

TABLE 6

| Seed treatment | Phl produced | Log cfu /seed | Overall disease severity |
|---|---|---|---|
| Methylcellulose | | | 3.89 a[z] |
| Q69c-80 | – | 8.6 | 3.03 b |
| Q69c-80::mTn5Phl12 | ++ | 4.1 | 3.16 b |
| Q69c-80::mTn5Phl15 | ++ | 4.4 | 3.19 b |
| Qc69c-80::mTn5Phl20 | ++ | 6.1 | 2.95 b |

[z]Means in the same column followed by the same letter are not significantly different at P = 0.05 according to Fishers' protected least significant difference test (LSD).

Example 9

Field testing of strains transformed with DNA sequences that confer of enhance Phl production.

a. Preparation of bacterial treated seeds. Wild-type strains Q2-87, Q65c-80, and Q69c-80), strains transformed with Phl biosynthetic genes carried on the plasmid pVSP41 [(Q2-87(pPHL5122), Qc65(pPHL5122), and Q69c-80 (pPHL5122)], strains bearing only the plasmid vector [Q65c-80(pVSP41) and Q69c-80(pVSP41)] and strain Q69c-80 transformed by Phl biosynthetic genes carried on a mini-transposon Q69c80::mTn5PHL15 and Q69c-80::mTn5PHL20) are propagated for 48–72 hr individually on agar plates of King's Medium B (Proteose peptone, 20 g; $K_2HPO_4$, 1.5 g; $MgSO_4$ $7H_2O$, 1.5 g; glycerol, 10 g; agar, 17 g; $H_2O$, 1000 ml) (King et al., *J. Lab. Clin. Med.* 44:301–307 (1954)). The bacteria are scraped from the plates and suspended in 1.0% methylcellulose. Bacteria are mixed with seed at a rate of approximately one petri plate of bacteria and 4.0 ml of methylcellulose per 20 g of seed.

Coated seeds are air dried and contain approximately 4.0–8.5 log cfu/seed depending on the strain. A wide variety of microbiological media (both solid and liquid) can be substituted to culture the bacteria and a wide variety of compounds can be substitute to formulate the bacteria and apply them to the seeds (see PCT Application WO 94/01561).

Strains are tested in fields in which *G. g. tritici* is introduced as oat kernel inoculum. Treatments are arranged in a highly modified randomized complete block design as described by Pierson and Weller (supra). Seed treatments and control treatments each are sown in three 3.1-m rows. *G. g. tritici*, as whole oat kernel inoculum is introduced into the furrow immediately before the seed is sown by hand. Controls include methylcellulose-treated seed with *G. g. tritici* inoculum in the furrow, nontreated seed with *G. g. tritici* in the furrow, and nontreated seed without *G. g. tritici*. Strains also are tested in fields that are naturally infested with *G. g. tritici*. In such tests, controls consist only of nontreated seed and methylcellulose treated seed. The severity of take-all is assessed on the basis of plant height, the number of heads, the amount of root disease and the grain yield.

Example 10

Use of strains transformed with DNA sequences that confer or enhance Phl production to suppress take-all in commercial wheat fields.

Bacterial strains transformed with Phl-biosynthetic sequences are cultured as described in Examples 8 and 9 or by any commercial method of bacterial mass rearing and are applied to wheat seed directly or introduced into the seed furrow, for example as a spray at log 6–9 cfu/ml, at the time of planting in fields infested with *G. g.* var *tritici* in order to suppress take-all. Field preparation and seeding follows standard commercial practices and uses standard commercial equipment. The effectiveness of the bacterial treatment is determined as described in Example 9.

Example 11

Use of strains transformed with DNA sequences that confer or enhance Phl production to suppress pathogens of wheat and barley in fields.

Bacterial strains transformed with Phl-biosynthetic sequences, cultured as described in Examples 8 and 9, are applied to wheat or barley seed directly or introduced into the seed furrow at the time of planting in field infested with any wheat pathogen, for example, those belonging to the genera Gaeumannomyces, Pythium, Fusarium, Rhizoctonia, Tilletia, Urocystis, Cephalosporium, Microdochium, Typhula.

Example 12

Use of strains transformed with DNA sequences that confer or enhance Phl production to suppress pathogens that cause seed rot, damping-off, blights, root rots, wilts and crown rots of crops grown from seeds, cuttings or seedpieces.

Bacterial strains transformed with Phl-biosynthetic sequences are cultured as described in Examples 8 and 9 and applied to seeds, cuttings, and seedpieces of crops infected with any pathogens, for example belonging to the genera Fusarium, Rhizoctonia, Pythium, Phytophthora, Verticillium, Septoria, that cause seed rot, damping-off, blights, root rots, wilts and crown rots.

We claim:

1. A nucleic acid consisting of a Phl protein-encoding region linked to one or two heterologous nucleotide sequences, wherein the Phl protein is selected from a group consisting of a *Pseudomonas fluorenscens* PhlA, PhlB, PhlC, phlD, PhlE, PhlF, and PhlR.

2. A nucleic acid according to claim 1, wherein the Phl protein is a Pseudomonas PhlA.

3. A nucleic acid according to claim 1, wherein the Phl protein is a Pseudomonas PhlB.

4. A nucleic acid according to claim 1, wherein the Phl protein is a Pseudomonas PhlC.

5. A nucleic acid according to claim 1, wherein the Phl protein is a Pseudomonas PhlD.

6. A nucleic acid according to claim 1, wherein the Phl protein is a Pseudomonas PhlE.

7. A nucleic acid according to claim 1, wherein the Phl protein is a Pseudomonas PhlF.

8. A nucleic acid according to claim 1, wherein the Phl protein is a Pseudomonas PhlR.

9. A nucleic acid according to claim 1, wherein the Phl protein comprises an amino acid sequence selected from a group consisting of SEQ ID NOS:6, 8, 10, 12, 14, 16, 18 and 20.

10. A nucleic acid consisting of a *Pseudomonas fluorenscens* phl gene selected from a group consisting of a phlA, phlB, phlC, phlD, phlE, phlF, and phlR, wherein the phl gene is linked to one or two heterologous nucleotide sequences.

11. A nucleic acid according to claim 10, wherein the phl gene is a phlA.

12. A nucleic acid according to claim 10, wherein the phl gene is a phlB.

13. A nucleic acid according to claim 10, wherein the phl gene is a phlC.

14. A nucleic acid according to claim 10, wherein the phl gene is a phlD.

15. A nucleic acid according to claim 10, wherein the phl gene is a phlE.

16. A nucleic acid according to claim 10, wherein the phl gene is a phlF.

17. A nucleic acid according to claim 10, wherein the phl gene is a phlR.

18. A nucleic acid according to claim 10, wherein the phl gene comprises a nucleotide sequence contained within SEQ ID NO: 3.

19. A nucleic acid according to claim 10, wherein the phl gene comprises a nucleotide sequence selected from a group consisting of SEQ ID NOS: 5, 7, 9, 11, 13, 15, 17 and 19.

20. A nucleic acid consisting of a *Pseudomonas fluorenscens* phl gene locus selected from the group consisting of:
   (a) the SalI-EcoRI fragment of pPHL5122;
   (b) the SalI-BamHI fragment of pMON5120; and
   (c) a nucleotide sequence selected from the group consisting of SEQ ID NO: 1, 2, 3 and 4, wherein the phl locus is linked to one or two heterologous nucleotide sequences.

21. A phl gene probe consisting of a nucleotide sequence selected from a group consisting of SEQ ID NOS: 1,2, 5, 7, 9, 11, 13, 15, 17 and 19, or a fragment thereof at least 18 nucleotides in length and which hybridizes to the complementary strand of the corresponding SEQ ID NO: 1, 2, 5, 9, 11, 13, 15, 17 or 19 under high stringency wash conditions.

22. A phl gene probe according to claim 21, wherein the nucleotide sequence is SEQ ID NO; 1, or a fragment thereof.

23. A phl gene probe according to claim 21, wherein the nucleotide sequence is SEQ ID NO: 2, or a fragment thereof.

24. A phl gene probe according to claim 21, wherein the nucleotide sequence is SEQ ID NO: 5, or a fragment thereof.

25. A phl gene probe according to claim 21, wherein the nucleotide sequence is SEQ ID NO: 7, or a fragment thereof.

26. A phl gene probe according to claim 21, wherein the nucleotide sequence is SEQ ID NO: 9, or a fragment thereof.

27. A phl gene probe according to claim 21, wherein the nucleotide sequence is SEQ ID NO: 11, or a fragment thereof.

28. A phl gene probe according to claim 21, wherein the nucleotide sequence is SEQ ID NO: 13, or a fragment thereof.

29. A phl gene probe according to claim 21, wherein the nucleotide sequence is SEQ ID NO: 15, or a fragment thereof.

30. A phl gene probe according to claim 21, wherein the nucleotide sequence is SEQ ID NO: 17, or a fragment thereof.

31. A phl gene probe according to claim 21, wherein the nucleotide sequence is SEQ ID NO: 19, or a fragment thereof.

32. A phl gene probe consisting of a nucleotide sequence selected from a group consisting of SEQ ID NO:3, or a fragment thereof of greater than 18 nucleotides in length and which hybridizes to the complementary strand of SEQ ID NO:3 under high stringency wash conditions.

33. A phl gene probe consisting of a nucleotide sequence selected from a group consisting of SEQ ID NO:4, or a fragment thereof of greater than 18 nucleotides in length and which hybridizes to the complementary strand of SEQ ID NO:4 under high stringency wash conditions.

34. A bacterium comprising a nucleic acid according to claim 2.

35. A bacterium comprising a nucleic acid according to claim 3.

36. A bacterium comprising a nucleic acid according to claim 4.

37. A bacterium comprising a nucleic acid according to claim 5.

38. A bacterium comprising a nucleic acid according to claim 6.

39. A bacterium comprising a nucleic acid according to claim 7.

40. A bacterium comprising a nucleic acid according to claim 8.

41. A method for producing a Phl protein, the method comprising transforming a bacterium with a nucleic acid according to claim 2.

42. A method for producing a Phl protein, the method comprising transforming a bacterium with a nucleic acid according to claim 3.

43. A method for producing a Phl protein, the method comprising transforming a bacterium with a nucleic acid according to claim 4.

44. A method for producing a Phl protein, the method comprising transforming a bacterium with a nucleic acid according to claim 5.

45. A method for producing a Phl protein, the method comprising transforming a bacterium with a nucleic acid according to claim 6.

46. A method for producing a Phl protein, the method comprising transforming a bacterium with a nucleic acid according to claim 7.

47. A method for producing a Phl protein, the method comprising transforming a bacterium with a nucleic acid according to claim 8.

48. A method for producing a 2,4-diacetylphloroglucinol, the method comprising transforming a bacterium with a nucleic acid according to claim 20.

49. A phl gene probe consisting of a nucleotide sequence selected from a group consisting of SEQ ID NOS: 1, 2, 5, 7, 9, 11, 13, 15, 17 and 19, or a fragment thereof of at least 18 nucleotides in length and which hybridizes to the complementary strand of the corresponding SEQ ID NO: 1, 2, 5, 7, 9, 11, 13, 15, 17 or 19 under low stringency wash conditions.

50. A phl gene probe consisting of a nucleotide sequence selected from a group consisting of SEQ ID NO:3, or a fragment thereof of greater than 18 nucleotides in length and which hybridizes to the complementary strand of SEQ ID NO:3 under low stringency wash conditions.

51. A phl gene probe consisting of a nucleotide sequence selected from a group consisting of SEQ ID NO:4, or a fragment thereof of greater than 18 nucleotides in length and which hybridizes to the complementary strand of SEQ ID NO:4 under low stringency wash conditions.

* * * * *